US011753387B2

(12) United States Patent
Dobelmann-Mara et al.

(10) Patent No.: US 11,753,387 B2
(45) Date of Patent: Sep. 12, 2023

(54) COMPOUNDS FOR OPTICALLY ACTIVE DEVICES

(71) Applicant: Johnson & Johnson Surgical Vision, Inc., Irvine, CA (US)

(72) Inventors: Lars Dobelmann-Mara, Darmstadt (DE); Stefan Riedmueller, Frankfurt am Main (DE); Martin Schraub, Alsbach-Haehnlein (DE)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 884 days.

(21) Appl. No.: 16/486,312

(22) PCT Filed: Feb. 14, 2018

(86) PCT No.: PCT/EP2018/053631
§ 371 (c)(1),
(2) Date: Aug. 15, 2019

(87) PCT Pub. No.: WO2018/149856
PCT Pub. Date: Aug. 23, 2018

(65) Prior Publication Data
US 2019/0389827 A1 Dec. 26, 2019

(30) Foreign Application Priority Data
Feb. 15, 2017 (EP) ................................. 17156326

(51) Int. Cl.
| | |
|---|---|
| *C07D 307/79* | (2006.01) |
| *A61L 27/16* | (2006.01) |
| *C07D 209/08* | (2006.01) |
| *C07D 209/12* | (2006.01) |
| *C07D 307/80* | (2006.01) |
| *C07D 333/54* | (2006.01) |
| *C07D 333/56* | (2006.01) |
| *C07D 405/04* | (2006.01) |
| *C07D 409/04* | (2006.01) |
| *C08F 20/68* | (2006.01) |

(52) U.S. Cl.
CPC ............ *C07D 307/79* (2013.01); *A61L 27/16* (2013.01); *C07D 209/08* (2013.01); *C07D 209/12* (2013.01); *C07D 307/80* (2013.01); *C07D 333/54* (2013.01); *C07D 333/56* (2013.01); *C07D 405/04* (2013.01); *C07D 409/04* (2013.01); *C08F 20/68* (2013.01)

(58) Field of Classification Search
None
See application file for complete search history.

(56) References Cited

U.S. PATENT DOCUMENTS

| | | | |
|---|---|---|---|
| 3,351,482 A | 11/1967 | Roderich et al. | |
| 3,420,835 A | 1/1969 | Wirth et al. | |
| 4,103,256 A | 7/1978 | Hammond et al. | |
| 4,230,850 A | 10/1980 | Briet et al. | |
| 4,349,619 A | 9/1982 | Kamoshida et al. | |
| 4,785,004 A | 11/1988 | Von Sprecher et al. | |
| 5,077,335 A * | 12/1991 | Schwabe ............... | C09B 35/215 264/2.6 |
| 5,290,892 A | 3/1994 | Namdaran et al. | |
| 5,331,073 A | 7/1994 | Weinschenk et al. | |
| 5,585,385 A | 12/1996 | Natsugari et al. | |
| 5,693,095 A | 12/1997 | Freeman et al. | |
| 5,968,952 A | 10/1999 | Venet et al. | |
| 6,143,766 A | 11/2000 | Kaltenbronn et al. | |
| 6,201,087 B1 | 3/2001 | Herr et al. | |
| 6,331,562 B1 | 12/2001 | Bhagwat et al. | |
| 6,887,269 B1 | 5/2005 | Hampp et al. | |
| 7,247,646 B2 | 7/2007 | McKie et al. | |
| 7,399,767 B2 | 7/2008 | Zhang et al. | |
| 7,642,364 B2 | 1/2010 | Liu et al. | |
| 8,109,999 B2 | 2/2012 | Hampp | |
| 8,247,511 B2 | 8/2012 | Mentak | |
| 8,329,849 B2 | 12/2012 | Iji et al. | |
| 8,366,963 B2 | 2/2013 | Goto et al. | |
| 8,592,007 B2 | 11/2013 | Goetz et al. | |
| 9,315,496 B2 | 4/2016 | Zhang et al. | |
| 9,580,653 B2 | 2/2017 | Archetti et al. | |
| 9,777,216 B2 | 10/2017 | Klasen-Memmer et al. | |
| 9,823,492 B2 | 11/2017 | De Sio et al. | |
| 10,351,771 B2 | 7/2019 | Goebel et al. | |
| 10,386,653 B2 | 8/2019 | Beaton et al. | |

(Continued)

FOREIGN PATENT DOCUMENTS

| | | |
|---|---|---|
| CN | 102532015 B | 10/2013 |
| CN | 104656272 A | 5/2015 |

(Continued)

OTHER PUBLICATIONS

M. Schraub et al., "Photoinduced refractive index changes of 3-phenyl-coumarin containing polymers for ophthalmic applications" European Polymer Journal, vol. 51, 2014, pp. 21-27.

C.H. Krauch et al., "Photochemische C4- und C30-Cyloadditionen an Cumaron" Chemische Berichte Jahrg, vol. 99, 1966, pp. 1723.

A. Bouquet et al., "Photoreactivie De Systemes Hexatrieniques Heterocycliques. Aryl-2 ET 3 Benxo [b] thiophene" Tetrahedron, vol. 37, 1981, pp. 75-81.

David L. Oldroyd et al., "Photochemical Dimerization Reactions of N-Acylindoles" Tetrahedron Letters, vol. 34, No. 7, 1993, pp. 1087-1090.

P.L. Beaulieu et al., "Discovery of the First Thumb Pocket 1 NS5B Polymerase Inhibitor (BILB 1941) with Demonstrated Antiviral Activity in Patients Chronically Infected with Genotype 1 Hepatitis C Virus (HCV)" Journal of Medicinal Chemistry, vol. 55, No. 17, 2012, pp. 7650-7666.

(Continued)

*Primary Examiner* — Samantha L Shterengarts
(74) *Attorney, Agent, or Firm* — Johnson & Johnson Surgical Vision, Inc.

(57) ABSTRACT

The present invention relates to novel compounds, particularly to compounds comprising a photoactive unit, said novel compounds being particularly suitable for compositions and ophthalmic devices as well as to compositions and ophthalmic devices comprising such compounds.

34 Claims, No Drawings

(56) References Cited

U.S. PATENT DOCUMENTS

| | | |
|---|---|---|
| 10,414,743 B2 | 9/2019 | Taugerbeck et al. |
| 10,457,658 B2 | 10/2019 | Dobelmann-Mara et al. |
| 10,723,713 B2 | 7/2020 | Dobelmann-Mara et al. |
| 10,829,451 B2 | 11/2020 | Dobelmann-Mara et al. |
| 11,001,576 B2 | 5/2021 | Dobelmann-Mara et al. |
| 11,014,900 B2 | 5/2021 | Dobelmann-Mara et al. |
| 11,014,901 B2 | 5/2021 | Schraub et al. |
| 11,040,990 B2 | 6/2021 | Dobelmann-Mara et al. |
| 11,078,177 B2 | 8/2021 | Dobelmann-Mara et al. |
| 11,111,226 B2 | 9/2021 | Dobelmann-Mara et al. |
| 2005/0054586 A1 | 3/2005 | Bartels et al. |
| 2005/0176763 A1 | 8/2005 | Boy et al. |
| 2006/0147840 A1 | 7/2006 | Ishidai |
| 2007/0053831 A1 | 3/2007 | Barrio et al. |
| 2008/0004610 A1 | 1/2008 | Miller et al. |
| 2009/0143858 A1 | 6/2009 | Knox et al. |
| 2010/0160482 A1 | 6/2010 | Nachbaur |
| 2010/0227273 A1 | 9/2010 | Hatakeyama et al. |
| 2010/0228345 A1 | 9/2010 | Bille |
| 2010/0324165 A1 | 12/2010 | Ritter et al. |
| 2011/0021522 A1 | 1/2011 | Wells et al. |
| 2011/0028667 A1 | 2/2011 | Ritter et al. |
| 2011/0092612 A1 | 4/2011 | Miki et al. |
| 2011/0245919 A1 | 10/2011 | Pettit |
| 2013/0114010 A1 | 5/2013 | Goetz et al. |
| 2016/0081852 A1 | 3/2016 | Peyman |
| 2018/0086725 A1 | 3/2018 | Kumar et al. |
| 2018/0243082 A1 | 8/2018 | Zheleznyak et al. |
| 2020/0002304 A1 | 1/2020 | Dobelmann-Mara et al. |
| 2020/0038549 A1 | 2/2020 | Stoy et al. |
| 2020/0332041 A1 | 10/2020 | Dobelmann-Mara et al. |
| 2021/0363122 A1 | 11/2021 | Dobelmann-Mara et al. |

FOREIGN PATENT DOCUMENTS

| | | |
|---|---|---|
| CN | 106810559 A | 6/2017 |
| CN | 105753837 B | 4/2018 |
| CN | 106810560 B | 3/2019 |
| EP | 0155177 A2 | 9/1985 |
| EP | 1342770 B1 | 5/2006 |
| EP | 1926454 B1 | 3/2010 |
| EP | 1958945 B1 | 11/2014 |
| EP | 1683792 B9 | 10/2016 |
| EP | 2698369 B1 | 2/2017 |
| EP | 3133065 A1 | 2/2017 |
| EP | 3363791 A1 | 8/2018 |
| FR | 2118191 A1 | 7/1972 |
| GB | 1212174 A | 11/1970 |
| JP | S52122371 A | 10/1977 |
| JP | S5735850 A | 2/1982 |
| JP | S5735850 U | 2/1982 |
| JP | H03275681 A | 12/1991 |
| JP | H05263072 A | 10/1993 |
| JP | H08301849 A | 11/1996 |
| JP | H08337583 A | 12/1996 |
| JP | 2876129 B2 | 3/1999 |
| JP | H11514635 A | 12/1999 |
| JP | 3275681 B2 | 4/2002 |
| JP | 2004203751 A | 7/2004 |
| JP | 2007505835 A | 3/2007 |
| JP | 2007510674 A | 4/2007 |
| JP | 2011505932 A | 3/2011 |
| JP | 2012506878 A | 3/2012 |
| JP | 2012124297 A | 6/2012 |
| JP | 5263072 B2 | 8/2013 |
| WO | 0008026 A2 | 2/2000 |
| WO | 0118079 A1 | 3/2001 |
| WO | 2005028472 A1 | 3/2005 |
| WO | 2006078834 A1 | 7/2006 |
| WO | 07033831 A1 | 3/2007 |
| WO | 2007066755 A1 | 6/2007 |
| WO | 2007082178 A2 | 7/2007 |
| WO | 2007132948 A1 | 11/2007 |
| WO | 2007136125 A1 | 11/2007 |
| WO | 2008013950 A2 | 1/2008 |
| WO | 2008094476 A1 | 8/2008 |
| WO | 2008096673 A1 | 8/2008 |
| WO | 2009032754 A2 | 3/2009 |
| WO | 09074520 A2 | 6/2009 |
| WO | 09074521 A1 | 6/2009 |
| WO | 2010049044 A1 | 5/2010 |
| WO | 2010049269 A1 | 5/2010 |
| WO | 2010049270 A1 | 5/2010 |
| WO | 2010086484 A1 | 8/2010 |
| WO | 2011057942 A1 | 5/2011 |
| WO | 2011098224 A1 | 8/2011 |
| WO | 2011117195 A1 | 9/2011 |
| WO | 2012097858 A1 | 7/2012 |
| WO | 2012150550 A1 | 11/2012 |
| WO | 2013130689 A1 | 9/2013 |
| WO | 2014090362 A1 | 6/2014 |
| WO | 2016146583 A1 | 9/2016 |
| WO | 16200401 A1 | 12/2016 |
| WO | 2017032442 A1 | 3/2017 |
| WO | 2017032443 A1 | 3/2017 |
| WO | 2017032444 A1 | 3/2017 |
| WO | 2017221068 A1 | 12/2017 |
| WO | 2018149850 A1 | 8/2018 |
| WO | 2018149852 A1 | 8/2018 |
| WO | 2018149853 A1 | 8/2018 |
| WO | 2018149855 A1 | 8/2018 |
| WO | 2018149856 A1 | 8/2018 |
| WO | 2018149857 A1 | 8/2018 |
| WO | 2018171688 A1 | 9/2018 |

OTHER PUBLICATIONS

Thanh Truong et al., "General Method for Functionalized Polyaryl Synthesis via Aryne Intermediates" J. Am. Chem. Soc., vol. 136, 2014, pp. 8568-8567.

J. M. G. Cowie, Polymers: Chemistry & Physics of Modern Materials, Blackie, Glasgow, Second Edition, 1991 (pp. 1-10).

IUPAC, Glossary of Basic terms in polymer Science, 1996, 68, p. 2291.

M. Schraub et al., European Polymer Journal, vol. 51, 2014, pp. 21-27.

C.H. Krauch et al., Chemische Berichte Jahrg, vol. 99, 1966, pp. 1723.

A. Bouquet et al., Tetrahedron, vol. 37, 1981, pp. 75-81.

David L. Oldroyd et al., Tetrahedron Letters, vol. 34, No. 7, 1993, pp. 1087-1090.

P.L. Beaulieu et al., Journal of Medicinal Chemistry, vol. 55, No. 17, 2012, pp. 7650-7666.

Thanh Truong et al., J. Am. Chem. Soc., vol. 136, 2014, pp. 8568-8567.

Database Registry, STN International CAS Registry No. 1105244-13-0, Mar. 13, 2010.

Database Registry, STN International CAS Registry No. 1211903-13-0, Mar. 19, 2010.

Database Registry, STN International CAS Registry No. 1211936-26-3, Mar. 19, 2010.

Database Registry, STN International CAS Registry No. 1212764-88-9, Mar. 21, 2010.

Database Registry, STN International CAS Registry No. 1212785-02-8, Mar. 21, 2010.

Schraub M., et al., "Smart Polymers Containing Substituted Coumarin Side Groups Enable Photo-induced Tuning of Focal Length of Intraocular Lenses," Ophthalmic Technologies, 2011, vol. 7885, pp. 1-11.

Schwartz D.M., et al., "Light-adjustable Lens: Development of in Vitro Nomograms," Transactions of the American Ophthalmological Society, Dec. 2004, vol. 102, pp. 67-74.

Skowronski L., et al., "Optical Properties of Coumarins Containing Copolymers," Optical Materials, Sep. 2015, vol. 47, pp. 18-23.

Smith L.E., et al., "Synthesis and Properties of Functional Poly(vinylpyrrolidinone) Hydrogels for Drug Delivery ," Polymers for Biomedical Applications, 2008, vol. 977, pp. 196-203.

Sohn E., et al., "Tuning Surface Properties of Poly(Methyl Methacrylate) Film Using Poly(Perfluoromethyl Methacrylate)s With Short

(56) References Cited

OTHER PUBLICATIONS

Perfluorinated Side Chains," Langmuir: the ACS journal of surfaces and colloids, 2016, vol. 32 (38), pp. 9748-9756.
Suratwala T., et al., "Photostability of Silylated Coumarin Dyes in Polyceram Hosts," Journal of Sol-Gel Science and Technology, 1997, vol. 8(1), pp. 973-978.
Tang E., et al., "A Convenient Solid-Phase Synthesis of Coumarins by TMSOTf-Catalyzed Intramolecular Selene-I 18 rylation of Tethered Alkenes," Synlett, 2012, vol. 23(6), pp. 907-912.
Trager J., et al., "Polymers for in vivo Tuning of Refractive Properties in Intraocular Lenses," Macromolecular Bioscience, 2008, vol. 8, pp. 177-183.
Trecourt F., et al., "Improved Synthesis of 2,3-disubstituted Pyridines by Metallation of 2-chloropyridine: a Convenient Route to Fused Polyheterocycles," Journal of the Chemical Society, Perkin Transactions, 1990, vol. 1 (9), pp. 2409-2415.
Trivedi R.H., et al.,"Post Cataract-interocular Lens (IOL) Surgery Opacification," Eye, 2002, vol. 16(3), pp. 217-241.
Vina D., et al., "8-Substituted 3-Arylcoumarins as Potent and Selective MAO-B Inhibitors: Synthesis, Pharmacological Evaluation, and Docking Studies," ChemMedChem, 2012, vol. 7(3), pp. 464-470.
Waldmann H., et al., "Reagent-Controlled Domino Synthesis of Skeletally-Diverse Compound Collections," Chemical Communications, 2008, vol. 10, pp. 1211-1213.
Wang D, et al., "Strategic Approach to 8-Azacoumarins," Organic Letters, 2017, vol. 19 (5), pp. 984-987.
Wang J., et al., "Palladium-Catalyzed Regioselective Cross-Coupling Reactions of 3-Bromo-4-tosyloxyquinolin-2(1H)-one with Arylboronic Acids. A Facile and Convenient Route to 3,4-Disubstituted Quinolin-2(1H)-ones," Advanced Synthesis & Catalysis, 2007, vol. 349, pp. 1943-1948.
Wolfbeis O.S, et al., "Darstellung Pyronokondensierter 2-Pyridone, Cumarine and 2-Chinolone mit Hilfe der Kappe-Mayer-Variante der von Pechmann-Reaktion," Monatshefte fur Chemie, 1982, vol. 113, pp. 365-370.
Wu J., et al., "Synthesis of 3,4-Disubstituted Quinolin-2(1H)-ones via Palladium-Catalyzed Regioselective Cross-Coupling Reactions of 3-Bromo-4-trifloxyquinolin-2(1H)-one with Arylboronic Acids," Chemistry Letters, 2005, vol. 34(4), pp. 550-551.
Wu X., et al., "A General Palladium-Catalyzed Carbonylative Synthesis of Chromenones from Salicylic 20 Idehydes and Benzyl Chlorides," Chemistry : A European Journal, 2013, vol. 19(37), pp. 12245-12248.
You L., et al., "Discovery of Novel Osthole Derivatives as Potential Anti-Breast Cancer Ttreatment," Bioorganic & Medicinal Chemistry Letters, 2010, vol. 20, pp. 7426-7428.
Zhang J., et al., "Enantioselective Phosphine-Catalyzed Allylic Alkylations of Mix-Indene with MBH Carbonates", Organic Letters, 2017, vol. 19(22), pp. 6080-6083.
Arnoldi A., et al., "Analogues of Phytoalexins Synthesis of Some 3-Phenylcoumarins and Their Fungicidal Activity," Journal of Agricultural and Food Chemistry, 1986, vol. 34(2), pp. 185-188.
Asif., "Overview of Diverse Pharmacological Activities of Substituted Coumarins Compounds with Therapeutic 33 Potentials," American Journal of Current Organic Chemistry, 2015, vol. 1, 16 pages.
Behm H., et al., "NOTE Crystal and Molecular Structure of a Photo Dimer of 1 ,2-dihydro 3-phenylnaphthalene, C32H28,"Journal of Crystallographic and Spectroscopic Research, 1988, vol. 18(4), pp. 471-475.
Billeret D., et al., "Convenient Synthesis of 5-Azacoumarins," Journal of Heterocyclic Chemistry, 1993, vol. 30, pp. 671-674.
Bonnetaud D, et al., "Synthesis of Formyl-3 Hydroxy-2 Pyridine and 2H-Pyrano[2,3-b] Pyridines One-2 (1)," Journal Heterocycl. Chemistry, Feb. 1972, vol. 9 (1), pp. 165-166.
Bozukova D., et al., "Polymers in Modern Ophthalmic Implants— Historical Background and Recent Advances," Materials Science and Engineering R, 2010, vol. 69(6), pp. 63-83.

Bratcher M.S., et al., "Synthesis of Bifunctional Photorefreactive Polymers with Net Gain: Design Strategy Amenable to Combinatorial Optimization," Journal of the American Chemical Society, 1998, vol. 120, pp. 9680-9681.
Brufola G., et al, "Efficient One-Pot Synthesis of 7-Azacoumarins by Knoevenagel Reaction Using Water as Reaction Medium," Heterocycles, 1997, vol. 45 (9), pp. 1715-1721.
Carrera., et al., "Synthesis of 3,4-Disubstituted Quinolin-2-(1H)-Ones via Palladium-Catalyzed Decarboxylative Arylation Reactions," Advanced Synthesis & Catalysis, 2013, vol. 355, pp. 2044-2054.
Chen K., et al., "Synthesis of Novel Polymer/Urea Peptoid Conjugates Using RAFT Polymerization," Maromolecules, 2010, vol. 43(3), pp. 1341-1348.
Cheng J., et al., "Discovery and Structure-Activity Relationship of Coumarin Derivatives as TNF-α Inhibitors," Bioorganic & Medicinal Chemistry Letters, 2004, vol. 14, pp. 2411-2415.
Database Registry, STN International CAS Registry No. 376382-75-1, Dec. 18, 2001, CAS Registry No. 376380-44-8, Dec. 18, 2001, CAS Registry No. 376378-98-2, Dec. 18, 2001.
Degorce S.L., et al., "Investigation of { E )-3-[4-[2-Oxo-3-arylchromen-4-yl)oxyphenyl[acrylic Acids as ral Selective Estrogen Receptor Down-Regulators," Journal of Medicinal Chemistry, 2015, vol. 58(8), pp. 3522-3533.
Desai S.M., et al., "Synthesis of 3-Substituted-aminopropoxy-2-hydroxycoumarin Derivatives as Possible B-Blockers," Journal of the Indian Chemical Society, Jun. 1989, vol. 66 (6), pp. 415-417.
Duguet E., et al., "New Cyclodisilazane Monomers," Journal of Organometallic Chemistry, 1993, vol. 458(1-2), pp. 9-12.
Fang J., et al., "Synthesis and Photodimerization in Self-assembled Monolayers of 7-(8-trimethoxysilyloctyloxy) Coumarin," Journal Materials Chemistry, 2001, vol. 11, pp. 2992-2995.
Fiilipenko., et al., "Effect of Intermolecular Interactions on the Formation of Mesophases in 3-aryl 7 Substituted Coumarins, and the Crystal Structure of 3-(4?-butyl)- and (4?-heptylphenyl)-7-propoxycoumarins," Bulletin of the Cademy of Sciences of the USSR, 1989, vol. 38(10), pp. 2073-2079.
Garazd M.M., et al., "Modified Coumarins. I. Synthesis of 5-phenyl-7h-furo[2, 3-g]chromen-7-ones and 9-phenyl-7h-furo-[2, 3-f]chromen-7-ones," Chemistry of Natural Compounds, 2000, vol. 36 (5), pp. 478-484.
Garazd M.M., et al., "Modified Coumarins. 29. Synthesis of Structural Analogs of Natural 6-arylfuro[3,2-g]chromen-7-ones, " Chemistry of Natural Compounds, 2009, vol. 45 (2), pp. 158-163.
Garazd M.M., et al., "Modified Coumarins. 8. Synthesis of Substituted 5-(4-methoxyphenyl)-7h-furo[3,2-g]chromen-7-ones," Chemistry of Natural Compounds, 2002, vol. 38 (6), pp. 539-548.
Gordeeva N.A., et al., "Photochemical Reactions of 7-Aminocoumarins Methyl-7-Diethylaminocoumarin with Monosubstituted Benzenes," Chemistry of 27 Heterocyclic Compounds, 1990, pp. 976-980.
Ikeda M., et al., "Effect of Microcrystalline Cellulose on the Stability of Oxazolam in Solid State," Journal of Pharmaceutical Science and Technology, 1987, vol. 47 (4), pp. 204-210.
Jafarpour F., et al., "Palladium-Catalyzed Decarboxylative Cross-Coupling Reactions: A Route for 26 Regioselective Functionalization of Coumarins," The Journal of Organic Chemistry, 2013, vol. 78(7), pp. 2957-2964.
Jenkins A.D., "Glossary of basic Terms in Polymer Science," Pure Applied Chermistry, 1996, vol. 68(12), pp. 2287-2311.
Kano S., et al., "A Facile Synthesis of 4-Phenylcarbostyrils and 4-Phenylisocarbostyril Involving Photocyclization of Benzo [b]thiophene-2-carboxanilidines and 2-Benzoylamino-3-chlorobenzo[b]thiophene," Heterocycles, 1979, vol. 12(4), pp. 489-492.
Kapoor., et al., "Synthesis of Coumarins," LABDEV, 1966, vol. 4(1), pp. 27-29.
Keijzer F., et al., "Photoacoustic Determination of the Photostability of 3-phenyl-1 ,2-dihydronaphthalene," Journal of Photochemistry and Photobiology A: Chemistry, 1990, vol. 50(3), pp. 401-406.
Kienast A., et al., "Influence of a New Surface Modification of Intraocular Lenses With Fluoroalkylsilan on the Adherence of

(56) References Cited

OTHER PUBLICATIONS

Endophthalmitis-causing Bacteria in Vitro," Graefe's Archive for Clinical and Experimental Ophthalmology, 2006, vol. 244(9), pp. 1171-1177.

Korchia L., et al., "UV-Responsive Amphiphilic Graft Copolymers based on Coumarin and Polyoxazoline," Soft Matter, Jan. 2017, vol. 13(25), pp. 4507-4519.

Krejcoves J., et al., "The Use of Coumarin Derivatives in the Preparation of Fluorescence-labelled Poly [N-(2-hydroxypropyl)methacrylamide]," Collection of Czechoslovak Chemical Communications, 1980, vol. 45(3), pp. 727-731.

Kurosawa T., et al., "Analysis of Stereoisomeric C27-Bile Acids by High Performance Liquid Chromatography with Fluorescence Detection," Journal of Pharmaceutical and Biomedical Analysis, 1997, vol. 15(9-10), pp. 1375-1382.

Lamberts J.J.M., et al., "The Photochemistry of 1-3- and 4-phenyl-substituted 1,2 Dihydronaphthalenes," Recueil, Journal of the Royal Netherlands Chemical Society, 1984, vol. 103(4), pp. 131-135.

Lee M.S., et al., "Photodependent Release from Poly(vinyl alcohol)/Epoxypropoxy Coumarin Hydrogels," Journal of Applied Polymer Science, 2012, vol. 124, pp. 4339-4345.

Legeais J.M., et al., "In Vivo Study of a Fluorocarbon Polymer-Coated Intraocular Lens in a Rabbit Model," Journal of Cataract and Refractive Surgery, 1998, vol. 24(3), pp. 371-379.

Li M., et al., "Evaluation of Vinylsulfamides as Sulfhydryl Selective Alkylation Reagents in Protein Modification," A Bioorganic & Medicinal Chemistry Letters, 2003, pp. 383-386.

Liao J.H., et al., "Anti-UVC Irradiation and Metal Chelation Properties of 6-Benzoyl-5,7-dihydroxy-4-phenyl-16 hromen-2-0ne: An Implication for Anti-Cataract Agent," International Journal of Molecular Sciences, 2011, vol. 12, pp. 7059-7076.

Lin W., et al., "Through-Bond Energy Transfer Cassettes With Minimal Spectral Overlap Between the Donor Emission and Acceptor Absorption: Coumarin-rhodamine Dyads With Large Pseudo-Stokes Shifts and Emission Shifts," Angewandte Chemie, 2010, vol. 49(2), pp. 375-379.

Lunazzi L., et al., "Stereomutation of Axially Chiral Aryl Coumarins," The Journal of Organic Chemistry, 2010, vol. 75(17), pp. 5927-5933.

Martin S., et al., "Smart Polymers Containing Substituted Coumarin Side Groups Enable Photo-Induced uning 29 ffocallength of Intraocular Lenses," Ophthamlmic Technologies XX1, 2011, vol. 7885, pp. 8225-6705.

Matos M.J., et al., "Insight into the Interactions between Novel Coumarin Derivatives and Human A3 Adenosine Receptors," chemMedChem, 2014, vol. 9, pp. 2245-22532.

Miyata A., et al., "Clinical and Experimental Observations of Glistening in Acrylic Intraocular Lenses," Japanese Journal of Ophthalmology, 2001, vol. 45(6), pp. 564-569.

Miyata A., et al., "Equilibrium Water Content and Glistenings in Acrylic Intraocular Lenses," Journal of Cataract and Refractive Surgery, 2004, vol. 30(8), pp. 1768-1772.

Moffett R.B., et al., "Azacoumarins," Journal of Organic Chemistry, 1970, vol. 35 (11), pp. 3596-3600.

Nasu S., Preparation of Lamellar Inorganic-Organic Hybrids from Tetraethoxysilane and a Coumarin Derivative Containing a Ttriethoxysilylgroup and Photodimerization of the Interlayer Coumaringroups,"Journal of Materials Chemistry," 2010, vol. 20, pp. 6688-6695.

Parenti M.D., et al., "Three-Dimensional Quantitative Structure-Activity Relationship Analysis of a set of Plasmodium Falciparum Dihydrofolate Reductase Inhibitors using a Pharmacophore Generation Approach," Journal of Medicinal Chemistry, 2004, vol. 47(17), pp. 4258-4267.

Qin et al., Polymer International, 1999, vol. 48, pp. 491-494.

Rampazzo E., et al., "Surface Modification of Silica Nanoparticles: a New Strategy for the Realization of Self-organized Fluorescence Chemosensors," Journal of Materials Chemistry, 2005, vol. 15 (27-28), pp. 2687-2696.

Sangwan N.K., et al., "4-Alkyl-3-phenyl-2H-1-benzopyran-2-ones and Related Compounds as Potential Pesticides," Indian Journal of Chemistry, 1990, vol. 298, pp. 294-296.

Sato Y., et al., "Studies on New-adrenergic Blocking Agents. I. Syntheses and Pharmacology of Coumarin Derivatives," Chemical and Pharmaceutical Bulletin, 1972, vol. 20 (5), pp. 905-917.

Schmidt G.M.J., "Photodimerization in the Solid State," Pure and Applied Chemistry, 1971, vol. 27, pp. 647-678.

Federal Register, vol. 76 (27), Feb. 9, 2011, pp. 7166.

* cited by examiner

COMPOUNDS FOR OPTICALLY ACTIVE DEVICES

FIELD OF THE INVENTION

The present invention relates to novel compounds, particularly to compounds comprising a photoactive unit, said novel compounds being particularly suitable for compositions and ophthalmic devices as well as to compositions and ophthalmic devices comprising such compounds.

BACKGROUND OF THE INVENTION

Cataract is a general term for an affection of the eye that leads to a loss of vision and in the extreme to blindness by clouding of the normally clear lens of the eye. It is the major cause of blindness in the world, affecting more than 100 million people. Due to the fact that its major cause is age and the population's average age is increasing, it is expected that the number of cataracts will continue to increase substantially in the future.

Effective treatment of cataract is only possible by surgical intervention, whereby the natural lens of the eye is removed through an incision in the cornea and replaced with an artificial lens, often also referred to as "intraocular lens". In preparation of surgery current state-of-the-art surgical methods employ eye mapping so as to approximate the refractive power best suited to the respective patient.

Even though cataract surgery is one of the most widely used and safest surgical procedures it is not without specific post-surgery problems. It frequently happens that the refractive power of the implanted intraocular lens (IOL) is insufficient for restoring good vision. Such problems may, for example, be caused by changes in eye geometry as consequence of the surgery as well as irregular wound healing and positioning errors that result in the artificial lens not having the optimal optical properties. As a result the patient will still require corrective vision aids, e.g. glasses, to be able to see correctly. In some cases the resulting refractive power of the implanted artificial lens is so far removed from the required refractive power that further surgery will be required. Particularly for aged persons this is not desirable because the body's capability for healing is reduced with increasing age. Furthermore, there is the risk of attracting endophthalmitis, an inflammation of the eye, which can even lead to a complete loss of vision or worse, loss of the eye.

There is therefore a need in the health sector for optically active devices, and particularly for artificial intraocular lenses, that would allow for non-invasive adjustment of refractive power after implantation of the lens, thereby preferably further reducing the need for post-surgery vision aids.

Some developments in this sense have already been made, as for example evidenced by WO 2007/033831 A1, WO 2009/074520 A2 or US 20100324165 A1.

WO 2016/200401 A1 describes liquid crystal materials having photoalignment properties such as 6-(4-(benzofuran-2-yl)phenoxy)hexyl methacrylate.

P. L. Beaulieu et al, Journal of Medicinal Chemistry, 2012, 55, 17, 7650-7666 describes indole derivatives as inhibitors satisfying potency criteria and displaying improved in vitro ADME profiles.

Thanh Truong et al, J. Am. Chem. Soc. 2014, 136, 8568-8567 describes a general method for functionalized polyaryl synthesis via aryne intermediates including transmetalation of biaryl lithium intermediates to aryl copper reagents and their further reactivity leading to compounds of table 7 on page 8574.

M. Schraub et al, European Polymer Journal 51 (2014) 21-27 describes the photochemistry of 3-phenyl-coumarin containing polymethacrylates.

C. H. Krauch et al, Chemische Berichte Jahrg. 99, 1966, 1723 describe photochemical reactions on coumaron.

A. Bouquet et al, Tetrahedron, 1981, vol. 37, 75 to 81 describe the photochemical behavior of several benzo[b]thiophenes in neutral solutions or in the presence of primary and tertiary amines.

David L. Oldroyd et al, Tetrahedron Letters, 1993, vol. 34, no. 7, 1087-1090 describe photochemical dimerization reactions of N-acylindoles.

However, the compounds disclosed so far suffer from being too stiff and too brittle so that they can't be rolled or folded and are thus not fit to be implanted by state of the art cataract surgical methods, particularly by state of the art micro-incision cataract surgical methods.

Consequently, it is an objective of the present application to provide for novel compounds suitable for ophthalmic devices.

It is also an objective of the present application to provide for compounds, the optical properties of which may be changed, preferably by non-invasive techniques.

It is a further objective of the present application to provide for novel compounds having advantages over currently known compounds, preferably in combination with being suitable for ophthalmic devices.

Advantages such as better flexibility and objectives of the compounds of the present application will be evident to the skilled person from the following detailed description as well as from the examples.

SUMMARY OF THE INVENTION

The present inventors have now found that the above objects may be attained either individually or in any combination by the compounds and ophthalmic devices of the present application.

The invention relates to compounds of formula (I)

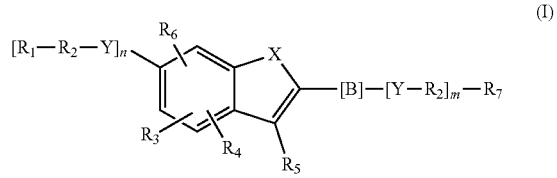

wherein
X is O, S or $NR_0$,
Y is independently of each other O, S or a bond,
n is 0 or 1,
m is 0 or 1,
n+m is 1 or 2,
—[B]— is selected from the group consisting of formula (1) to formula (4),

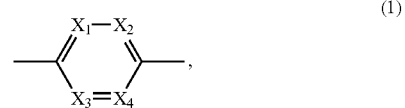

-continued

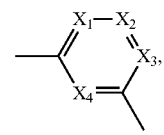
(2)

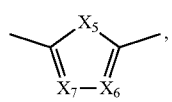
(3)

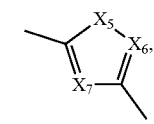
(4)

$X_1$, $X_2$, $X_3$, $X_4$ are each independently of each other CR' or N,
$X_5$ is each independently O, S, C=O or NR$_0$,
$X_6$, $X_7$ are each independently CR' or N,
R is at each occurrence independently selected from the group consisting of H, a linear or branched alkyl group having 1 to 10 C atoms or a cycloalkyl group having 3 to 6 C atoms,
R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms,
$R_0$ is at each occurrence independently selected from the group consisting of a linear or branched alkyl group having 1 to 10 C atoms or a cycloalkyl group having 3 to 6 C atoms,
$R_1$ is a polymerizable group selected from the group consisting of
an alkenyl group of formula (5),

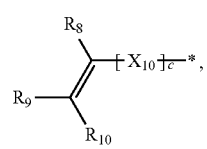
(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1; and
trialkoxysilyl groups or dialkoxyalkylsilyl groups where the alkyl and/or alkoxy groups are each independently linear or branched having 1 to 6 C atoms; and silyl groups of formula (6), (7) or (8),

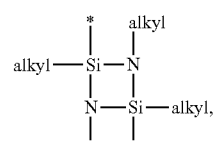
(6)

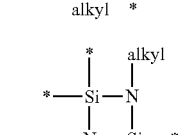
(7)

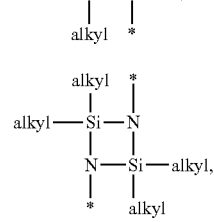
(8)

where alkyl means at each occurrence independently of each other a linear or branched alkyl group having 1 to 6 C atoms and the asterisk "*" denotes at each occurrence independently of each other a linkage to the linker [—$R_2$—Y]$_n$ and/or [Y—$R_2$]$_m$,
—$R_2$— is —(C(R)$_2$)$_o$— or —(C(R)$_2$)$_p$—$X_8$—(C(R)$_2$)$_q$—($X_9$)$_s$—(C(R)$_2$)$_r$—,
o is selected from the group consisting of 1 to 20,
$X_8$, $X_9$ are at each occurrence independently O, S or NR$_0$,
s is 0 or 1,
p, q are at each occurrence independently selected from the group consisting of 1 to 10,
r is at each occurrence independently selected from the group consisting of 0 to 10, wherein the overall number of atoms for —(C(R)$_2$)$_p$—$X_8$—(C(R)$_2$)$_q$—($X_9$)$_s$—(C(R)$_2$)$_r$— is up to 20 atoms,
$R_3$, $R_4$, $R_5$, $R_6$ are at each occurrence independently R',
$R_7$ is R' in case m is 0 and
$R_7$ is $R_1$ in case m is 1,
wherein 6-(4-(benzofuran-2-yl)phenoxy)hexyl methacrylate is excluded.

The invention relates further to compositions comprising at least one of said compounds of formula (I) and/or their polymerized forms as well as to articles comprising at least one polymerized compound of formula (I).

In addition, the invention relates to a process for forming such article, said process comprising the steps of
providing a composition comprising at least one compound of formula (I) and/or an oligomer or polymer as described before;
subsequently forming the article of said composition.

Furthermore, the invention relates to a process for changing the optical properties of an article according to the invention, said process comprising the steps of
providing an article comprising at least one polymerized compound of formula (I), and
subsequently exposing said article to irradiation having a wavelength of at least 200 nm and at most 1500 nm.

DETAILED DESCRIPTION OF THE INVENTION

The compounds of formula (I) and all preferred embodiments of compounds of formula (I) according to the present invention include all stereoisomers or racemic mixtures.

The compounds of formula (I) provide several advantages over prior art materials by adding a linker—[B]— to the benzo[b]furan, benzo[b]thiophene or benzo[b]pyrrol ring system their melting point or glass transition temperature will decrease and π stacking will be disturbed, thus being better foldable or bendable.

In comparison to known coumarin-type photoactive chromophores, compounds according to the invention are more stable toward UV-irradiation due to lower absorption range. Furthermore the chemical and hydrolytical stability is higher and given due to their intrinsic chemical nature e.g. due to lack of positions prone to nucleophilic attacks, like $sp^2$ centers and the absence of cyclic lactone structure motifs, compared to coumarin-type photoactive chromophores.

Polymers that are foldable at room temperature generally exhibit glass transition temperatures ($T_g$) lower than room temperature (ca. 21° C.). They are easily deformable at this temperature without causing physical damage to the polymer, for example by inducing creep, stress or fissures. For polymers in intraocular lenses, $T_g$s of less than or equal to 15° C. are preferred.

Polymers used in intraocular lens manufacturing have preferably relative high refractive indices, which enable the fabrication of thinner intraocular lenses. Preferably, the polymer used in an intraocular lens will have a refractive index greater than about 1.5 and presently most preferably greater than about 1.55.

In case an asterisk ("*") is used within the description of the present invention, it denotes a linkage to an adjacent unit or group or, in case of a polymer, to an adjacent repeating unit or any other group.

A linear or branched alkyl group having 1 to 10 C atoms denotes an alkyl group having 1, 2, 3, 4, 5, 6, 7, 8, 9 or 10 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl or n-decyl. A linear or branched alkyl group having 1 to 20 C atoms include all examples for a linear or branched alkyl group having 1 to 10 C atoms including any alkyl group having 11, 12, 13, 14, 15, 16, 17, 18, 19 and 20 C atoms such as n-undecyl, n-dodecyl, n-tridecyl, n-tetradecyl, n-pentadecyl, n-hexadecyl, n-heptadecyl, n-octadecyl, n-nonadecyl and n-eicosyl.

The term partially halogenated alkyl group denotes that at least one H atom of the alkyl group is replaced by F, Cl, Br or I. Preferably, the alkyl group is partially fluorinated meaning that at least one H atom of the alkyl group is replaced by F.

The term completely halogenated alkyl group denotes that all H atoms of the alkyl group are replaced by F, Cl, Br and/or I. Preferably, the alkyl group is completely fluorinated meaning that all H atoms of the alkyl group are replaced by F. A preferred completely fluorinated alkyl group is trifluoromethyl.

The term halogenated or preferably fluorinated corresponds additionally to other groups such as a halogenated cycloalkyl group, a halogenated alkoxy group or a halogenated thioalkyl group.

A linear or branched hydroxyalkyl group having 1 to 20 C atoms denotes an alkyl group having 1, 2, 3, 4, 5, 6, 7, 8, 9, 10, 11, 12, 13, 14, 15, 16, 17, 18, 19 or 20 C atoms wherein at least one H atom is replaced by a hydroxyl group (—OH). The hydroxyl group is preferably replaced on the last C atom of the alkyl group, for example hydroxymethyl, 2-hydroxyethyl, 3-hydroxy-propyl, 4-hydroxy-butyl, 5-hydroxy-pentyl, 4-hydroxy-1-, -2- or -3-methylbutyl, 3-hydroxy-1,1-, -1,2- or -2,2-dimethylpropyl, 3-hydroxy-1-ethylpropyl, 6-hydroxy-hexyl, 7-hydroxy-heptyl, 8-hydroxy-octyl, 6-hydroxy-1-ethylhexyl, 9-hydroxy-nonyl, 10-hydroxy-decyl, 11-hydroxy-undecyl, 12-hydroxy-dodecyl, 13-hydroxy-tridecyl, 14-hydroxy-tetradecyl, 15-hydroxy-pentadecyl, 16-hydroxy-hexadecyl, 17-hydroxy-heptadecyl, 18-hydroxy-octadecyl, 19-hydroxy-nonadecyl and 20-hydroxy-eicosyl. A preferred hydroxyalkyl group is 3-hydroxy-propyl.

A cycloalkyl group having 3 to 6 C atoms includes cyclopropyl, cyclobutyl, cyclopentyl and cyclohexyl which may be partially or completely halogenated or fluorinated as explained before.

A linear or branched alkoxy group having 1 to 20 C atoms denotes an O-alkyl group having 1, 2, 3, 4, 5, 6, 7, 8, 9, 10, 11, 12, 13, 14, 15, 16, 17, 18, 19 or 20 C atoms, for example methoxy, ethoxy, iso-propoxy, n-propoxy, iso-butoxy, n-butoxy, tert-butoxy, n-pentyloxy, 1-, 2- or 3-methylbutyloxy, 1,1-, 1,2- or 2,2-dimethylpropoxy, 1-ethylpropoxy, n-hexyloxy, n-heptyloxy, n-octyloxy, ethylhexyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy and n-eicosyloxy which may be partially or completely halogenated or preferably may be partially or completely fluorinated. A preferred completely fluorinated alkoxy group is trifluoromethoxy.

A linear or branched thioalkyl group having 1 to 20 C atoms denotes a S-alkyl group having 1, 2, 3, 4, 5, 6, 7, 8, 9, 10, 11, 12, 13, 14, 15, 16, 17, 18, 19 or 20 C atoms, for example thiomethyl, 1-thioethyl, 1-thio-iso-propyl, 1-thio-n-propyl, 1-thio-iso-butyl, 1-thio-n-butyl, 1-thio-tert-butyl, 1-thio-n-pentyl, 1-thio-1-, -2- or -3-methylbutyl, 1-thio-1,1-, -1,2- or -2,2-dimethylpropyl, 1-thio-1-ethylpropyl, 1-thio-n-hexyl, 1-thio-n-heptyl, 1-thio-n-octyl, 1-thio-ethylhexyl, 1-thio-n-nonyl, 1-thio-n-decyl, 1-thio-n-undecyl, 1-thio-n-dodecyl, 1-thio-n-tridecyl, 1-thio-n-tetradecyl, 1-thio-n-pentadecyl, 1-thio-n-hexadecyl, 1-thio-n-heptadecyl, 1-thio-n-octadecyl, 1-thio-n-nonadecyl and 1-thio-n-eicosyl which may be partially or completely halogenated or preferably may be partially or completely fluorinated. A preferred completely fluorinated thioether group is trifluoromethyl thioether.

Preferred alkyl and alkoxy radicals have 1, 2, 3, 4, 5, 6, 7, 8, 9 or 10 C atoms.

A polymerizable group is a group which can be subject to or can undergo polymerization thus forming an oligomer or a polymer.

Polymerization is the process of taking individual monomers and chaining them together to make longer units. These longer units are called polymers. The compounds of formula (I) as described before and preferably described below are suitable monomers.

Within the gist of the invention, the polymerizable group $R_1$ once oligomerized or polymerized thus forms or is part of the backbone of the oligomer or polymer comprising polymerized compounds of formula (I). Suitable polymerizable groups contain at least one double bond or at least one triple bond thus forming polymers where the linking is formed via carbon-carbon bonds. Alternatively, a suitable polymerizable group may contain silicon thus forming polysiloxanes or polysilazanes.

The suitable polymerizable groups are selected from the group consisting of an alkenyl group of formula (5),

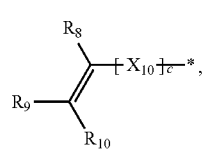

(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1;
trialkoxysilyl groups or dialkoxyalkylsilyl groups where the alkyl and/or alkoxy groups are each independently linear or branched having 1 to 6 C atoms; and
silyl groups of formula (6), (7) or (8),

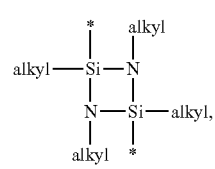

(6)

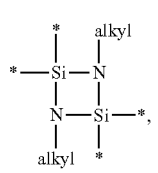

(7)

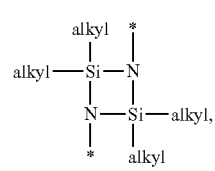

(8)

where alkyl means at each occurrence independently of each other a linear or branched alkyl group having 1 to 6 C atoms and the asterisk "*" denotes at each occurrence independently of each other a linkage to the linker $[R_2—Y]_n$ and/or $[Y—R_2]_m$ as described before or preferably described before.

A preferred polymerizable group is selected from the group consisting of trimethoxysilyl, triethoxysilyl, diethoxymethylsilyl and the alkenyl group of formula (5) as described before and preferably described below.

Aryl with 6 to 14 C atoms is an aryl group preferably selected from the group consisting of phenyl, naphthyl or anthryl, particularly preferably phenyl.

The linker—[B]— is selected from the group of formulae (1) to (4), wherein $X_1$, $X_2$, $X_3$, $X_4$ are each independently of each other CR' or N, $X_5$ is each independently O, S, C=O or $NR_0$ and $X_6$ and $X_7$ are each independently CR' or N, wherein R' and $R_0$ have a meaning as described before or preferably described below.

Preferred examples for the linker—[B]— are therefore selected from the group of formulae (B-1) to (B-34),

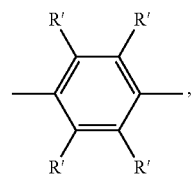

(B-1)

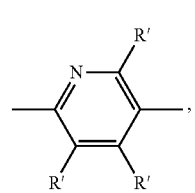

(B-2)

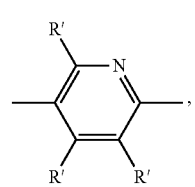

(B-3)

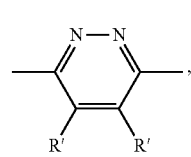

(B-4)

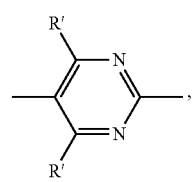

(B-5)

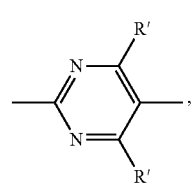

(B-6)

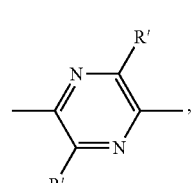

(B-7)

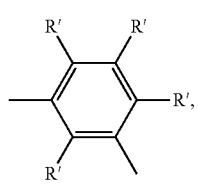

(B-8)

-continued (B-9) (B-10) (B-11) (B-12) (B-13) (B-14) (B-15) (B-16) (B-17) (B-18)

(B-19) (B-20) (B-21) (B-22) (B-23) (B-24) (B-25) (B-26) (B-27) (B-28)

-continued

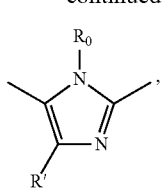
(B-29)

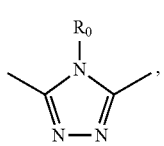
(B-30)

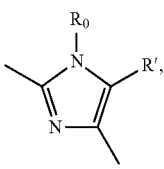
(B-31)

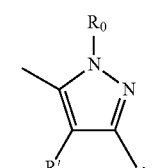
(B-32)

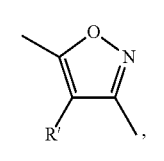
(B-33)

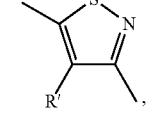
(B-34)

wherein R' and $R_0$ have a meaning as described before or preferably described below.

Compounds of formula (I) as described before are preferred where the linker—[B]— corresponds to formula (1) or (2) and $X_1$, $X_2$, $X_3$ and $X_4$ have a meaning as described before. Therefore, compounds of formula (I) are preferred where the linker—[B]— corresponds to formulae (B-1) to (B-19).

The invention therefore relates additionally to compounds of formula (I) as described before wherein—[B]— corresponds to formula (1) and (2) and $X_1$, $X_2$, $X_3$ and $X_4$ have a meaning as described before.

Compounds of formula (I) as described before are particularly preferred where the linker—[B]— corresponds to formula (1) or (2) and $X_1$, $X_3$ and $X_4$ are CR' and R' has at each occurrence independently a meaning as described before or preferably described below. Therefore, compounds of formula (I) are particularly preferred where the linker—[B]— corresponds to formulae (B-1), (B-3), (B-8) or (B-9).

The invention therefore relates additionally to compounds of formula (I) as described before wherein—[B]— corresponds to formula (1) and (2) and $X_1$, $X_3$ and $X_4$ are CR' and R' has at each occurrence independently a meaning as described before or preferably described below.

Compounds of formula (I) as described or preferably described before are especially preferred where the linker—[B]— corresponds to formula (1) or (2) and $X_2$ is CR' and R' has at each occurrence independently a meaning as described before or preferably described below. Therefore, compounds of formula (I) are especially preferred where the linker—[B]— corresponds to formulae (B-1), (B-2), (B-6), (B-7), (B-8), (B-10) or (B-11). Additionally, compounds of formula (I) having a linker—[B]— which corresponds to formula (B-1) or (B-8) are very particularly preferred and R' has at each occurrence independently a meaning as described before or preferably described below. Within these very particular preferred compounds of formula (I), it is preferred to select the linker of formula (B-1) and R' has at each occurrence independently a meaning as described before or preferably described below.

The invention therefore relates additionally to compounds of formula (I) as described or preferably described before wherein—[B]— corresponds to formula (1) and (2) and $X_2$ is CR' and R' has at each occurrence independently a meaning as described before or preferably described below.

R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms.

It is preferred that at least one R' in—[B]— as described before or preferably described before is different from H and is selected from the group consisting of F, a linear or branched, non-halogenated, partially or completely halogenated alkyl group having 1 to 20 C atoms, a non-halogenated, a linear or branched hydroxyalkyl group having 1 to 20 C atoms, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. It is particularly preferred that at least two substituents R' are different from H and are independently selected from the group consisting of F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms.

With regard to said substituent R', R' is at each occurrence independently preferably selected from the group consisting of H, F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

It is preferred that at least one R' in—[B]— as described before or preferably described before is different from H and is selected from the group consisting of F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

It is particularly preferred that at least two substituents R' are different from H and are independently selected from the group consisting of F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

R' is at each occurrence independently particularly preferably selected from the group consisting of H, F, methyl, ethyl, n-propyl, n-butyl, n-pentyl, n-hexyl, n-heptyl, n-octyl, trifluormethyl, pentafluorethyl, heptafluorpropyl, methoxy, ethoxy, propoxy, trifluormethoxy, pentafluorethoxy, 2-hydroxy-ethyl, 3-hydroxy-propyl, 4-hydroxy-butyl and 5-hydroxy-pentyl.

R' is at each occurrence independently very particularly preferably selected from the group consisting of H, F, ethyl, n-pentyl, trifluoromethyl, methoxy, trifluoromethoxy and 3-hydroxy-propyl.

Compounds of formula (I) with linkers —[B]— as defined before or preferably defined before are further preferred through their substitution pattern on the linker —[B]— preferably through the substituent R' which is independent at each occurrence.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H.

Therefore, the invention is further directed to compounds of formula (I) as described before where —[B]— corresponds to formulae (B-1) to (B-29) or (B-31) to (B-34) or to preferred linkers as described before, wherein at least one R' is not H and $R_0$ has a meaning as described before or preferably described below.

The substituent R' within $X_1$ or $X_3$ in formula (1) is particularly preferred not H and has a meaning as described before.

The substituents R' within $X_1$ and $X_3$ in formula (1) are particularly preferred not H and have a meaning as described before.

The substituent R' within $X_7$ in formula (3) is particularly preferred not H and has a meaning as described before.

As described before, the substituents $R_3$, $R_4$, $R_5$ and $R_6$ are at each occurrence independently R' where R' has a meaning or a preferred or particularly preferred meaning as described before.

$R_5$ is preferably H or F. $R_5$ is particularly preferably H.

As described before, the substituent $R_7$ corresponds to R' in case m is 0 wherein R' has a meaning or a preferred or particularly preferred meaning as described before. Preferably in case m is 0, $R_7$ corresponds to R' having a meaning as described before which is preferably not H and has a meaning as described before or preferably described before.

In all cases when R' is preferably not H, it is selected from the preferred group consisting of F, methyl, ethyl, n-propyl, n-butyl, n-pentyl, n-hexyl, n-heptyl, n-octyl, trifluormethyl, pentafluorethyl, heptafluorpropyl, methoxy, ethoxy, propoxy, trifluormethoxy, pentafluorethoxy, 2-hydroxy-ethyl, 3-hydroxy-propyl, 4-hydroxy-butyl and 5-hydroxy-pentyl or from the particular preferred group consisting of F, ethyl, n-pentyl, trifluoromethyl, methoxy, trifluoromethoxy and 3-hydroxy-propyl.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H and $R_7$ is not H in case m is 0.

Therefore, the invention is further directed to compounds of formula (I) as described before where —[B]— corresponds to formulae (B-1) to (B-29) or (B-31) to (B-34) or to preferred linkers as described before, wherein at least one R' is not H and $R_7$ is not H in case m is 0 and $R_0$ has a meaning as described before or as preferably described below.

As described before, the substituent $R_7$ corresponds to $R_1$ in case m is 1 wherein $R_1$ has a meaning or a preferred meaning as described before or further below. Compounds of formula (I) in which m is 1 are preferred having a linker —[B]— selected from the group consisting of formula (1) to (4) wherein at least one substituent R' within $X_1$, $X_2$, $X_3$, $X_4$, $X_6$ or $X_7$ is not H and in which at least one substituent $R_3$, $R_4$ or $R_6$ is not H.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H, in which at least one substituent $R_3$, $R_4$ or $R_6$ is not H and $R_7$ corresponds to $R_1$ in case m is 1.

Therefore, the invention is further directed to compounds of formula (I) as described before where —[B]— corresponds to formulae (B-1) to (B-29) or (B-31) to (B-34) or to preferred linkers as described before, wherein at least one R' is not H, in which at least one substituent $R_3$, $R_4$ or $R_6$ is not H and $R_7$ corresponds to $R_1$ in case m is 1 wherein $R_0$ and $R_1$ has a meaning as described before or further below.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]furan ring system in case X is O.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]thiophen ring system in case X is S.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]pyrrol ring system in case X is $NR_0$ and $R_0$ is independently selected from the group consisting of a linear or branched alkyl group having 1 to 10 C atoms or a cycloalkyl group having 3 to 6 C atoms.

$R_0$ is at each occurrence independently preferably methyl, ethyl, iso-propyl, 2-methyl-propyl, n-butyl, n-pentyl, 4-methyl-pentyl or cyclopropyl.

In case X is $NR_0$, $R_0$ is particularly preferably ethyl, iso-propyl, 2-methyl-propyl, n-pentyl or 4-methyl-pentyl.

In case $X_5$ is $NR_0$, $R_0$ is particularly preferably methyl or n-butyl.

In case $X_8$ or $X_9$ is $NR_0$, $R_0$ is particularly preferably methyl.

Compounds of formula (I) with linkers and substituents as described before or preferably described before or below are preferred when X is O or S.

Compounds of formula (I) with linkers and substituents as described before or preferably described before or below are particularly preferred when X is O.

In one preferred embodiment of the invention, the compounds of formula (I) as described before or preferably described before contain one polymerizable group $R_1$. This is the case for compounds of formula (I) in which n is 1 or m is 1 and the sum of n and m is 1. Such compounds can be preferably used as monomers for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 0 which can preferably be described according to formula (I')

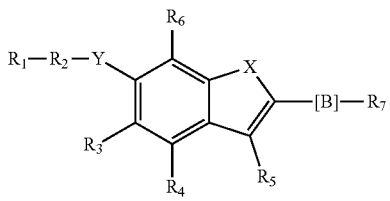

(I')

wherein $R_1$, $—R_2—$, Y, $R_3$, $R_4$, $R_5$, $R_6$, X, $—[B]—$ and $R_7$ have a meaning as described before or preferably described before or below.

The invention is therefore additionally directed to compounds of formula (I) wherein n is 0 and m is 1 which can preferably be described according to formula (I")

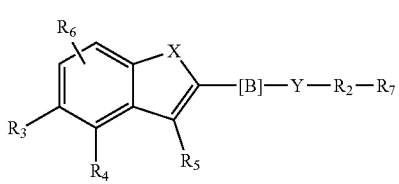

(I")

wherein $R_1$, $—R_2—$, Y, $R_3$, $R_4$, $R_5$, $R_6$, X, $—[B]—$ and $R_7$ have a meaning as described before or preferably described before or below.

Within compounds of formula (I"), o is preferably selected from the group consisting of 7, 8, 9, 10, 11, 12, 13, 14, 15, 16, 17 and 18, particularly preferably 7 to 13 or 8 to 12 and $—[B]—$ and $R_7$ have a meaning as described before or preferably described before.

In another preferred embodiment of the invention, the compounds of formula (I) as described before or preferably described before contain two polymerizable groups $R_1$. This is the case for compounds of formula (I) in which n is 1 and m is 1 and the sum of n and m is 2. Such compounds can be preferably used as cross-linking agent for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 1 which can preferably be described according to formula (I'"),

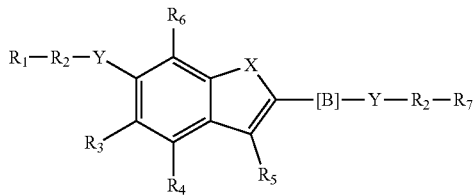

(I'")

wherein $R_1$, $—R_2—$, Y, $R_3$, $R_4$, $R_5$, $R_6$, X, $—[B]—$ and $R_7$ have a meaning as described before or preferably described before or below.

Compounds of formula (I), (I'), (I") and (I'") with linkers $—[B]—$ and substituents as described before or preferably described before have a polymerizable group as described before or preferably described before or below and have at least one linking element $Y—R_2—$.

Y is independently at each occurrence O, S or a bond.

The linking element $—R_2—$ is selected from the group consisting of $—(C(R)_2)_o—$ and $—(C(R)_2)_p—X_8—(C(R)_2)_q—(X_9)_s—(C(R)_2)_r—$, wherein o is selected from the group consisting of 1 to 20, $X_8$ and $X_9$ are at each occurrence O, S or $NR_0$, s is 0 or 1, p and q are at each occurrence independently selected from the group consisting of 1 to 10, r is at each occurrence independently selected from the group consisting of 0 to 10, wherein the overall number of atoms for $—(C(R)_2)_p—X_8—(C(R)_2)_q—(X_9)_s—(C(R)_2)_r—$ is up to 20 C atoms.

R is at each occurrence independently selected from the group consisting of H, a linear or branched alkyl group having 1 to 10 C atoms or a cycloalkyl group having 3 to 6 C atoms. R is preferably at each occurrence independently selected from the group consisting of H and a linear or branched alkyl group having 1 to 4 C atoms. R is particularly preferably at each occurrence independently H, methyl or ethyl. R is very particularly preferably H.

Preferably, o is selected from the group consisting of 3, 4, 5, 6, 7, 8, 9, 10, 11, 12, 13, 14, 15, 16, 17 and 18, particularly preferably 7 to 13 or 8 to 12.

Preferably, s is 1.
Preferably t is 0 or 1.
Preferably, $X_8$, $X_9$ and $X_{10}$ are O.
Preferably, p and q are each independently 1, 3, 3, 4, 5 or 6, particularly preferably 1 or 2.
Preferably, r is 1, 2 or 3, particularly preferably 1.

Suitable examples for $—R_2—$ are $—(CH_2)—$, $—(CH_2)_2—$, $—(CH_2)_3—$, $—(CH_2)_4—$, $—(CH_2)_5—$, $—(CH_2)_6—$, $—(CH_2)_7—$, $—(CH_2)_8—$, $—(CH_2)_9—$, $—(CH_2)_{10}—$, $—(CH_2)_{11}—$, $—(CH_2)_{12}—$, $—(CH_2)_{13}—$, $—(CH_2)_{14}—$, $—(CH_2)_{15}—$, $—(CH_2)_{16}—$, $—(CH_2)_{17}—$, $—(CH_2)_{18}—$, $—(CH_2)_{19}—$, $—(CH_2)_{20}—$, $—(CHCH_3)—$, $—(CHCH_3)_2—$, $—(CHCH_3)_3—$, $—(CHCH_3)_4—$, $—(CHCH_3)_5—$, $—(CHCH_3)_6—$, $—(CHCH_3)_7—$, $—(CHCH_3)_8—$, $—(CHCH_3)_9—$, $—(CHCH_3)_{10}—$, $—(CHCH_3)_{11}—$, $—(CHCH_3)_{12}—$, $—(CHCH_3)_{13}—$, $—(CHCH_3)_{14}—$, $—(CHCH_3)_{15}—$, $—(CHCH_3)_{16}—$, $—(CHCH_3)_{17}—$, $—(CHCH_3)_{18}—$, $—(CHCH_3)_{19}—$, $—(CHCH_3)_{20}—$, $—(C(CH_3)_2)—$, $—(C(CH_3)_2)_2—$, $—(C(CH_3)_2)_3—$, $—(C(CH_3)_2)_4—$, $—(C(CH_3)_2)_5—$, $—(C(CH_3)_2)_6—$, $—(C(CH_3)_2)_7—$, $—(C(CH_3)_2)_8—$, $—(C(CH_3)_2)_9—$, $—(C(CH_3)_2)_{10}—$, $—(C(CH_3)_2)_{11}—$, $—(C(CH_3)_2)_{12}—$, $—(C(CH_3)_2)_{13}—$, $—(C(CH_3)_2)_{14}—$, $—(C(CH_3)_2)_{15}—$, $—(C(CH_3)_2)_{16}—$, $—(C(CH_3)_2)_{17}—$, $—(C(CH_3)_2)_{18}—$, $—(C(CH_3)_2)_{19}—$, $—(C(CH_3)_2)_{20}—$, $—(CHC_2H_5)—$, $—(CHC_2H_5)_2—$, $—(CHC_2H_5)_3—$, —(CHC$_2$H$_5$)$_4$—, —(CHC$_2$H$_5$)$_5$—, —(CHC$_2$H$_5$)$_6$—, —(CHC$_2$H$_5$)$_7$—, —(CHC$_2$H$_5$)$_8$—, —(CHC$_2$H$_5$)$_9$—, —(CHC$_2$H$_5$)$_{10}$—, —(CHC$_2$H$_5$)$_{11}$—, —(CHC$_2$H$_5$)$_{12}$—, —(CHC$_2$H$_5$)$_{13}$—, —(CHC$_2$H$_5$)$_{14}$—, —(CHC$_2$H$_5$)$_{15}$—, —(CHC$_2$H$_5$)$_{16}$—, —(CHC$_2$H$_5$)$_{17}$—, —(CHC$_2$H$_5$)$_{18}$—, —(CHC$_2$H$_5$)$_{19}$—, —(CHC$_2$H$_5$)$_{20}$—, —(CH$_2$)—(CHCH$_3$)—(CH$_2$)—, —(CH$_2$)—(CHCH$_3$)—(CH$_2$)$_2$—, —(CH$_2$)—(CHCH$_3$)—(CH$_2$)$_3$—, —(CH$_2$)—(CHCH$_3$)—(CH$_2$)$_{11}$—, —(CH$_2$)$_2$—(CHCH$_3$)—(CH$_2$)—, —(CH$_2$)$_3$—(CHCH$_3$)—(CH$_2$)—, —(CH$_2$)$_{11}$—(CHCH$_3$)—(CH$_2$)—, —(CH$_2$)$_2$—O—(CH$_2$)$_2$—, —(CH$_2$)$_3$—O—(CH$_2$)$_3$—, —(CH$_2$)$_2$—O—(CH$_2$)$_2$—O—(CH$_2$)$_2$—, —(CH$_2$)$_3$—O—(CH$_2$)$_3$—O—(CH$_2$)$_3$—, —(CH$_2$)$_2$—O—(CH$_2$)$_2$—O—(CH$_2$)$_6$—, —(CH$_2$)$_6$—O—(CH$_2$)$_2$—O—(CH$_2$)$_2$—, —(CH$_2$)$_2$—O—(CH$_2$)$_2$—O—(CH$_2$)$_8$—, —(CH$_2$)$_8$—O—(CH$_2$)$_2$—O—(CH$_2$)$_2$—, —(CH$_2$)$_2$—S—(CH$_2$)$_2$—, —(CH$_2$)$_3$—S—(CH$_2$)$_3$—, —(CH$_2$)$_2$—S—(CH$_2$)$_2$—S—(CH$_2$)$_2$—, —(CH$_2$)$_3$—S—(CH$_2$)$_3$—S—(CH$_2$)$_3$—, —(CH$_2$)$_2$—S—(CH$_2$)$_2$—S—(CH$_2$)$_6$—, —(CH$_2$)$_6$—S—(CH$_2$)$_2$—S—(CH$_2$)$_2$—, —(CH$_2$)$_2$—S—(CH$_2$)$_2$—S—(CH$_2$)$_8$—, —(CH$_2$)$_8$—S—(CH$_2$)$_2$—S—(CH$_2$)$_2$—, —(CH$_2$)$_2$—(NCH$_3$)—(CH$_2$)$_2$—, —(CH$_2$)$_3$—(NCH$_3$)—(CH$_2$)$_3$—, —(CH$_2$)$_2$—(NCH$_3$)—(CH$_2$)$_2$—(NCH$_3$)—(CH$_2$)$_2$—, —(CH$_2$)$_3$—(NCH$_3$)—(CH$_2$)$_3$—(NCH$_3$)—(CH$_2$)$_3$—, —(CH$_2$)$_2$—(NCH$_3$)—(CH$_2$)$_2$—(NCH$_3$)—(CH$_2$)$_6$—, —(CH$_2$)$_6$—(NCH$_3$)—(CH$_2$)$_2$—(NCH$_3$)—(CH$_2$)$_2$—, —(CH$_2$)$_2$—(NCH$_3$)—(CH$_2$)$_2$—(NCH$_3$)—(CH$_2$)$_8$— and —(CH$_2$)$_8$—(NCH$_3$)—(CH$_2$)$_2$—(NCH$_3$)—(CH$_2$)$_2$—.

Compounds of formula (I), (I'), (I") and (I''') with linkers —[B]— and substituents as described before or preferably described before having a polymerizable group as described before or preferably described before or below are preferred in case the substituent —R$_2$— within the at least one linking element Y—R$_2$— corresponds to —(C(R)$_2$)$_o$— and R and o have a meaning as described before or preferably described before.

The invention therefore relates additionally to compounds of formula (I), (I'), (I") and (I''') as described before or preferably described before wherein —R$_2$— is at each occurrence independently —(C(R)$_2$)$_o$— and R and o have a meaning as described before.

The linking element —(C(R)$_2$)$_o$— as —R$_2$— is preferably selected from the group consisting of —(CH$_2$)—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$— and —(CH$_2$)$_{20}$—.

The linking element —(C(R)$_2$)$_o$— as —R$_2$— is particularly preferably selected from the group consisting of —(CH$_2$)$_8$—, —(CH$_2$)$_{11}$—, —(CH$_2$)$_{12}$— and —(CH$_2$)$_{13}$—.

The linking element —(C(R)$_2$)$_o$— as —R$_2$— is particularly preferably —(CH$_2$)$_{12}$—.

The substituent Y—R$_2$—R$_1$ is preferably selected from the group consisting of O—(CH$_2$)—R$_1$, O—(CH$_2$)$_2$—R$_1$, O—(CH$_2$)$_3$—R$_1$, O—(CH$_2$)$_4$—R$_1$, O—(CH$_2$)$_5$—R$_1$, O—(CH$_2$)$_6$—R$_1$, O—(CH$_2$)$_7$—R$_1$, O—(CH$_2$)$_8$—R$_1$, O—(CH$_2$)$_9$—R$_1$, O—(CH$_2$)$_{10}$—R$_1$, O—(CH$_2$)$_{11}$—R$_1$, O—(CH$_2$)$_{12}$—R$_1$, O—(CH$_2$)$_{13}$—R$_1$, O—(CH$_2$)$_{14}$—R$_1$, O—(CH$_2$)$_{15}$—R$_1$, O—(CH$_2$)$_{16}$—R$_1$, O—(CH$_2$)$_{17}$—R$_1$, O—(CH$_2$)$_{18}$—R$_1$, O—(CH$_2$)$_{19}$—R$_1$, O—(CH$_2$)$_{20}$—R$_1$, O—(CHCH$_3$)—R$_1$, O—(CHCH$_3$)$_2$—R$_1$, O—(CHCH$_3$)$_3$—R$_1$, O—(CHCH$_3$)$_4$—R$_1$, O—(CHCH$_3$)$_5$—R$_1$, O—(CHCH$_3$)$_6$—R$_1$, O—(CHCH$_3$)$_7$—R$_1$, O—(CHCH$_3$)$_8$—R$_1$, O—(CHCH$_3$)$_9$—R$_1$, O—(CHCH$_3$)$_{10}$—R$_1$, O—(CHCH$_3$)$_{11}$—R$_1$, O—(CHCH$_3$)$_{12}$—R$_1$, O—(CHCH$_3$)$_{13}$—R$_1$, O—(CHCH$_3$)$_{14}$—R$_1$, O—(CHCH$_3$)$_{15}$—R$_1$, O—(CHCH$_3$)$_{16}$—R$_1$, O—(CHCH$_3$)$_{17}$—R$_1$, O—(CHCH$_3$)$_{18}$—R$_1$, O—(CHCH$_3$)$_{19}$—R$_1$, O—(CHCH$_3$)$_{20}$—R$_1$, O—(C(CH$_3$)$_2$)—R$_1$, O—(C(CH$_3$)$_2$)$_2$—R$_1$, O—(C(CH$_3$)$_2$)$_3$—R$_1$, O—(C(CH$_3$)$_2$)$_4$—R$_1$, O—(C(CH$_3$)$_2$)$_5$—R$_1$, O—(C(CH$_3$)$_2$)$_6$—R$_1$, O—(C(CH$_3$)$_2$)$_7$—R$_1$, O—(C(CH$_3$)$_2$)$_8$—R$_1$, O—(C(CH$_3$)$_2$)$_9$—R$_1$, O—(C(CH$_3$)$_2$)$_{10}$—R$_1$, O—(C(CH$_3$)$_2$)$_{11}$—R$_1$, O—(C(CH$_3$)$_2$)$_{12}$—R$_1$, O—(C(CH$_3$)$_2$)$_{13}$—R$_1$, O—(C(CH$_3$)$_2$)$_{14}$—R$_1$, O—(C(CH$_3$)$_2$)$_{15}$—R$_1$, O—(C(CH$_3$)$_2$)$_{16}$—R$_1$, O—(C(CH$_3$)$_2$)$_{17}$—R$_1$, O—(C(CH$_3$)$_2$)$_{18}$—R$_1$, O—(C(CH$_3$)$_2$)$_{19}$—R$_1$, O—(C(CH$_3$)$_2$)$_{20}$—R$_1$, O—(CHC$_2$H$_5$)—R$_1$, O—(CHC$_2$H$_5$)$_2$—R$_1$, O—(CHC$_2$H$_5$)$_3$—R$_1$, O—(CHC$_2$H$_5$)$_4$—R$_1$, O—(CHC$_2$H$_5$)$_5$—R$_1$, O—(CHC$_2$H$_5$)$_6$—R$_1$, O—(CHC$_2$H$_5$)$_7$—R$_1$, O—(CHC$_2$H$_5$)$_8$—R$_1$, O—(CHC$_2$H$_5$)$_9$—R$_1$, O—(CHC$_2$H$_5$)$_{10}$—R$_1$, O—(CHC$_2$H$_5$)$_{11}$—R$_1$, O—(CHC$_2$H$_5$)$_{12}$—R$_1$, O—(CHC$_2$H$_5$)$_{13}$—R$_1$, O—(CHC$_2$H$_5$)$_{14}$—R$_1$, O—(CHC$_2$H$_5$)$_{15}$—R$_1$, O—(CHC$_2$H$_5$)$_{16}$—R$_1$, O—(CHC$_2$H$_5$)$_{17}$—R$_1$, O—(CHC$_2$H$_5$)$_{18}$—R$_1$, O—(CHC$_2$H$_5$)$_{19}$—R$_1$, O—(CHC$_2$H$_5$)$_{20}$—R$_1$, O—(CH$_2$)—(CHCH$_3$)—(CH$_2$)—R$_1$, O—(CH$_2$)—(CHCH$_3$)—(CH$_2$)$_2$—R$_1$, O—(CH$_2$)—(CHCH$_3$)—(CH$_2$)$_3$—R$_1$, O—(CH$_2$)—(CHCH$_3$)—(CH$_2$)$_{11}$—R$_1$, O—(CH$_2$)$_2$—(CHCH$_3$)—(CH$_2$)—R$_1$, O—(CH$_2$)$_3$—(CHCH$_3$)—(CH$_2$)—R$_1$, O—(CH$_2$)$_{11}$—(CHCH$_3$)—(CH$_2$)—R$_1$, O—(CH$_2$)$_2$—O—(CH$_2$)$_2$—R$_1$, O—(CH$_2$)$_3$—O—(CH$_2$)$_3$—R$_1$, O—(CH$_2$)$_2$—O—(CH$_2$)$_2$—O—(CH$_2$)$_2$—R$_1$, O—(CH$_2$)$_3$—O—(CH$_2$)$_3$—O—(CH$_2$)$_3$—R$_1$, O—(CH$_2$)$_2$—O—(CH$_2$)$_2$—O—(CH$_2$)$_6$—R$_1$, O—(CH$_2$)$_6$—O—(CH$_2$)$_2$—O—(CH$_2$)$_2$—R$_1$, O—(CH$_2$)$_2$—O—(CH$_2$)$_2$—O—(CH$_2$)$_8$—R$_1$, O—(CH$_2$)$_8$—O—(CH$_2$)$_2$—O—(CH$_2$)$_2$—R$_1$, O—(CH$_2$)$_2$—S—(CH$_2$)$_2$—R$_1$, O—(CH$_2$)$_3$—S—(CH$_2$)$_3$—R$_1$, O—(CH$_2$)$_2$—S—(CH$_2$)$_2$—S—(CH$_2$)$_2$—R$_1$, O—(CH$_2$)$_3$—S—(CH$_2$)$_3$—S—(CH$_2$)$_3$—R$_1$, O—(CH$_2$)$_2$—S—(CH$_2$)$_2$—S—(CH$_2$)$_6$—R$_1$, O—(CH$_2$)$_6$—S—(CH$_2$)$_2$—S—(CH$_2$)$_2$—R$_1$, O—(CH$_2$)$_2$—S—(CH$_2$)$_2$—S—(CH$_2$)$_8$—R$_1$, O—(CH$_2$)$_8$—S—(CH$_2$)$_2$—S—(CH$_2$)$_2$—R$_1$, O—(CH$_2$)$_2$—(NCH$_3$)—(CH$_2$)$_2$—R$_1$, O—(CH$_2$)$_3$—(NCH$_3$)—(CH$_2$)$_3$—R$_1$, O—(CH$_2$)$_2$—(NCH$_3$)—(CH$_2$)$_2$—(NCH$_3$)—(CH$_2$)$_2$—R$_1$, O—(CH$_2$)$_3$—(NCH$_3$)—(CH$_2$)$_3$—(NCH$_3$)—(CH$_2$)$_3$—R$_1$, O—(CH$_2$)$_2$—(NCH$_3$)—(CH$_2$)$_2$—(NCH$_3$)—(CH$_2$)$_6$—R$_1$, O—(CH$_2$)$_6$—(NCH$_3$)—(CH$_2$)$_2$—(NCH$_3$)—(CH$_2$)$_2$—R$_1$, O—(CH$_2$)$_2$—(NCH$_3$)—(CH$_2$)$_2$—(NCH$_3$)—(CH$_2$)$_8$—R$_1$, O—(CH$_2$)$_8$—(NCH$_3$)—(CH$_2$)$_2$—(NCH$_3$)—(CH$_2$)$_2$—R$_1$, S—(CH$_2$)—R$_1$, S—(CH$_2$)$_2$—R$_1$, S—(CH$_2$)$_3$—R$_1$, S—(CH$_2$)$_4$—R$_1$, S—(CH$_2$)$_5$—R$_1$, S—(CH$_2$)$_6$—R$_1$, S—(CH$_2$)$_7$—R$_1$, S—(CH$_2$)$_8$—R$_1$, S—(CH$_2$)$_9$—R$_1$, S—(CH$_2$)$_{10}$—R$_1$, S—(CH$_2$)$_{11}$—R$_1$, S—(CH$_2$)$_{12}$—R$_1$, S—(CH$_2$)$_{13}$—R$_1$, S—(CH$_2$)$_{14}$—R$_1$, S—(CH$_2$)$_{15}$—R$_1$, S—(CH$_2$)$_{16}$—R$_1$, S—(CH$_2$)$_{17}$—R$_1$, S—(CH$_2$)$_{18}$—R$_1$, S—(CH$_2$)$_{19}$—R$_1$, S—(CH$_2$)$_{20}$—R$_1$, S—(CHCH$_3$)—R$_1$, S—(CHCH$_3$)$_2$—R$_1$, S—(CHCH$_3$)$_3$—R$_1$, S—(CHCH$_3$)$_4$—R$_1$, S—(CHCH$_3$)$_5$—R$_1$, S—(CHCH$_3$)$_6$—R$_1$, S—(CHCH$_3$)$_7$—R$_1$, S—(CHCH$_3$)$_8$—R$_1$, S—(CHCH$_3$)$_9$—R$_1$, S—(CHCH$_3$)$_{10}$—R$_1$, S—(CHCH$_3$)$_{11}$—R$_1$, S—(CHCH$_3$)$_{12}$—R$_1$, S—(CHCH$_3$)$_{13}$—R$_1$, S—(CHCH$_3$)$_{14}$—R$_1$, S—(CHCH$_3$)$_{15}$—R$_1$, S—(CHCH$_3$)$_{16}$—R$_1$, S—(CHCH$_3$)$_{17}$—R$_1$, S—(CHCH$_3$)$_{18}$—R$_1$, S—(CHCH$_3$)$_{19}$—R$_1$, S—(CHCH$_3$)$_{20}$—R$_1$, S—(C(CH$_3$)$_2$)—R$_1$, S—(C(CH$_3$)$_2$)$_2$—R$_1$, S—(C(CH$_3$)$_2$)$_3$—R$_1$, S—(C(CH$_3$)$_2$)$_4$—R$_1$, S—(C(CH$_3$)$_2$)$_5$—R$_1$, S—(C(CH$_3$)$_2$)$_6$—R$_1$, S—(C(CH$_3$)$_2$)$_7$—R$_1$, S—(C(CH$_3$)$_2$)$_8$—R$_1$, S—(C(CH$_3$)$_2$)$_9$—R$_1$, S—(C(CH$_3$)$_2$)$_{10}$—R$_1$, S—(C(CH$_3$)$_2$)$_{11}$—

$R_1$, S—$(C(CH_3)_2)_{12}$—$R_1$, S—$(C(CH_3)_2)_{13}$—$R_1$, S—$(C(CH_3)_2)_{14}$—$R_1$, S—$(C(CH_3)_2)_{15}$—$R_1$, S—$(C(CH_3)_2)_{16}$—$R_1$, S—$(C(CH_3)_2)_{17}$—$R_1$, S—$(C(CH_3)_2)_{18}$$R_1$, S—$(C(CH_3)_2)_{19}$—$R_1$, S—$(C(CH_3)_2)_{20}$—$R_1$, S—$(CHC_2H_5)$—$R_1$, S—$(CHC_2H_5)_2$—$R_1$, S—$(CHC_2H_5)_3$—$R_1$, S—$(CHC_2H_5)_4$—$R_1$, S—$(CHC_2H_5)_5$—$R_1$, S—$(CHC_2H_5)_6$—$R_1$, S—$(CHC_2H_5)_7$—$R_1$, S—$(CHC_2H_5)_8$—$R_1$, S—$(CHC_2H_5)_9$—$R_1$, S—$(CHC_2H_5)_{10}$—$R_1$, S—$(CHC_2H_5)_{11}$—$R_1$, S—$(CHC_2H_5)_{12}$—$R_1$, S—$(CHC_2H_5)_{13}$—$R_1$, S—$(CHC_2H_5)_{14}$—$R_1$, S—$(CHC_2H_5)_{15}$—$R_1$, S—$(CHC_2H_5)_{16}$—$R_1$, S—$(CHC_2H_5)_{17}$—$R_1$, S—$(CHC_2H_5)_{18}$—$R_1$, S—$(CHC_2H_5)_{19}$—$R_1$, S—$(CHC_2H_5)_{20}$—$R_1$, S—$(CH_2)$—$(CHCH_3)$—$(CH_2)$—$R_1$, S—$(CH_2)$—$(CHCH_3)$—$(CH_2)_2$—$R_1$, S—$(CH_2)$—$(CHCH_3)$—$(CH_2)_3$—$R_1$, S—$(CH_2)$—$(CHCH_3)$—$(CH_2)_{11}$—$R_1$, S—$(CH_2)_2$—$(CHCH_3)$—$(CH_2)$—$R_1$, S—$(CH_2)_3$—$(CHCH_3)$—$(CH_2)$—$R_1$, S—$(CH_2)_{11}$—$(CHCH_3)$—$(CH_2)$—$R_1$, S—$(CH_2)_2$—O—$(CH_2)_2$—$R_1$, S—$(CH_2)_3$—O—$(CH_2)_3$—$R_1$, S—$(CH_2)_2$—O—$(CH_2)_2$—O—$(CH_2)_2$—$R_1$, S—$(CH_2)_3$—O—$(CH_2)_3$—O—$(CH_2)_3$—$R_1$, S—$(CH_2)_2$—O—$(CH_2)_2$—O—$(CH_2)_6$—$R_1$, S—$(CH_2)_6$—O—$(CH_2)_2$—O—$(CH_2)_2$—$R_1$, S—$(CH_2)_2$—O—$(CH_2)_2$—O—$(CH_2)_8$—$R_1$, S—$(CH_2)_8$—O—$(CH_2)_2$—O—$(CH_2)_2$—$R_1$, S—$(CH_2)_2$—S—$(CH_2)_2$—$R_1$, S—$(CH_2)_3$—S—$(CH_2)_3$—$R_1$, S—$(CH_2)_2$—S—$(CH_2)_2$—S—$(CH_2)_2$—$R_1$, S—$(CH_2)_3$—S—$(CH_2)_3$—S—$(CH_2)_3$—$R_1$, S—$(CH_2)_2$—S—$(CH_2)_2$—S—$(CH_2)_6$—$R_1$, S—$(CH_2)_6$—S—$(CH_2)_2$—S—$(CH_2)_2$—$R_1$, S—$(CH_2)_2$—S—$(CH_2)_2$—S—$(CH_2)_8$—$R_1$, S—$(CH_2)_8$—S—$(CH_2)_2$—S—$(CH_2)_2$—$R_1$, S—$(CH_2)_2$—$(NCH_3)$—$(CH_2)_2$—$R_1$, S—$(CH_2)_3$—$(NCH_3)$—$(CH_2)_3$—$R_1$, S—$(CH_2)_2$—$(NCH_3)$—$(CH_2)_2$—$(NCH_3)$—$(CH_2)_2$—$R_1$, S—$(CH_2)_3$—$(NCH_3)$—$(CH_2)_3$—$(NCH_3)$—$(CH_2)_3$—$R_1$, S—$(CH_2)_2$—$(NCH_3)$—$(CH_2)_2$—$(NCH_3)$—$(CH_2)_6$—$R_1$, S—$(CH_2)_6$—$(NCH_3)$—$(CH_2)_2$—$(NCH_3)$—$(CH_2)_2$—$R_1$, S—$(CH_2)_2$—$(NCH_3)$—$(CH_2)_2$—$(NCH_3)$—$(CH_2)_8$—$R_1$, S—$(CH_2)_8$—$(NCH_3)$—$(CH_2)_2$—$(NCH_3)$—$(CH_2)_2$—$R_1$, —$(CH_2)$—$R_1$, —$(CH_2)_2$—$R_1$, —$(CH_2)_3$—$R_1$, —$(CH_2)_4$—$R_1$, —$(CH_2)_5$—$R_1$, —$(CH_2)_6$—$R_1$, —$(CH_2)_7$—$R_1$, —$(CH_2)_8$—$R_1$, —$(CH_2)_9$—$R_1$, —$(CH_2)_{10}$—$R_1$, —$(CH_2)_{11}$—$R_1$, —$(CH_2)_{12}$—$R_1$, —$(CH_2)_{13}$—$R_1$, —$(CH_2)_{14}$—$R_1$, —$(CH_2)_{15}$—$R_1$, —$(CH_2)_{16}$—$R_1$, —$(CH_2)_{17}$—$R_1$, —$(CH_2)_{18}$—$R_1$, —$(CH_2)_{19}$—$R_1$, —$(CH_2)_{20}$—$R_1$, —$(CHCH_3)$—$R_1$, —$(CHCH_3)_2$—$R_1$, —$(CHCH_3)_3$—$R_1$, —$(CHCH_3)_4$—$R_1$, —$(CHCH_3)_5$—$R_1$, —$(CHCH_3)_6$—$R_1$, —$(CHCH_3)_7$—$R_1$, —$(CHCH_3)_8$—$R_1$, —$(CHCH_3)_9$—$R_1$, —$(CHCH_3)_{10}$—$R_1$, —$(CHCH_3)_{11}$—$R_1$, —$(CHCH_3)_{12}$—$R_1$, —$(CHCH_3)_{13}$—$R_1$, —$(CHCH_3)_{14}$—$R_1$, —$(CHCH_3)_{15}$—$R_1$, —$(CHCH_3)_{16}$—$R_1$, —$(CHCH_3)_{17}$—$R_1$, —$(CHCH_3)_{18}$—$R_1$, —$(CHCH_3)_{19}$—$R_1$, —$(CHCH_3)_{20}$—$R_1$, —$(C(CH_3)_2)$—$R_1$, —$(C(CH_3)_2)_2$$R_1$, —$(C(CH_3)_2)_3$—$R_1$, —$(C(CH_3)_2)_4$—$R_1$, —$(C(CH_3)_2)_5$—$R_1$, —$(C(CH_3)_2)_6$—$R_1$, —$(C(CH_3)_2)_7$—$R_1$, —$(C(CH_3)_2)_8$—$R_1$, —$(C(CH_3)_2)_9$—$R_1$, —$(C(CH_3)_2)_{10}$—$R_1$, —$(C(CH_3)_2)_{11}$—$R_1$, —$(C(CH_3)_2)_{12}$—$R_1$, —$(C(CH_3)_2)_{13}$—$R_1$, —$(C(CH_3)_2)_{14}$—$R_1$, —$(C(CH_3)_2)_{15}$—$R_1$, —$(C(CH_3)_2)_{16}$—$R_1$, —$(C(CH_3)_2)_{17}$—$R_1$, —$(C(CH_3)_2)_{18}$—$R_1$, —$(C(CH_3)_2)_{19}$—$R_1$, —$(C(CH_3)_2)_{20}$—$R_1$, —$(CHC_2H_5)$—$R_1$, —$(CHC_2H_5)_2$—$R_1$, —$(CHC_2H_5)_3$—$R_1$, —$(CHC_2H_5)_4$—$R_1$, —$(CHC_2H_5)_5$—$R_1$, —$(CHC_2H_5)_6$—$R_1$, —$(CHC_2H_5)_7$—$R_1$, —$(CHC_2H_5)_8$—$R_1$, —$(CHC_2H_5)_9$—$R_1$, —$(CHC_2H_5)_{10}$—$R_1$, —$(CHC_2H_5)_{11}$—$R_1$, —$(CHC_2H_5)_{12}$—$R_1$, —$(CHC_2H_5)_{13}$—$R_1$, —$(CHC_2H_5)_{14}$—$R_1$, —$(CHC_2H_5)_{15}$—$R_1$, —$(CHC_2H_5)_{16}$—$R_1$, —$(CHC_2H_5)_{17}$—$R_1$, —$(CHC_2H_5)_{18}$—$R_1$, —$(CHC_2H_5)_{19}$—$R_1$, —$(CHC_2H_5)_{20}$—$R_1$, —$(CH_2)$—$(CHCH_3)$—$(CH_2)$—$R_1$, —$(CH_2)$—$(CHCH_3)$—$(CH_2)_2$—$R_1$, —$(CH_2)$—$(CHCH_3)$—$(CH_2)_3$—$R_1$, —$(CH_2)$—$(CHCH_3)$—$(CH_2)_{11}$—$R_1$, —$(CH_2)_2$—$(CHCH_3)$—$(CH_2)$—$R_1$, —$(CH_2)_3$—$(CHCH_3)$—$(CH_2)$—$R_1$, —$(CH_2)_{11}$—$(CHCH_3)$—$(CH_2)$—$R_1$, —$(CH_2)_2$—O—$(CH_2)_2$—$R_1$, —$(CH_2)_3$—O—$(CH_2)_3$—$R_1$, —$(CH_2)_2$—O—$(CH_2)_2$—O—$(CH_2)_2$—$R_1$, —$(CH_2)_3$—O—$(CH_2)_3$—O—$(CH_2)_3$—$R_1$, —$(CH_2)_2$—O—$(CH_2)_2$—O—$(CH_2)_6$—$R_1$, —$(CH_2)_6$—O—$(CH_2)_2$—O—$(CH_2)_2$—$R_1$, —$(CH_2)_2$—O—$(CH_2)_2$—O—$(CH_2)_8$—$R_1$, —$(CH_2)_8$—O—$(CH_2)_2$—O—$(CH_2)_2$—$R_1$, —$(CH_2)_2$—S—$(CH_2)_2$—$R_1$, —$(CH_2)_3$—S—$(CH_2)_3$—$R_1$, —$(CH_2)_2$—S—$(CH_2)_2$—S—$(CH_2)_2$—$R_1$, —$(CH_2)_3$—S—$(CH_2)_3$—S—$(CH_2)_3$—$R_1$, —$(CH_2)_2$—S—$(CH_2)_2$—S—$(CH_2)_6$—$R_1$, —$(CH_2)_6$—S—$(CH_2)_2$—S—$(CH_2)_2$—$R_1$, —$(CH_2)_2$—S—$(CH_2)_2$—S—$(CH_2)_8$—$R_1$, —$(CH_2)_8$—S—$(CH_2)_2$—S—$(CH_2)_2$—$R_1$, —$(CH_2)_2$—$(NCH_3)$—$(CH_2)_2$—$R_1$, —$(CH_2)_3$—$(NCH_3)$—$(CH_2)_3$—$R_1$, —$(CH_2)_2$—$(NCH_3)$—$(CH_2)_2$—$(NCH_3)$—$(CH_2)_2$—$R_1$, —$(CH_2)_3$—$(NCH_3)$—$(CH_2)_3$—$(NCH_3)$—$(CH_2)_3$—$R_1$, —$(CH_2)_2$—$(NCH_3)$—$(CH_2)_2$—$(NCH_3)$—$(CH_2)_6$—$R_1$, —$(CH_2)_6$—$(NCH_3)$—$(CH_2)_2$—$(NCH_3)$—$(CH_2)_2$—$R_1$, —$(CH_2)_2$—$(NCH_3)$—$(CH_2)_2$—$(NCH_3)$—$(CH_2)_8$—$R_1$ and —$(CH_2)_8$—$(NCH_3)$—$(CH_2)_2$—$(NCH_3)$—$(CH_2)_2$—$R_1$, wherein $R_1$ is a polymerizable group selected from the group consisting of a trialkoxysilyl group, a dialkoxyalkylsilyl group, a silyl group of formula (6), (7) or (8) as described before where the alkyl and/or alkoxy groups are each independently linear or branched having 1 to 6 C atoms, or an alkenyl group of formula (5),

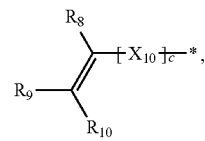

(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1.

Preferably, $R_9$ and $R_{10}$ are H.
Preferably, $R_8$ is H, methyl, ethyl or phenyl.
Preferably, $X_{10}$ is C(=O) or C(=O)O.

Preferred alkenyl groups of formula (5) are therefore represented by any one selected from the group consisting of formulae (5-1), (5-2), (5-3), (5-4), (5-5), (5-6), (5-7), (5-8), and (5-9):

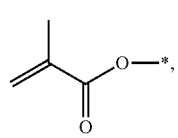

(5-1)

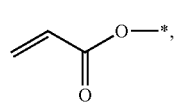

(5-2)

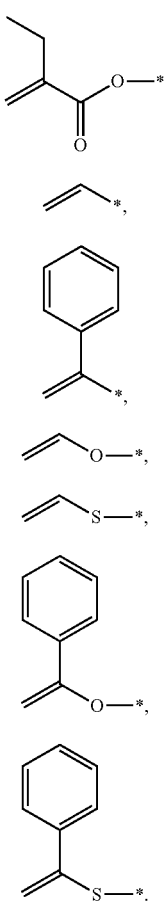

(5-3)
(5-4)
(5-5)
(5-6)
(5-7)
(5-8)
(5-9)

The alkenyl group represented by formula (5-1) is called methacrylate. The alkenyl group represented by formula (5-2) is called acrylate.

The preferred groups $R_1$ are preferably combined with preferred groups of the linking element $—R_2—$ and/or the linking element $Y—R_2—$. Combinations are excluded where two O atoms or one O atom and one S atom are directly bonded to each other as known for a skilled artisan in the field of organic chemistry.

The substituent $Y—R_2—R_1$ is therefore particularly preferably selected from the group consisting of $O—(CH_2)_8—R_1$, $O—(CH_2)_{11}—R_1$, $O—(CH_2)_{12}—R_1$ and $O—(CH_2)_{13}—R_1$ wherein $R_1$ is selected from the group consisting of triethoxysilyl, diethoxymethylsilyl or an alkenyl of formula (5-1), (5-2), (5-3), (5-4), (5-5), (5-6), (5-7), (5-8), or (5-9);

$—(CH_2)_8—R_1$, $—(CH_2)_{11}—R_1$, $—(CH_2)_{12}—R_1$ and $—(CH_2)_{13}—R_1$ wherein $R_1$ is selected from the group consisting of triethoxysilyl, diethoxymethylsilyl or an alkenyl of formula (5-1), (5-2), (5-3), (5-4), (5-5), (5-6), (5-7), (5-8), or (5-9);

and $S—(CH_2)_8—R_1$, $S—(CH_2)_{11}—R_1$, $S—(CH_2)_{12}—R_1$ and $S—(CH_2)_{13}—R_1$ wherein $R_1$ is selected from the group consisting of triethoxysilyl, diethoxymethylsilyl or an alkenyl of formula (5-1), (5-2), (5-3), (5-4), (5-5), (5-6), (5-7), (5-8), or (5-9).

Very particularly preferably, the compounds of formula (I), (I'), (I'') and (I''') comprise a polymerizable group $R_1$ which is a methacryl or an acryl group represented by formula (5-1) and (5-2).

The invention therefore relates further to compounds of formula (I), (I'), (I'') and/or (I''') as described before or preferably described before wherein $R_1$ is at each occurrence independently an acryl or methacryl group.

Examples for compounds of formula (I), (I'), (I'') and/or (I''') are the following compounds O-01 to O-127 and N-01 to N-14:

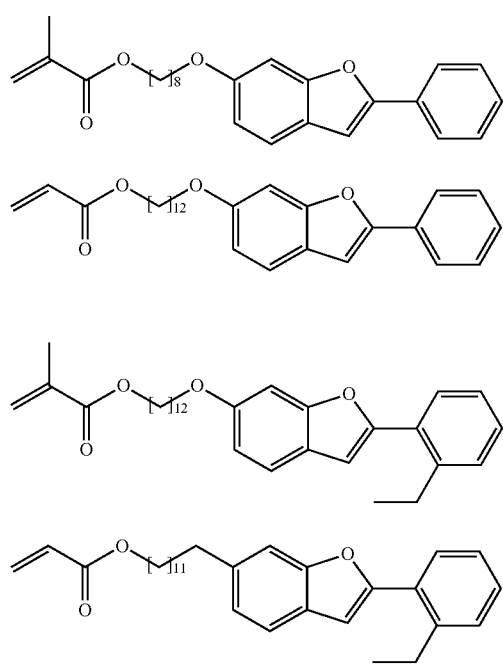

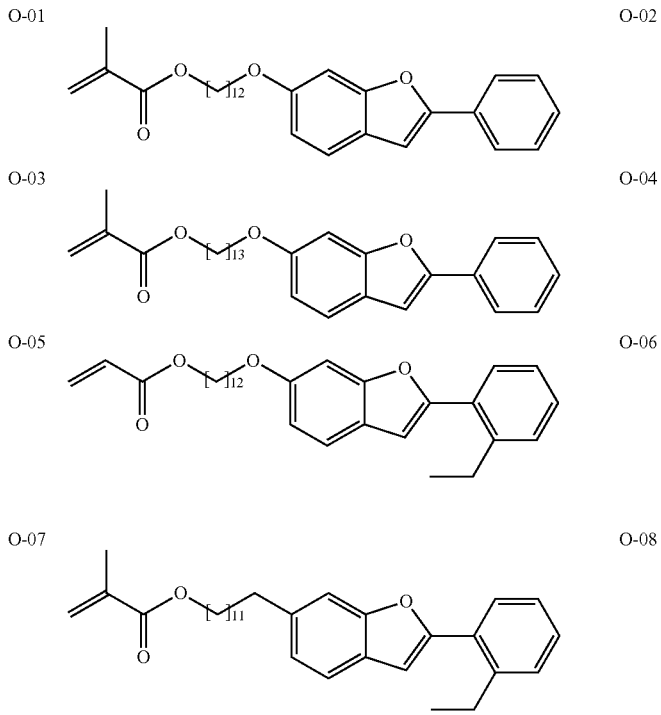

-continued
O-09
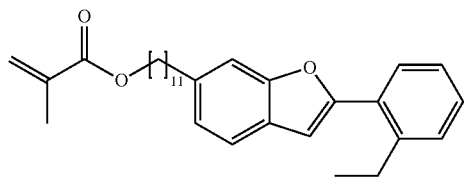
O-10
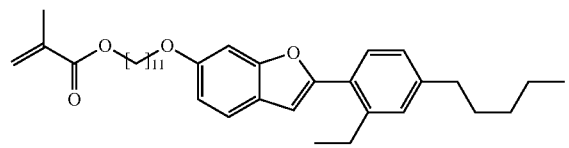
O-11
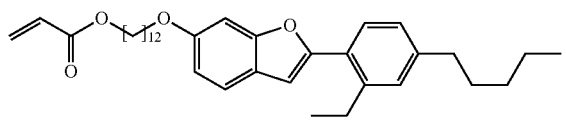
O-12
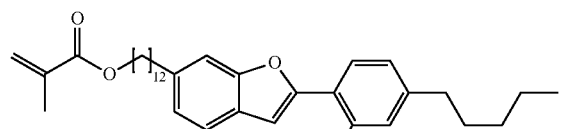
O-13
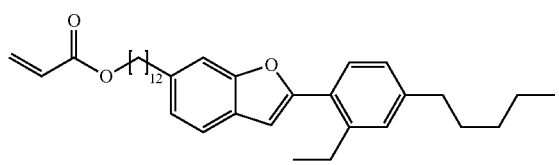
O-14
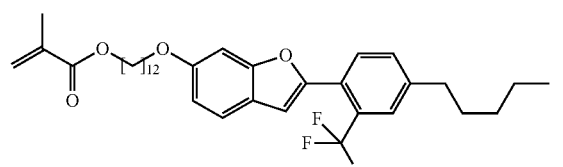
O-15
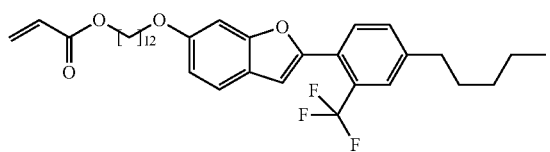
O-16
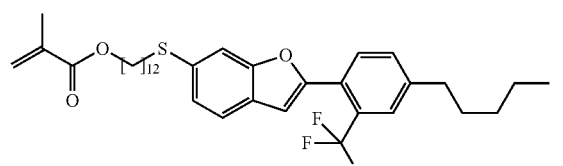
O-17
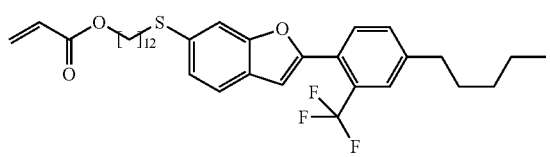
O-18
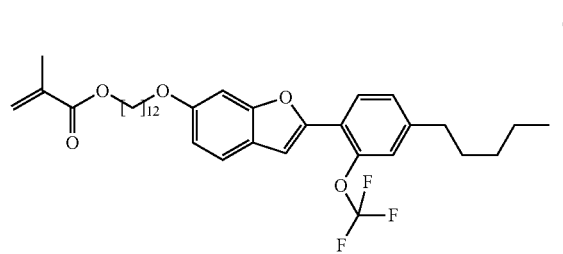
O-19
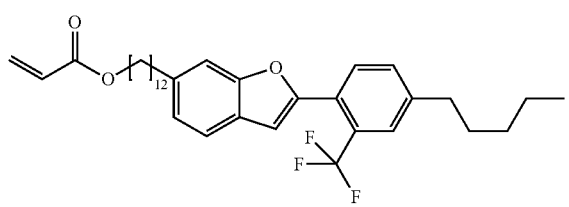
O-20
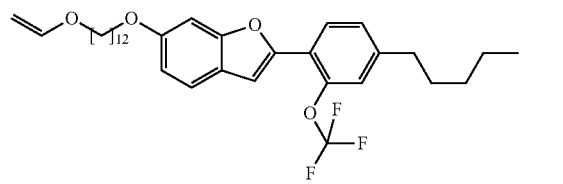
O-21
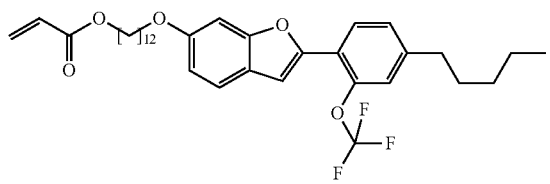
O-22

-continued
O-23
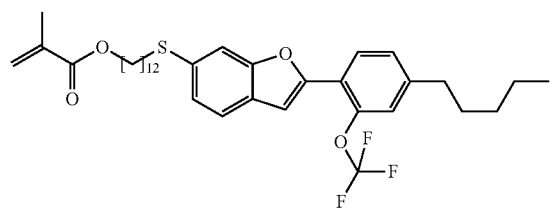
O-24
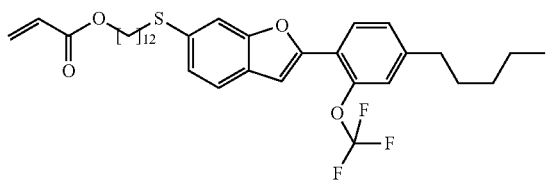
O-25
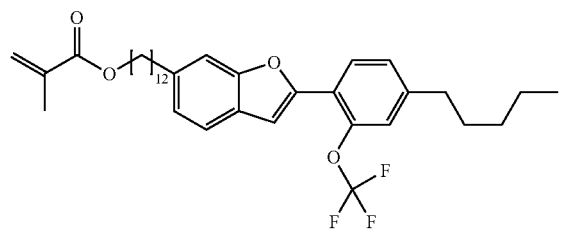
O-26
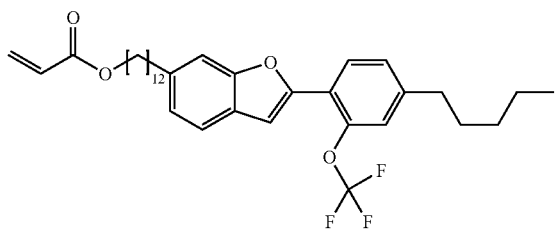
O-27
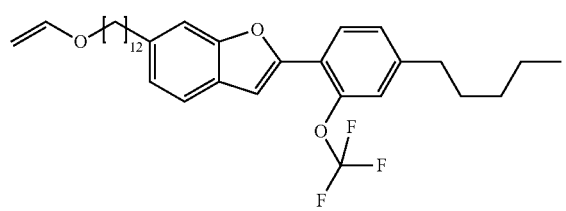
O-28
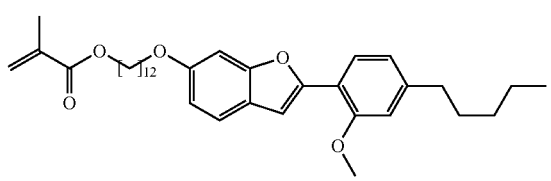
O-29
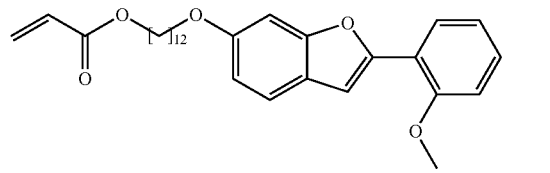
O-30
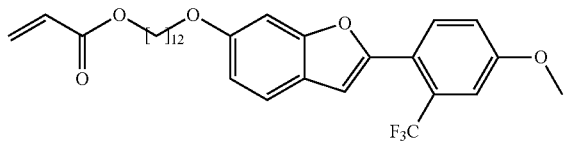
O-31
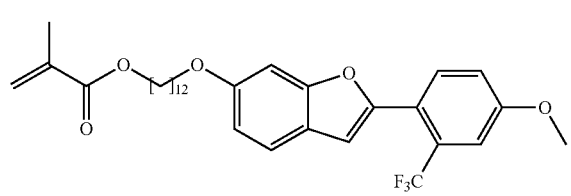
O-32
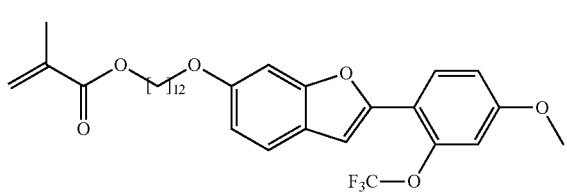
O-33
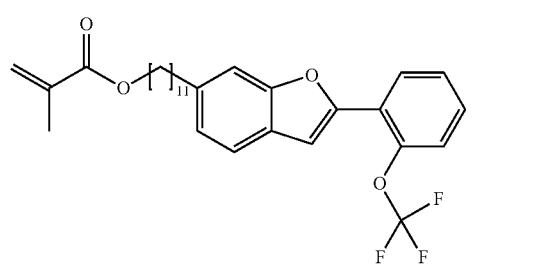
O-34
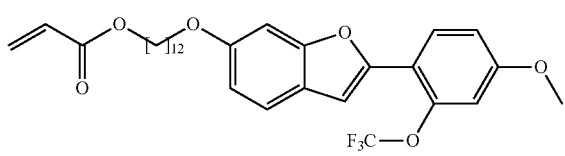
O-35
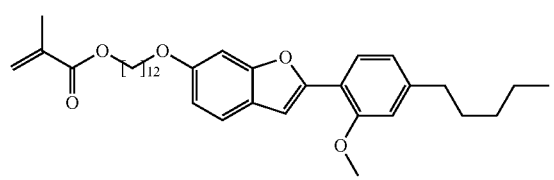
O-36
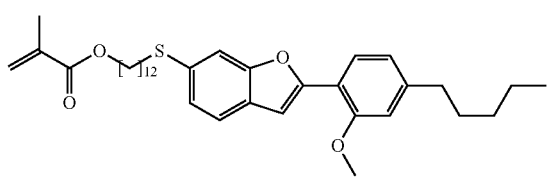

-continued
O-37
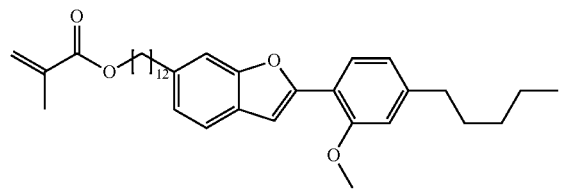
O-38
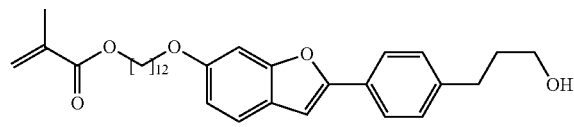
O-39
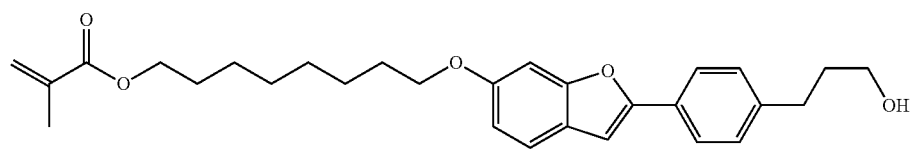
O-40
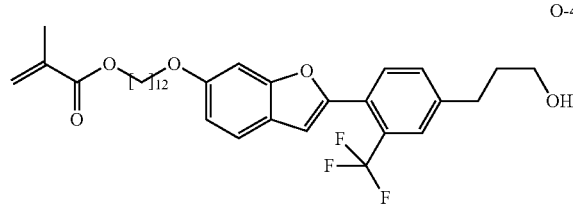
O-41
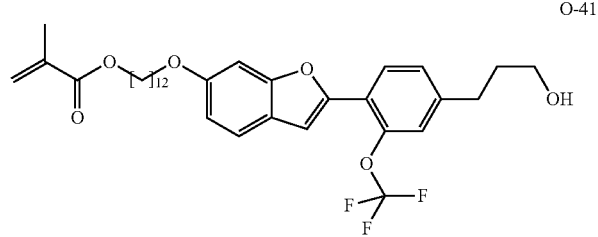
O-42
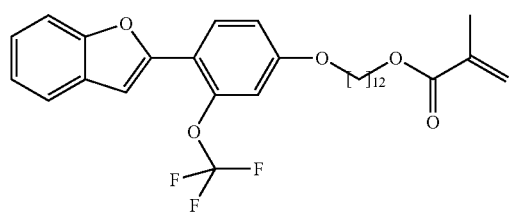
O-43
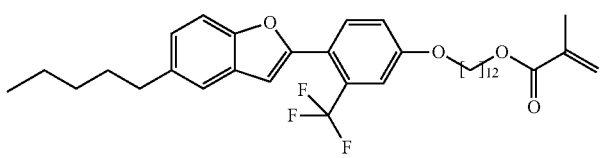
O-44
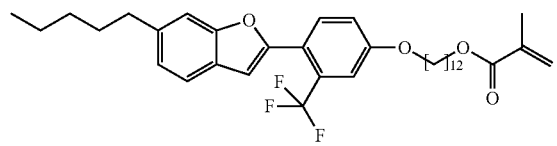
O-45
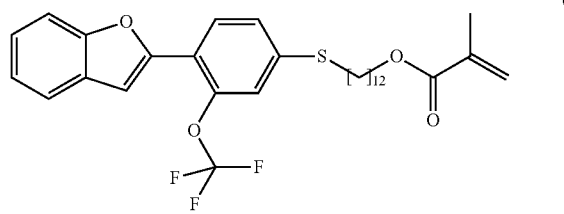
O-46
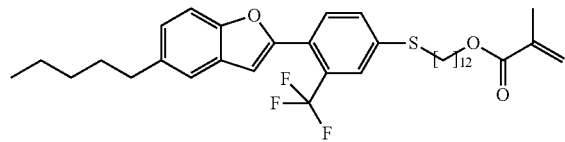
O-47
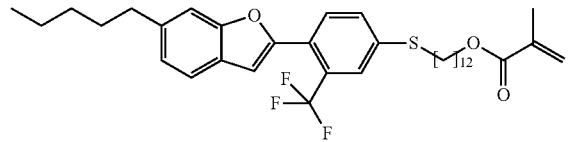
O-48
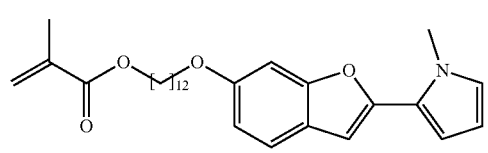
O-49
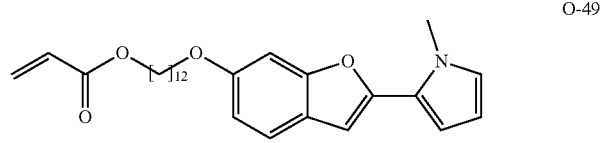

-continued
O-50
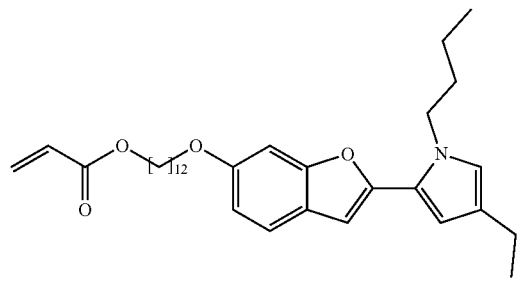
O-51
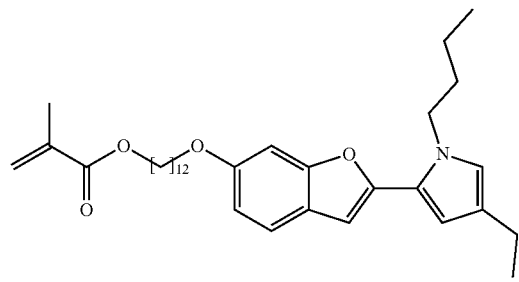
O-52
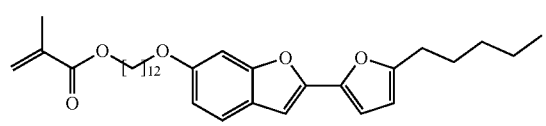
O-53
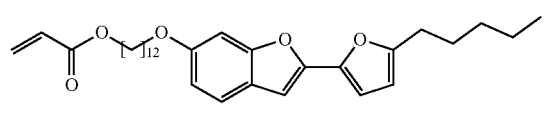
O-54
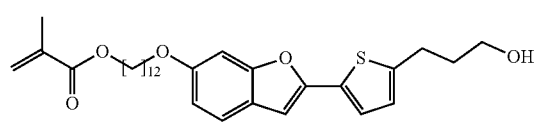
O-55
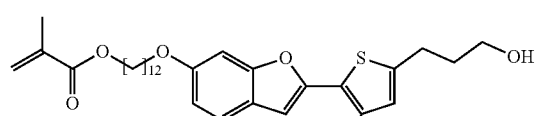
O-56
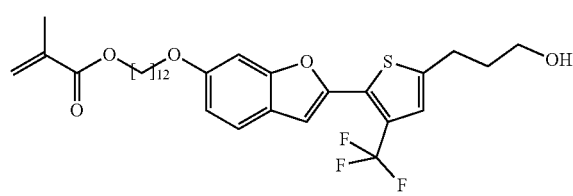
O-57
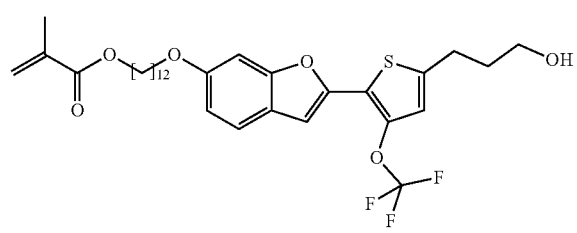
O-58
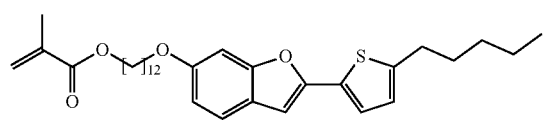
O-59
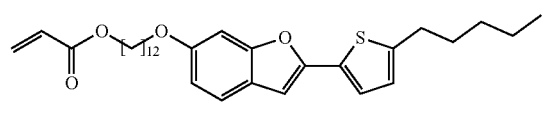
O-60
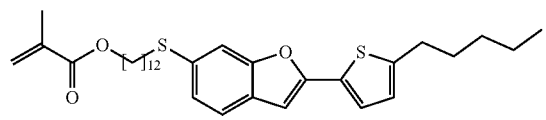
O-61
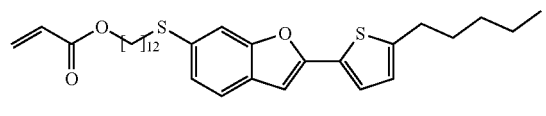
O-62
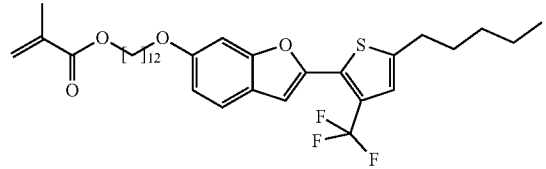
O-63
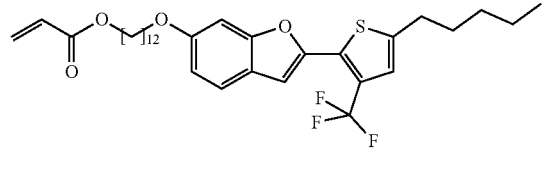
O-64
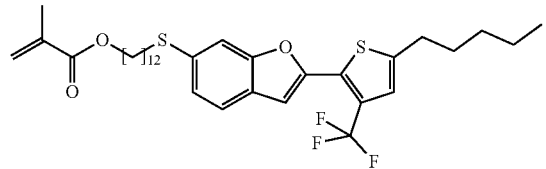
O-65
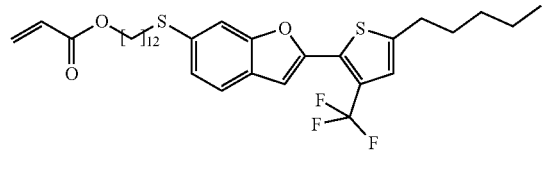

-continued
O-66
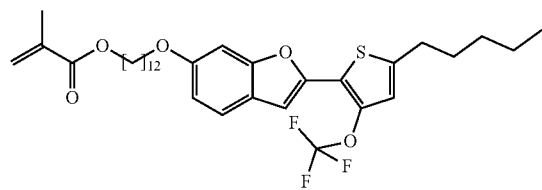
O-67
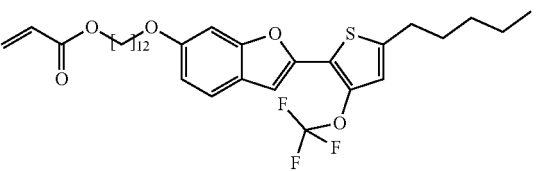
O-68
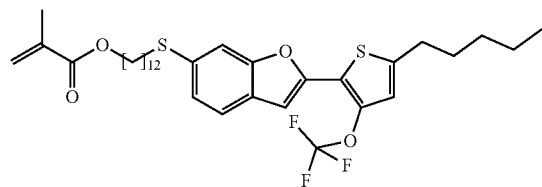
O-69
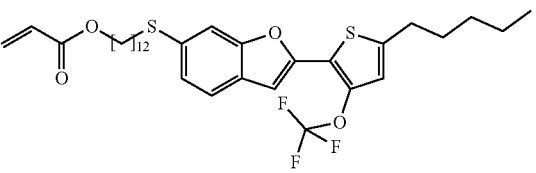
O-70
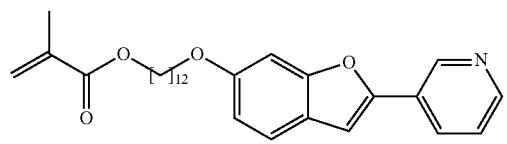
O-71
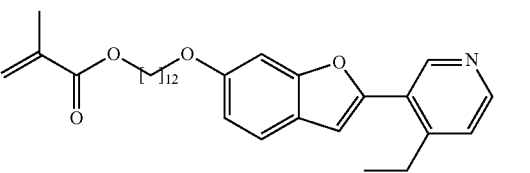
O-72
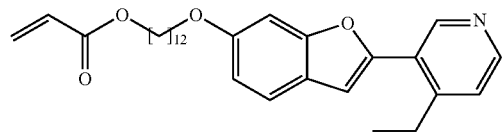
O-73
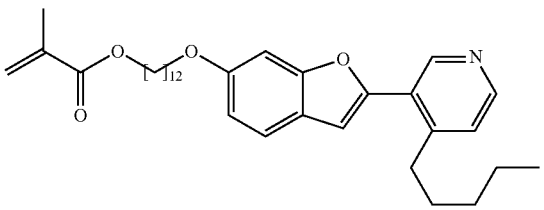
O-74
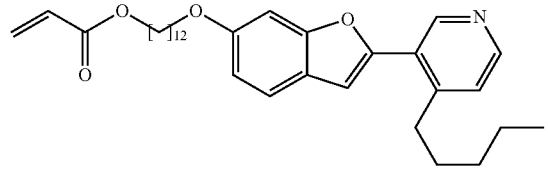
O-75
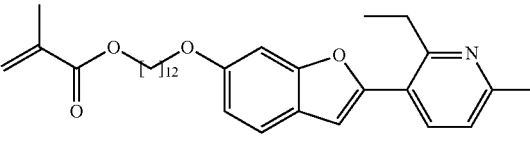
O-76
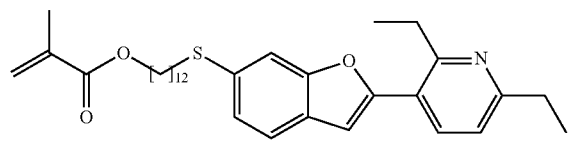
O-77
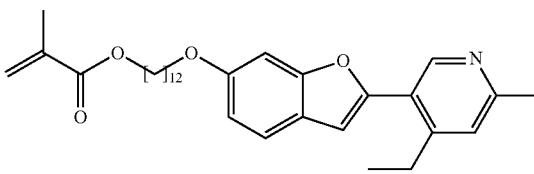
O-78
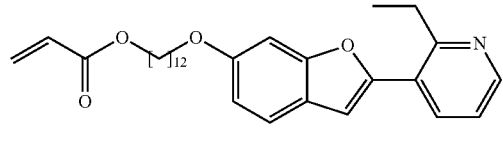
O-79
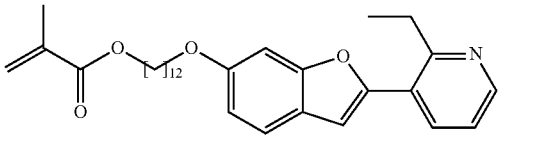
O-80
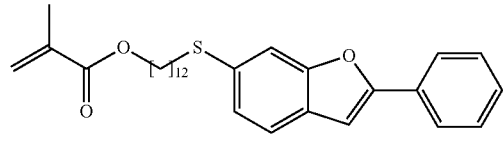
O-81
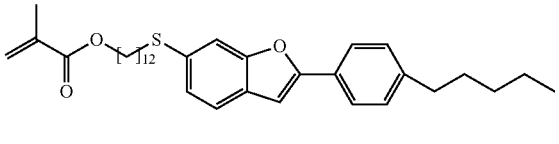

-continued
O-82
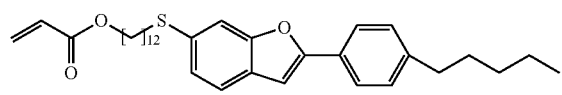
O-83
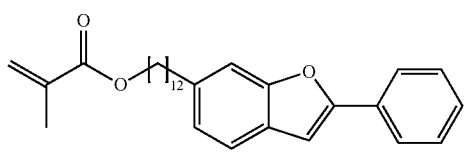
O-84
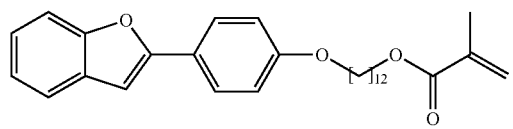
O-85
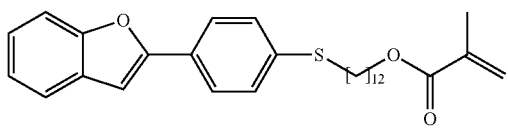
O-86
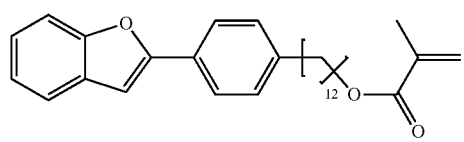
O-87
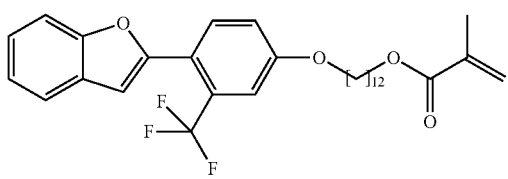
O-88
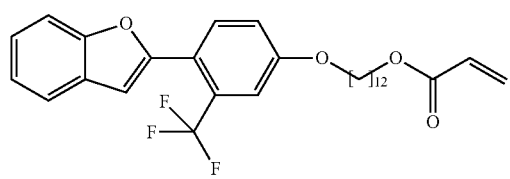
O-89
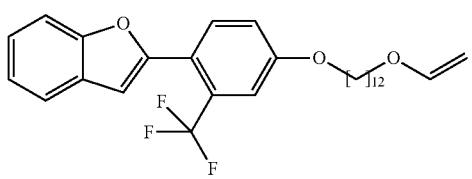
O-90
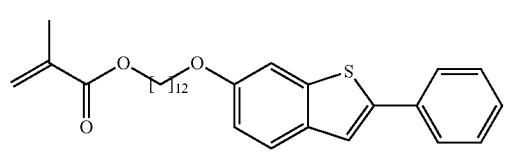
O-91
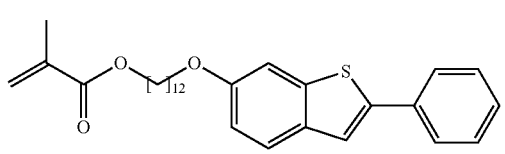
O-92
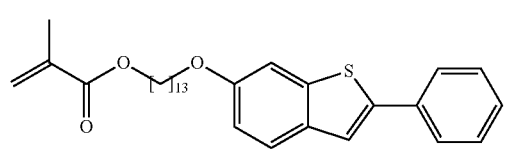
O-93
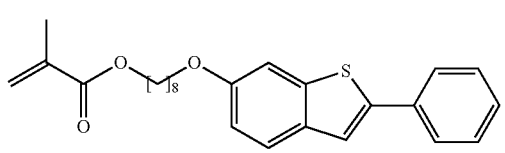
O-94
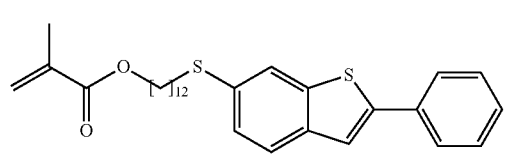
O-95
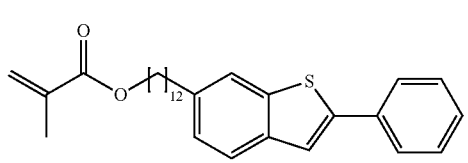
O-96
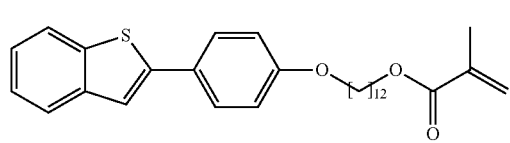
O-97
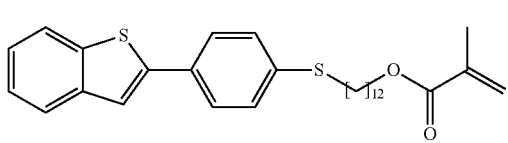
O-98
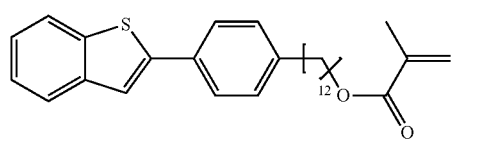
O-99
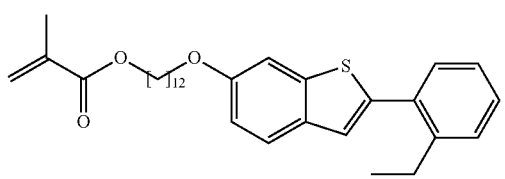
O-100
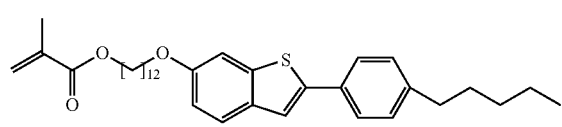
O-101
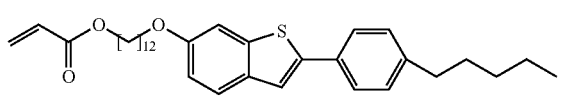

-continued
O-102
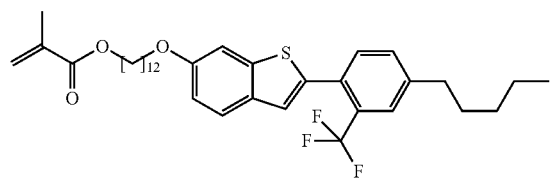
O-103
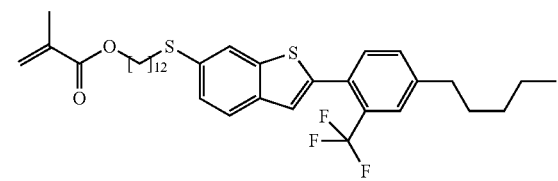
O-104
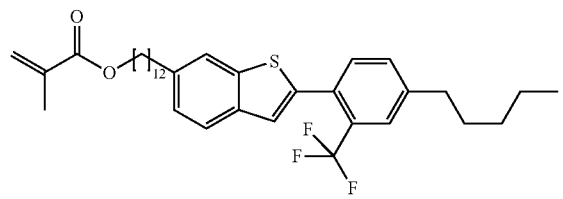
O-105
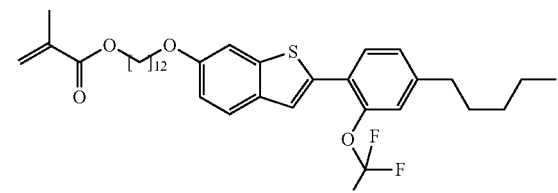
O-106
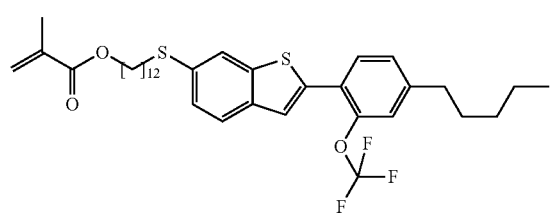
O-107
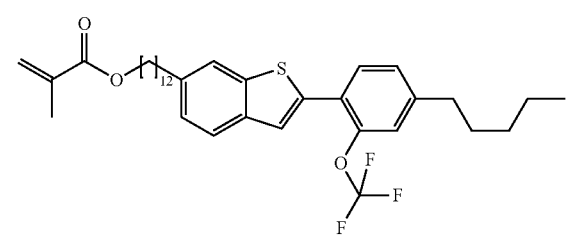
O-108
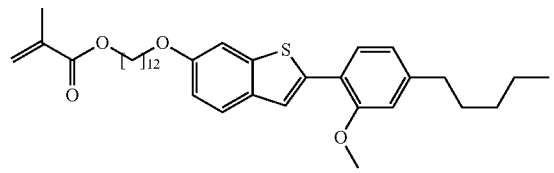
O-109
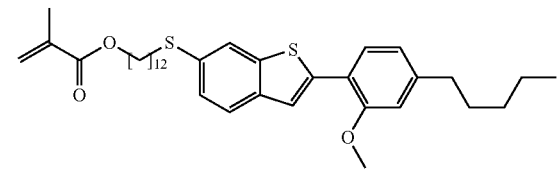
O-110
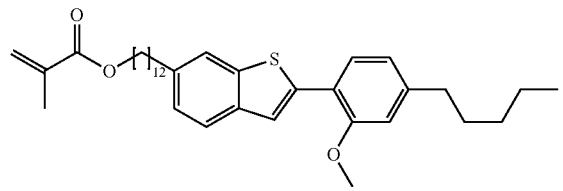
O-111
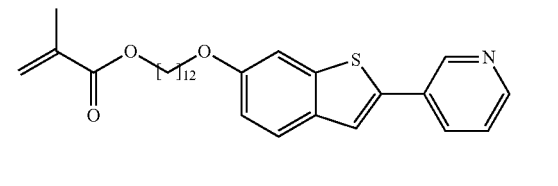
O-112
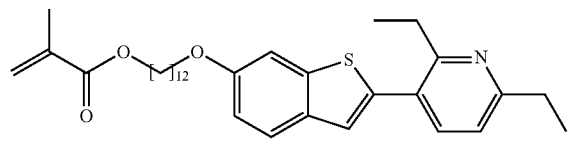
O-113
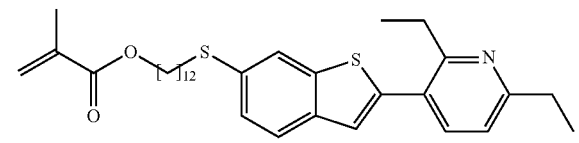
O-114
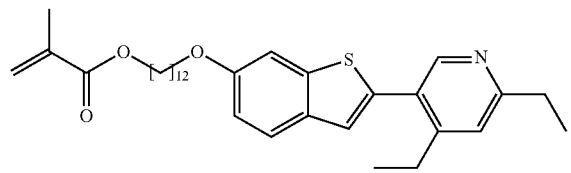
O-115
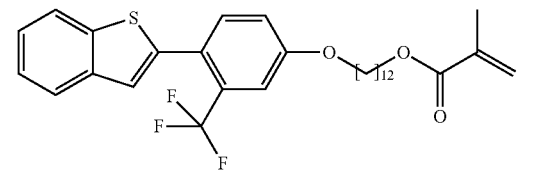

-continued
O-116
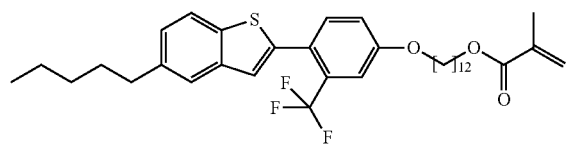
O-117
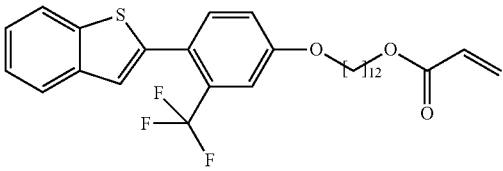
O-118
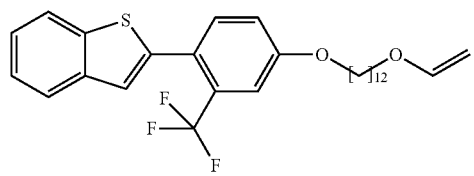
O-119
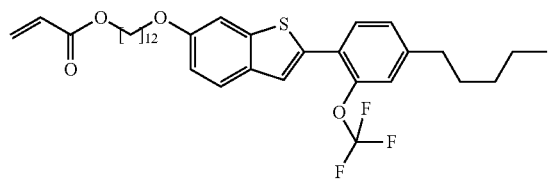
O-120
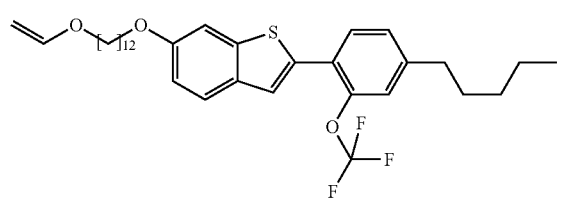
O-121
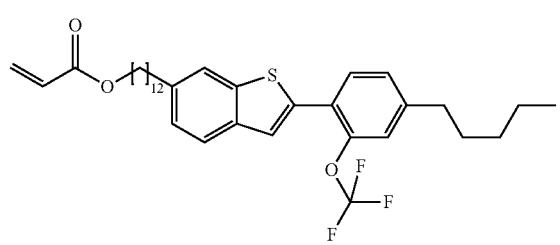
O-122
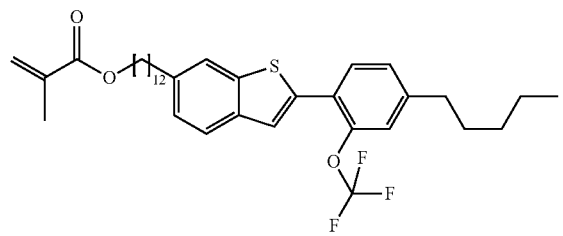
O-123
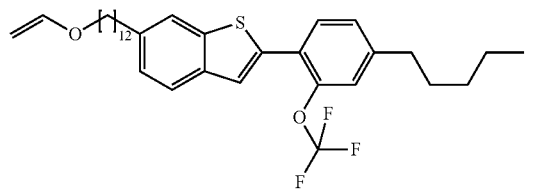
O-124
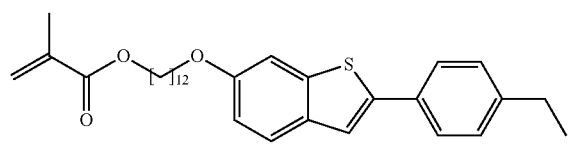
O-125
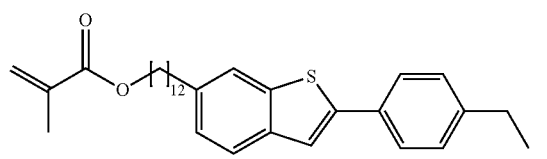
O-126
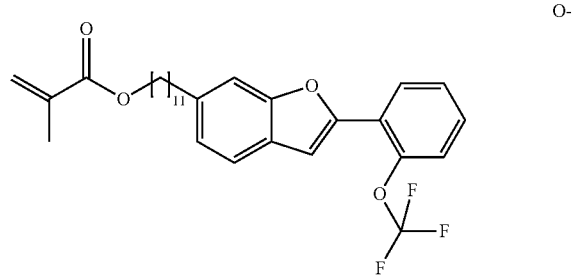
O-127
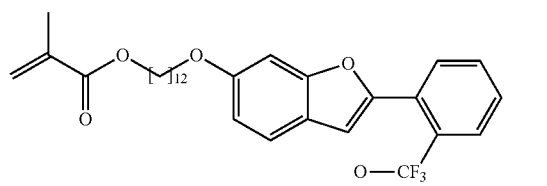
N-01
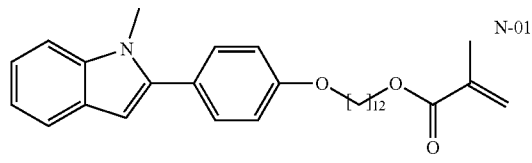
N-02
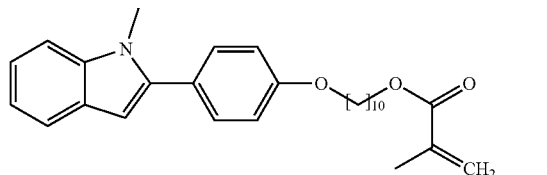

N-03
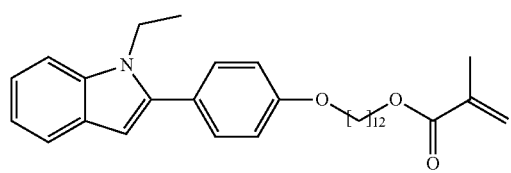
N-04
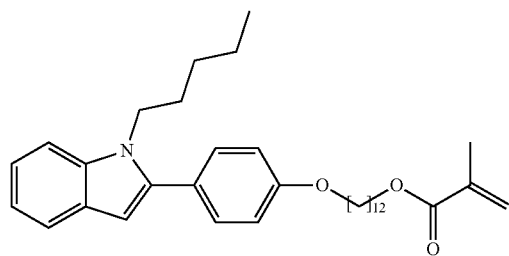
N-05
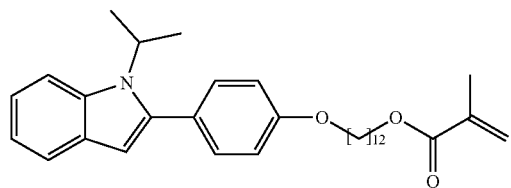
N-06
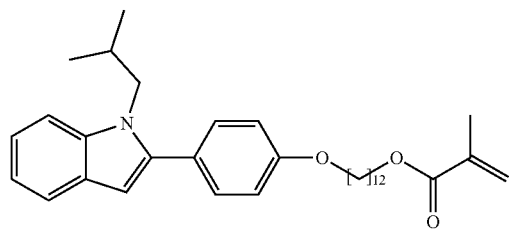
N-07
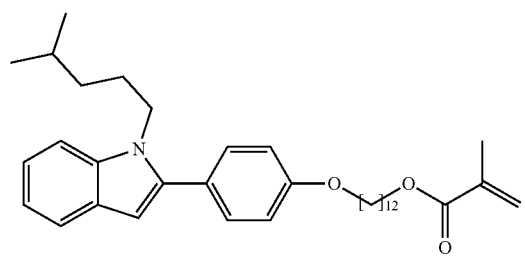
N-08
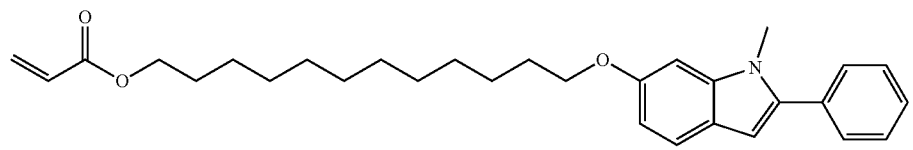
N-09
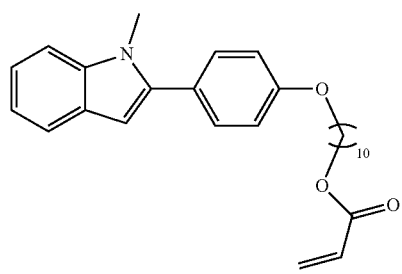
N-10
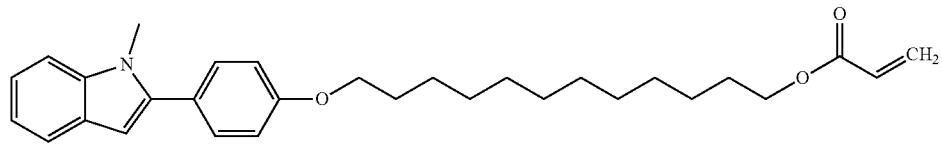
N-11
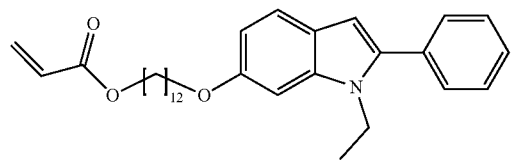
N-12
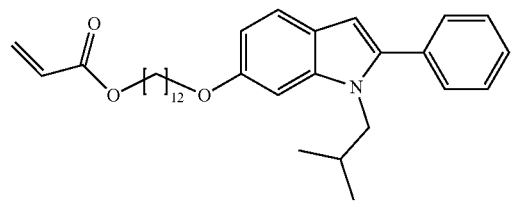

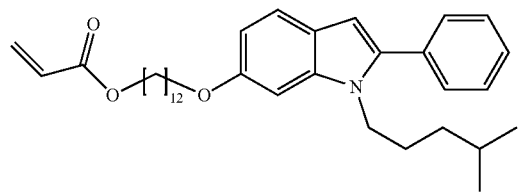

N-13

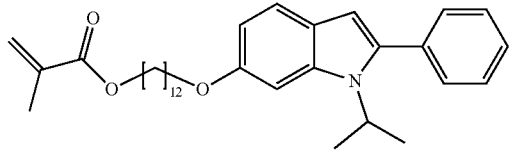

N-14

The compounds of the present application may be synthesized by methods well known to the skilled person. Preferably, all syntheses are carried out under an inert atmosphere using dried solvents. An exemplary reaction sequence is shown in Scheme 1 for the compound O-22.

The first type of reaction is a classic aldol-addition with subsequent decarboxylation.

The second type of reaction is a Palladium catalyzed Suzuki reaction.

Scheme 1

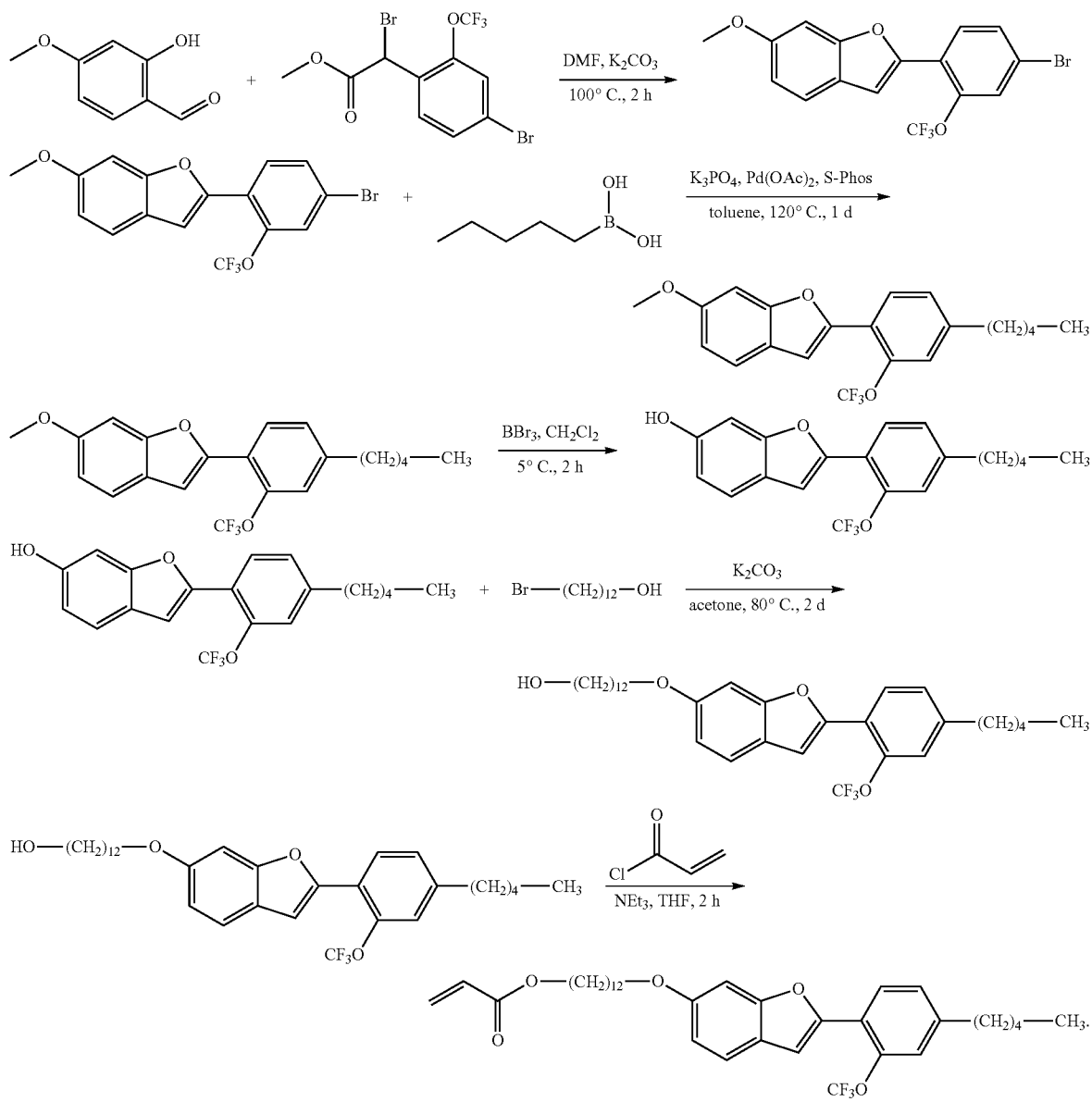

The third type of reaction is an ether cleavage in the presence of borontribromide.

The fourth type of reaction is a Williamson ether synthesis.

The fifth type of reaction is an esterification reaction.

All these types of reaction and their reaction conditions are well known to a skilled person and can be easily optimized for the specific starting materials forming the compounds of formula (I). More details can be found in the experimental section.

An exemplary reaction sequence is shown in Scheme 2 for the compound O-104.

Scheme 2

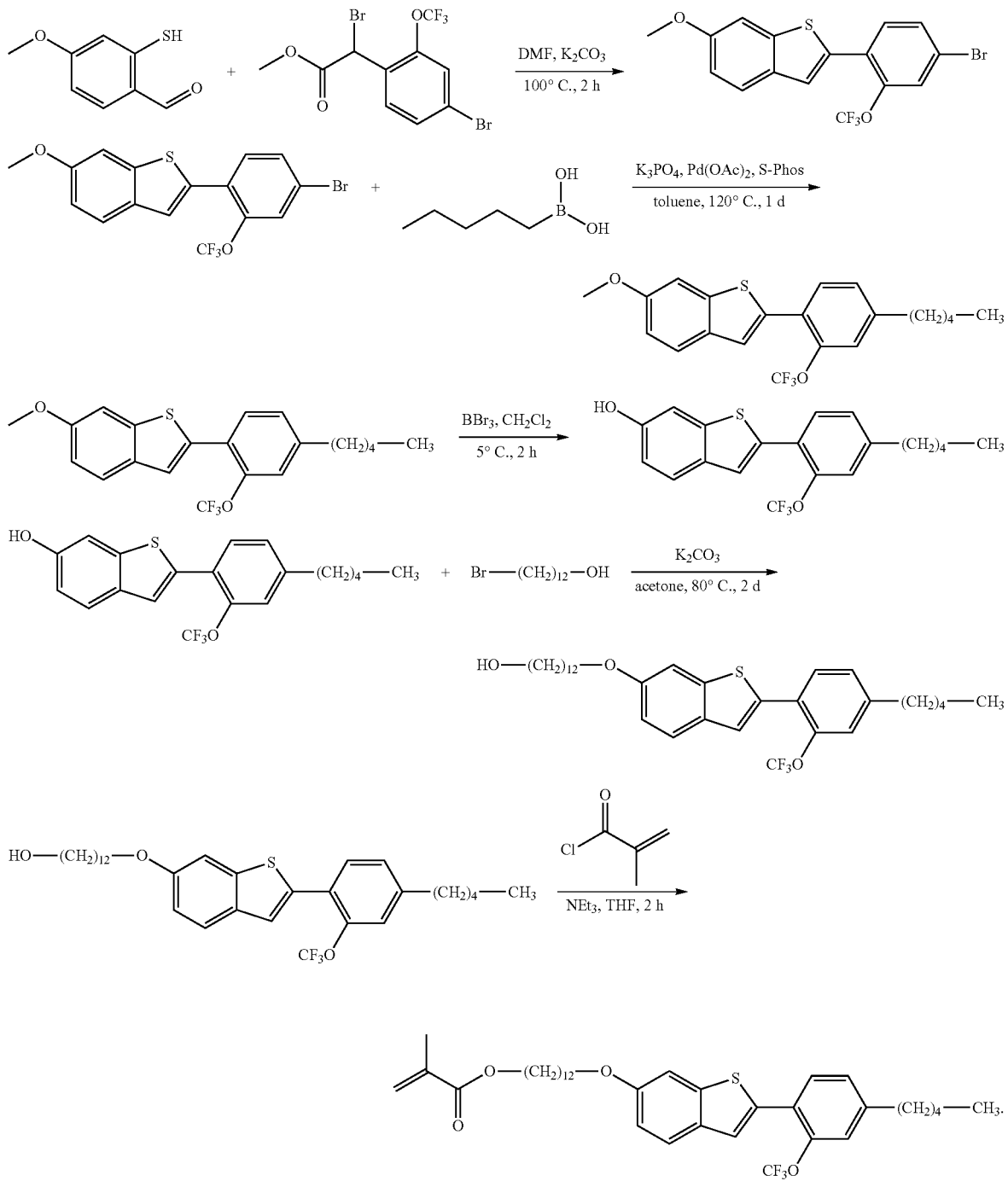

O-104

The same types of reactions apply for scheme 2 as described for scheme 1.

An exemplary reaction sequence is shown in Scheme 3 for the compound N-08.

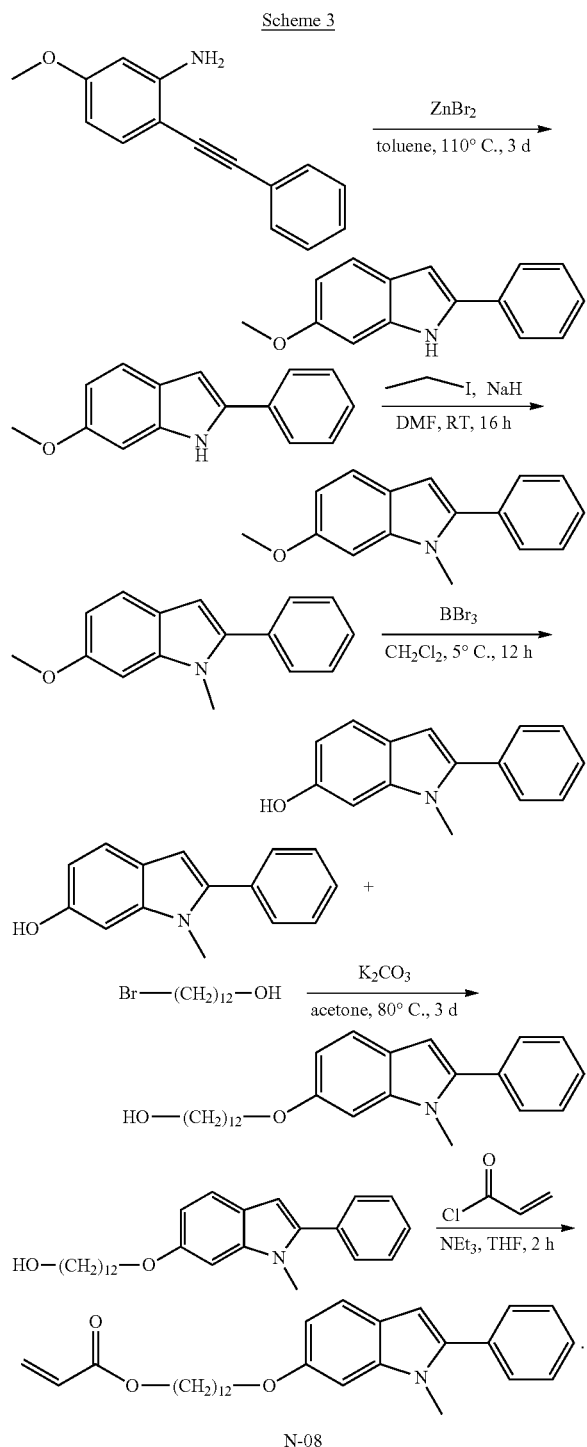

The first type of reaction is a ring closure in the presence of Zinc bromide. In the third step, an alkyl group on the N atom is introduced via alkyl iodide. The third type of reaction is an ether cleavage in the presence of borontribromide. The fourth type of reaction is a Williamson ether synthesis. The fifth type of reaction is an esterification reaction.

All these types of reaction and their reaction conditions are well known to a skilled person and can be easily optimized for the specific starting materials forming the compounds of formula (I). More details can be found in the experimental section.

As described before, the compounds of formula (I), (I'), (I") and/or (I''') as described before or preferably described before contain a polymerizable group and are predestinated as monomers for an oligomerization or a polymerization.

The invention is therefore further directed to an oligomer or polymer comprising polymerized compounds of formula (I), (I'), (I") and/or (I''') as described before or preferably described before.

The term "polymer" generally means a molecule of high relative molecular mass, the structure of which essentially comprises the multiple repetition of units derived, actually or conceptually, from molecules of low relative molecular mass (PAC, 1996, 68, 2291). The term "polymer" includes homopolymers and co-polymers. The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having ≥30 repeating units, and an oligomer means a compound with >1 and <30 repeating units.

Above and below, in formulae showing a polymer, an oligomer, a compound of formula (I) or a monomeric unit formed from a compound of formula (I), an asterisk ("*") denotes a linkage to the adjacent repeating unit in the polymer chain or oligomer chain or to a terminal end group.

Suitable terminal end groups are known to the skilled artisan and depend on the polymerization method used.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

Unless stated otherwise, the molecular weight is given as the number average molecular weight $M_n$ or weight average molecular weight Mw, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, tetrahydrofuran is used as solvent. The degree of polymerization (n) means the number average degree of polymerization given as $n=M_n/M_U$, wherein $M_U$ is the molecular weight of the single repeating unit as described in J. M. G. Cowie, *Polymers: Chemistry & Physics of Modern Materials*, Blackie, Glasgow, 1991.

In the polymers according to the the present invention, the total number of repeating units n is preferably ≥30, very preferably ≥100, most preferably ≥200, and preferably up to 5000, very preferably up to 3000, most preferably up to 2000, including any combination of the aforementioned lower and upper limits of n.

The polymers of the present invention include homopolymers, statistical co-polymers, random co-polymers, alternating co-polymers and block co-polymers, and combinations of the aforementioned.

Throughout the description and claims of this specification, the words "comprise" and "contain" and variations of the words, for example "comprising" and "comprises", mean "including but not limited to", and are not intended to (and do not) exclude other components.

Preferably the polymerizable group $R_1$ forms the regioregular, alternated, regiorandom, statistical, block or random homopolymer or co-polymer backbone or is part of the polymer backbone where $R_1$ has a meaning as described or preferably described before. Particularly preferably, such oligomer or polymer comprises a constitutional unit $M^0$ of formulae (5-p-1), (5-p-2), (5-p-3),

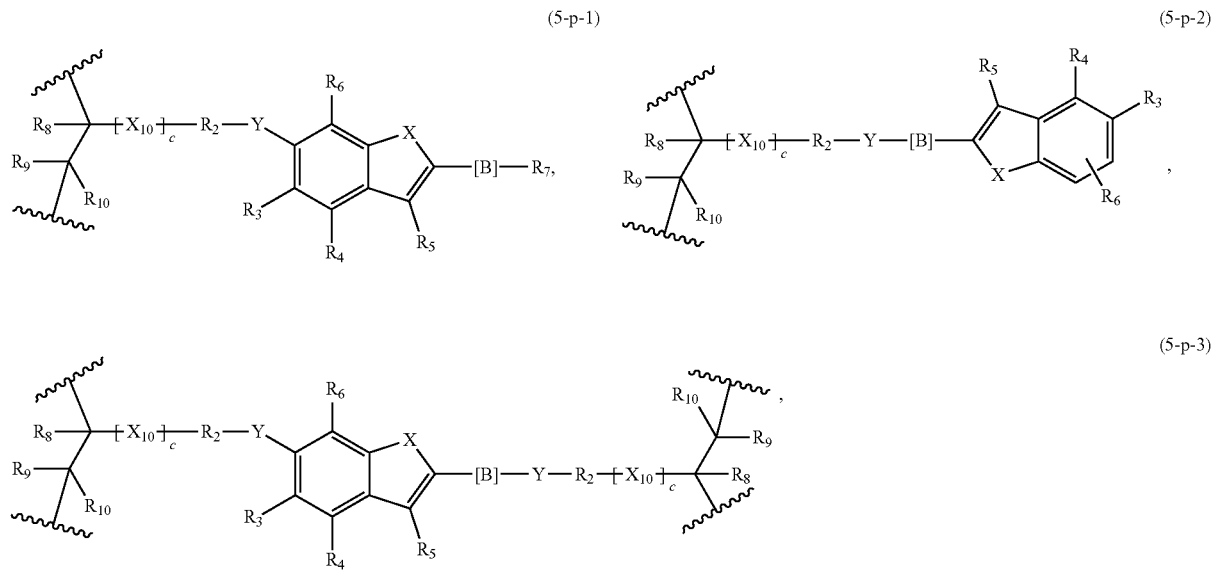

wherein
—$R_2$—, Y, $R_3$, $R_4$, $R_5$, $R_6$, X, —[B]—, $R_7$, $X_{10}$, $R_8$, $R_9$, $R_{10}$ and c have a meaning or a preferred meaning as described or preferably described before. Combinations are excluded where two O atoms or an O atom and a S atom are directly linked to each other as known for a skilled artisan in the field of organic chemistry.

The co-polymer may be an oligomer or polymer comprising one or more polymerized compounds of formula (I), (I'), (I''') or (I'''') or a constitutional unit $M^0$ of formulae (5-p-1), (5-p-2), (5-p-3), which may be the same or different from one another, and one or more constitutional units $M^2$, which may be the same or different from one another.

Said one or more constitutional units $M^2$ are chemically different from the units $M^0$. Preferably, said one or more constitutional units $M^2$ are derived by polymerization of one or more monomers selected from the group consisting of styrene, ethoxyethyl methacrylate (EOEMA), methyl methacrylate (MMA), n-alkyl methacrylates (the n-alkyl groups comprising 2-20 C-atoms), n-alkyl methacrylates (the n-alkyl groups comprising 2-20 C-atoms), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), Bisphenol A diacrylate-1 EO/Phenol (BPADA), 2-[3'-2'H-benzotriazol-2'-yl)-4'-hydroxyphenyl]ethyl methacrylate (BTPEM), trialkoxyalkenylsilane, dialkoxyalkylalkenylsilane or a silane of formula (9) and (10),

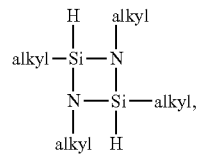

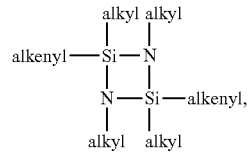

where the alkyl and/or alkoxy groups are at each occurrence independently of each other linear or branched having 1 to 6 C atoms and where the alkenyl group is at each occurrence independently linear having 2 to 4 C atoms.

Particularly preferably, said one or more constitutional units $M^2$ are derived by polymerization of one or more monomers selected from the group consisting of styrene, ethoxyethyl methacrylate (EOEMA), methyl methacrylate (MMA), n-alkyl methacrylates (the n-alkyl groups comprising 2-20 C-atoms), n-alkyl methacrylates (the n-alkyl groups comprising 2-20 C-atoms), ethoxyethyl methacrylate (EOEMA), methyl methacrylate (MMA), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), Bisphenol A diacrylate-1 EO/Phenol (BPADA) and 2-[3'-2'H-benzotriazol-2'-yl)-4'-hydroxyphenyl]ethyl methacrylate (BTPEM) in combination with inventive monomers containing an alkenyl group of formula (5) as described or preferably described before.

Particularly preferably, said one or more constitutional units $M^2$ are derived by polymerization of one or more monomers selected from the group consisting of trialkoxyalkenylsilane, dialkoxyalkylalkenylsilane or a silane of formula (9) and (10),

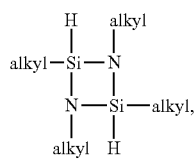
(9)

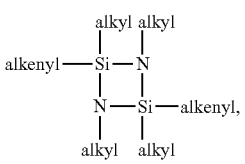
(10)

where the alkyl and/or alkoxy groups are at each occurrence independently of each other linear or branched having 1 to 6 C atoms and where the alkenyl group is at each occurrence independently linear having 2 to 4 C atoms in combination with inventive monomers containing a polymerizable group containing at least one Si atom.

Alternatively the oligomer or polymer according to the invention is a homopolymer, i.e. an oligomer or polymer comprising one or more constitutional unit $M^o$ of formula of formulae (5-p-1), (5-p-2), (5-p-3), wherein all constitutional units $M^o$ are the same.

Exemplary polymeric compounds may be selected from the following formulae (P-01) to (P-161):

P-01

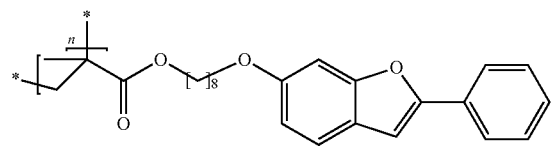

P-02

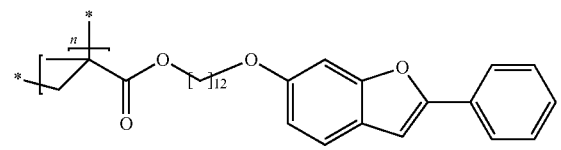

P-03

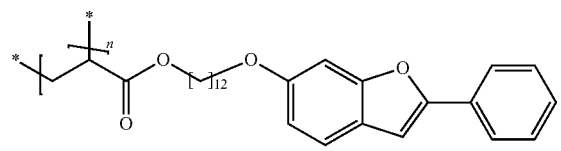

P-04

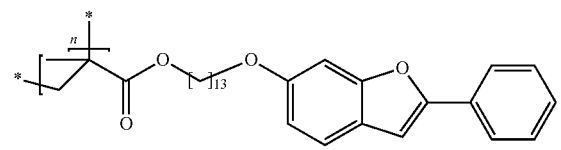

P-05

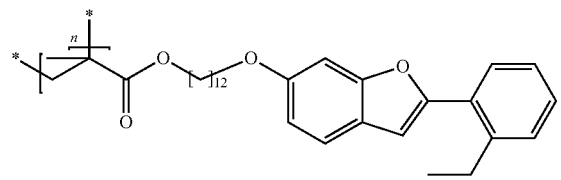

P-06

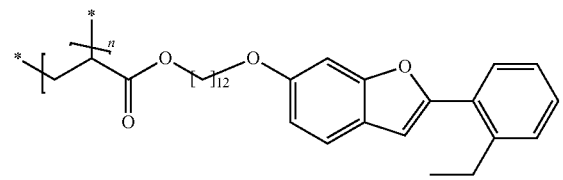

P-07

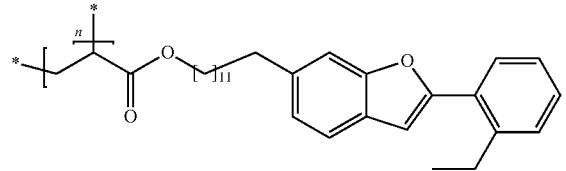

P-08

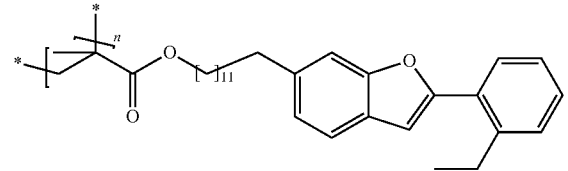

P-09

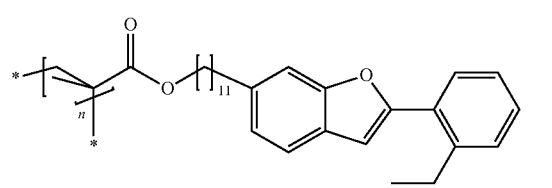

P-10

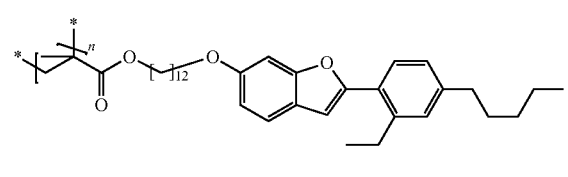

P-11
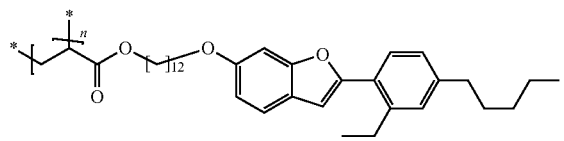
P-12
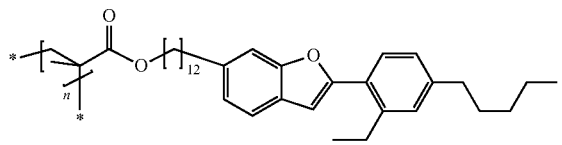
P-13
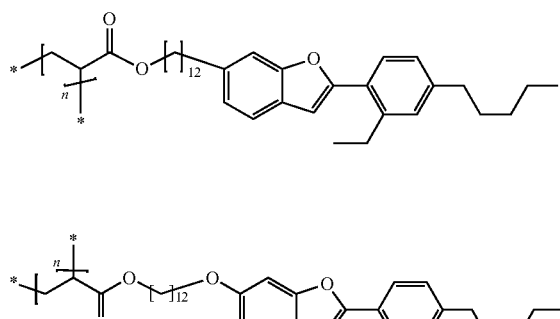
P-14
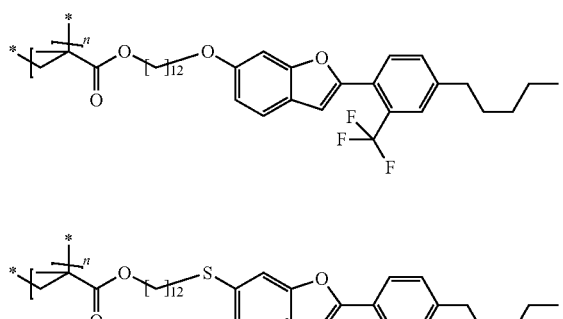
P-15
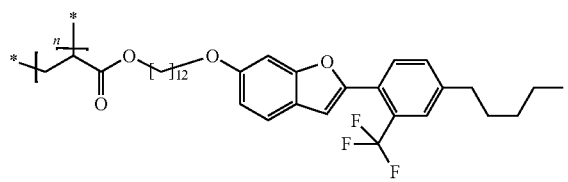
P-16
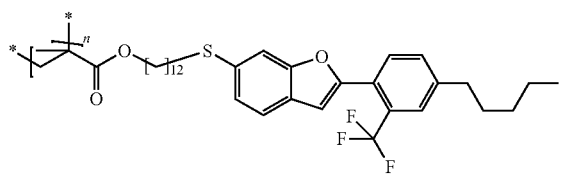
P-17
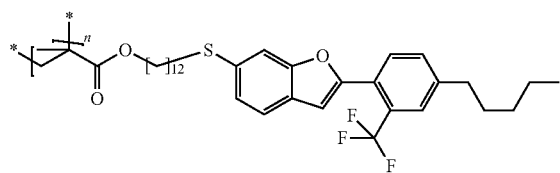
P-18
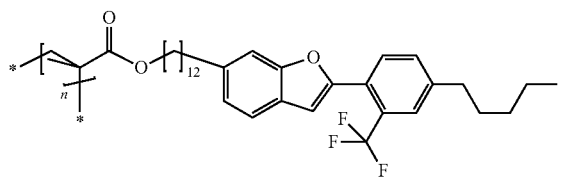
P-19
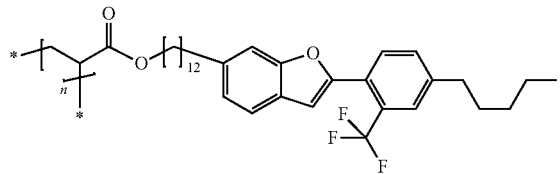
P-20
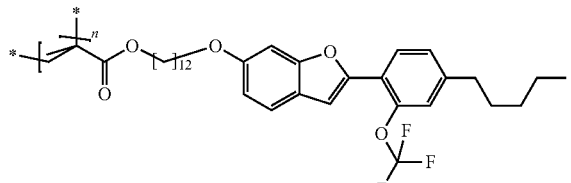
P-21
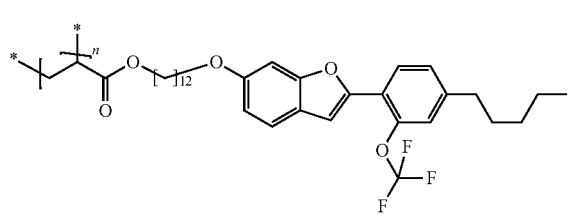
P-22
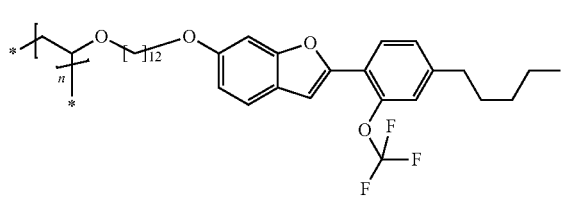
P-23
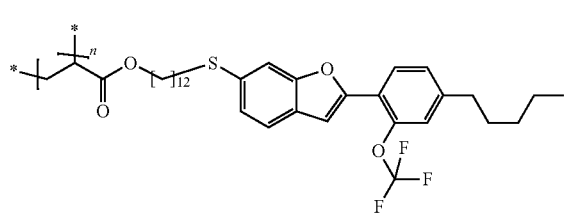
P-24
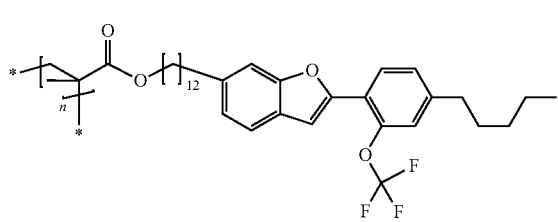

-continued
P-25
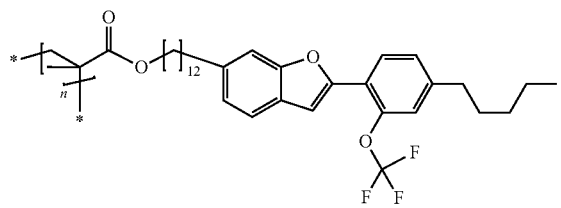
P-26
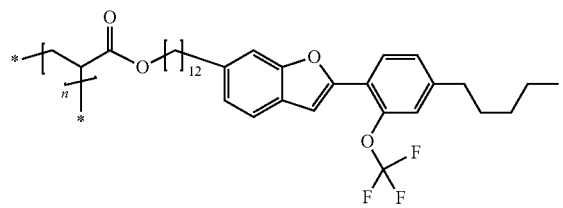
P-27
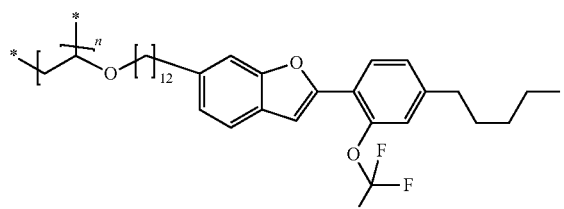
P-28
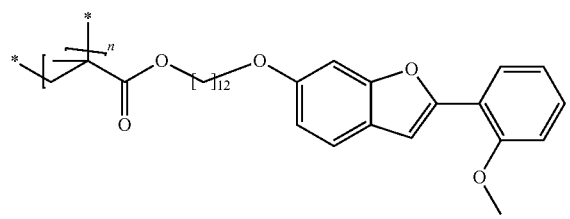
P-29
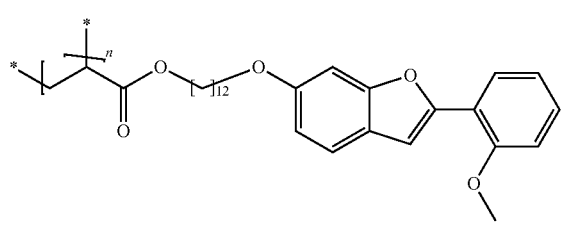
P-30
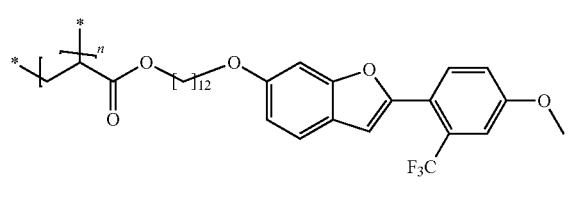
P-31
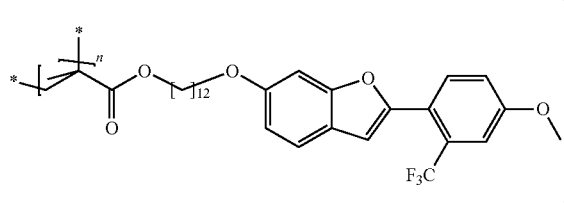
P-32
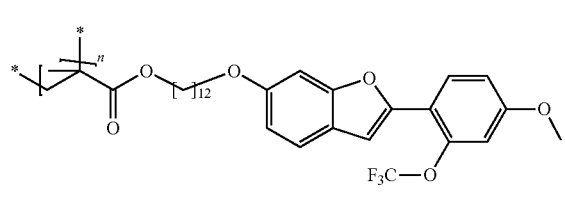
P-33
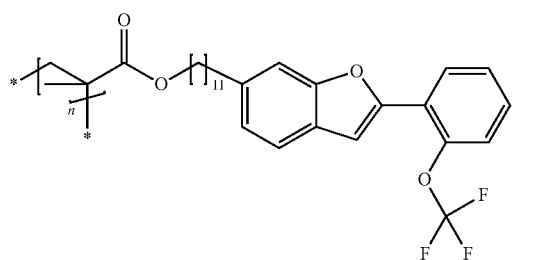
P-34
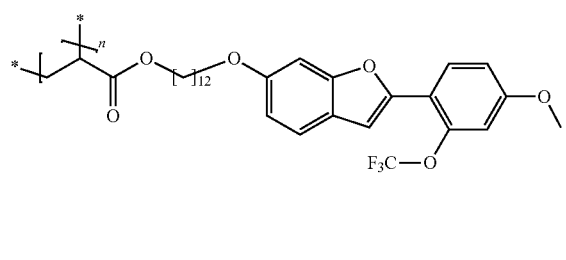
P-35
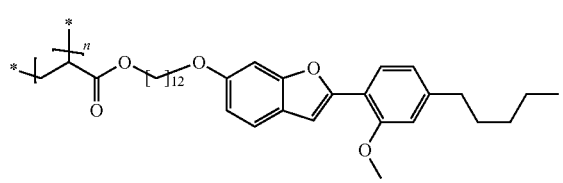
P-36
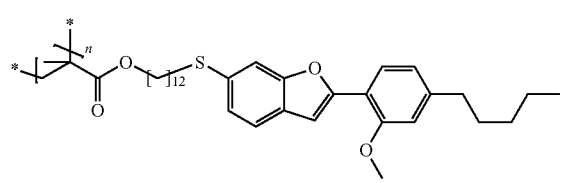
P-37
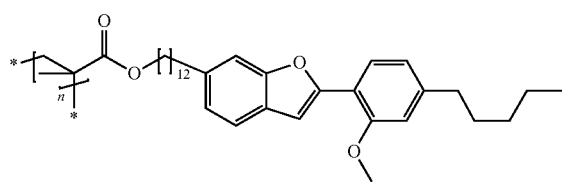
P-38
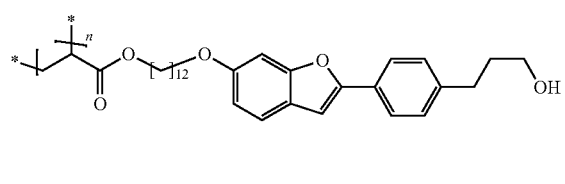

-continued
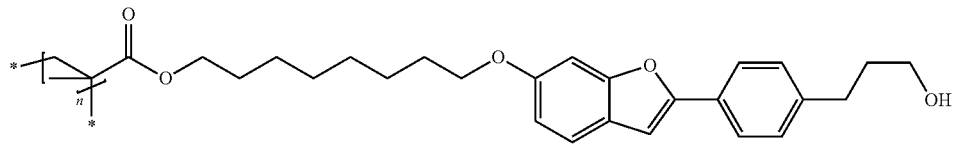
P-39
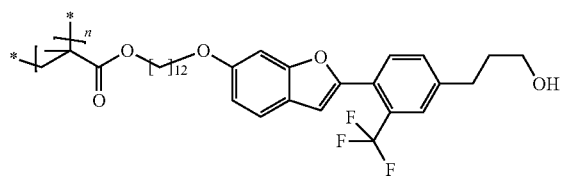
P-40
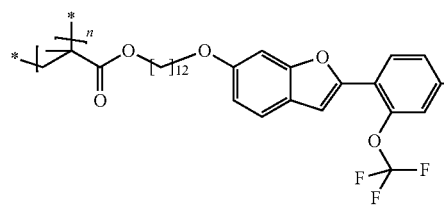
P-41
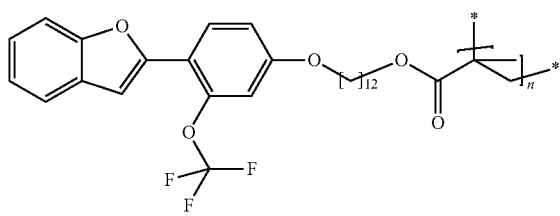
P-42
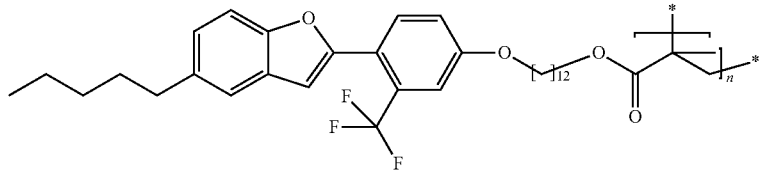
P-43
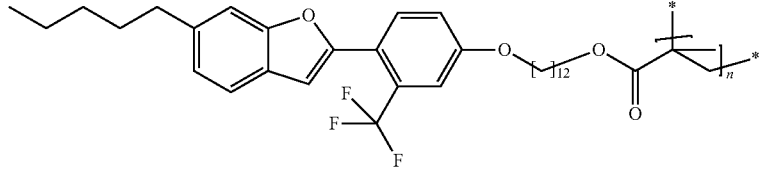
P-44
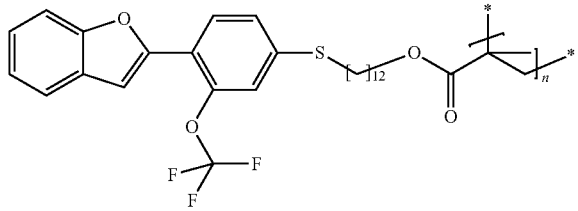
P-45
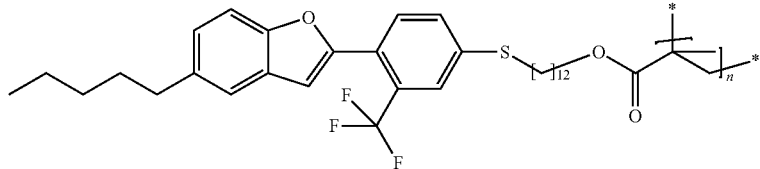
P-46
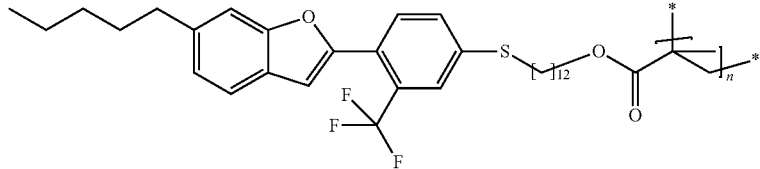
P-47

-continued
P-48
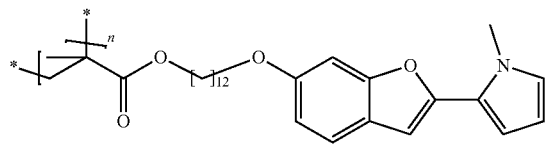
P-49
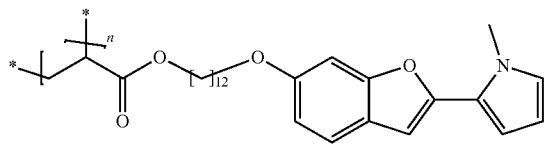
P-50
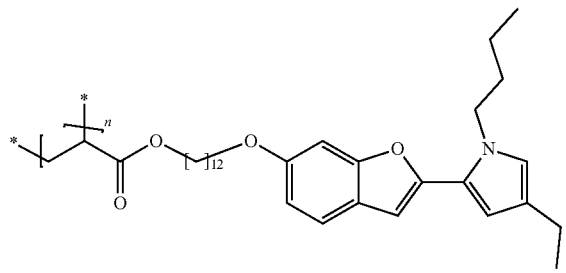
P-51
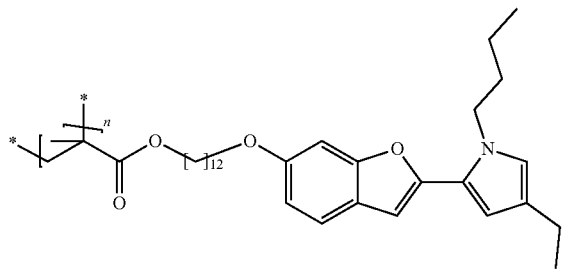
P-52
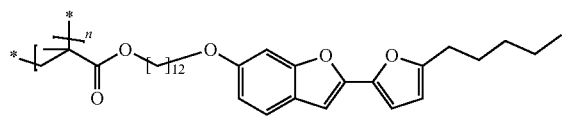
P-53
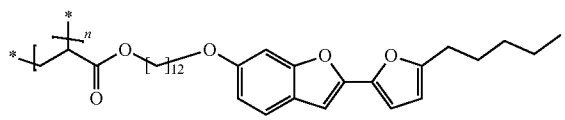
P-54
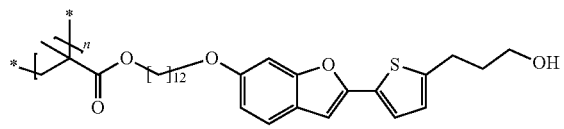
P-55
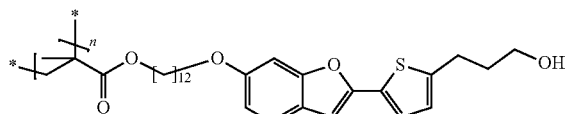
P-56
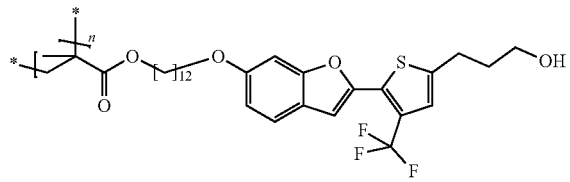
P-57
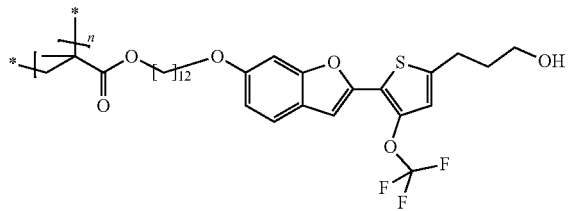
P-58
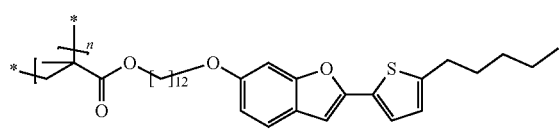
P-59
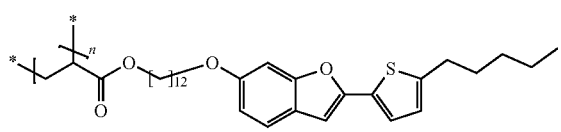
P-60
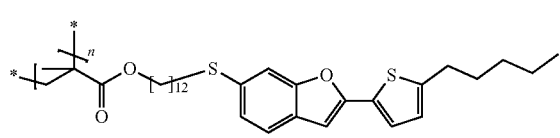
P-61
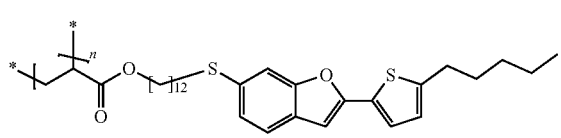
P-62
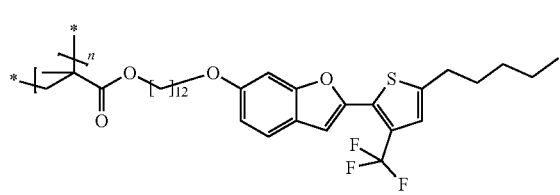
P-63

P-64
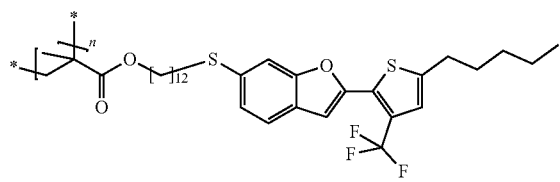
P-65
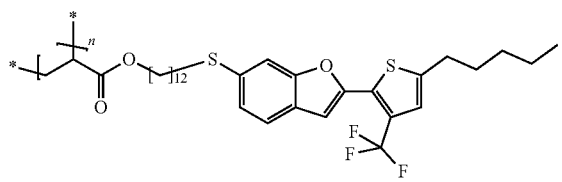
P-66
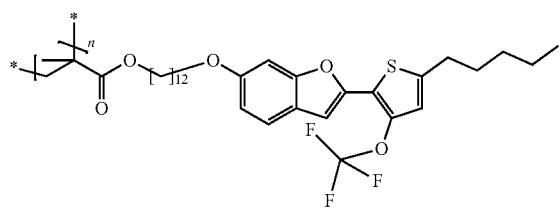
P-67
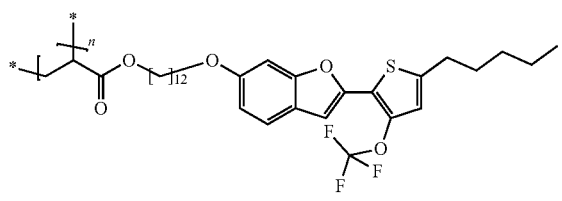
P-68
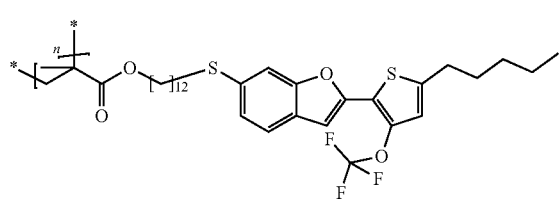
P-69
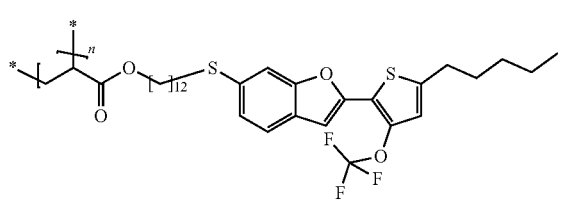
P-70
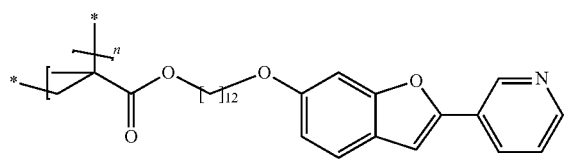
P-71
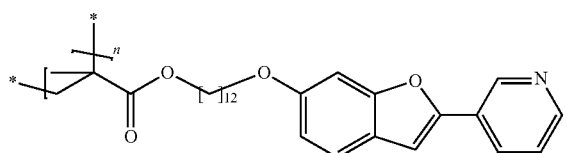
P-72
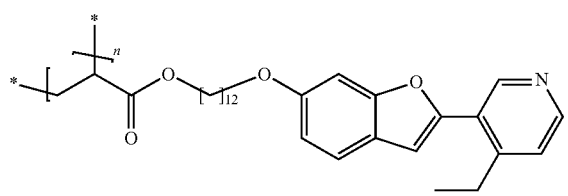
P-73
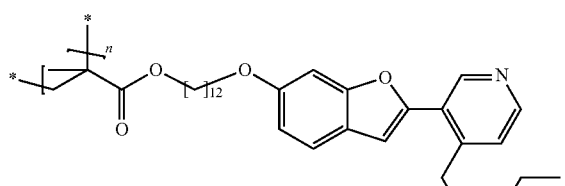
P-74
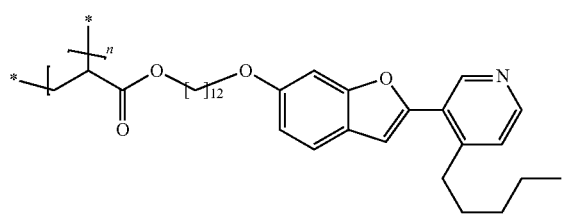
P-75
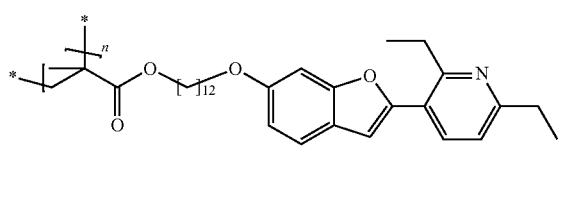
P-76
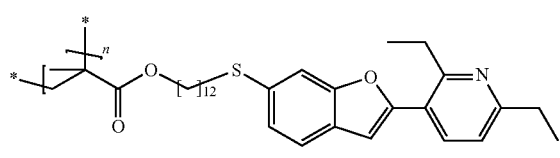
P-77
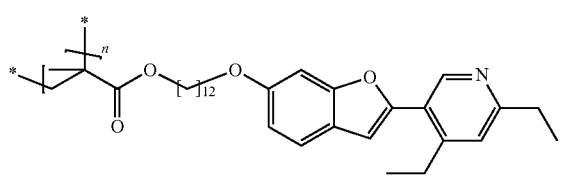

-continued
P-78
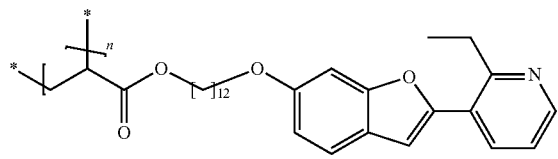
P-79
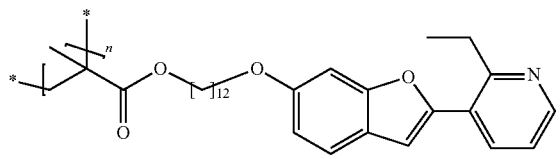
P-80
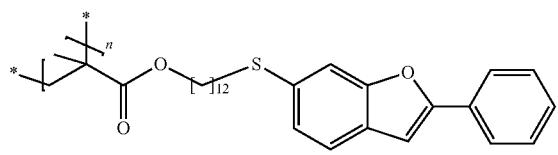
P-81
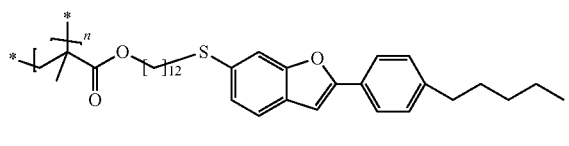
P-82
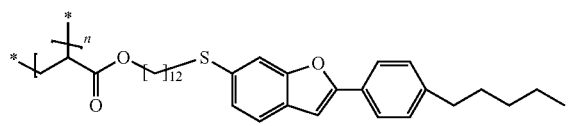
P-83
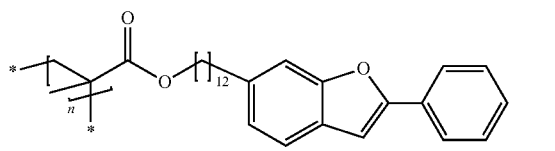
P-84
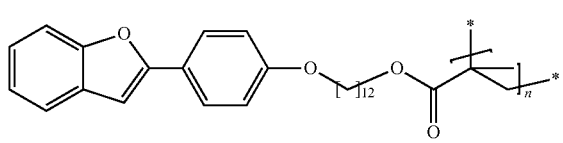
P-85
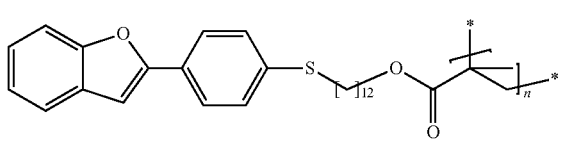
P-86
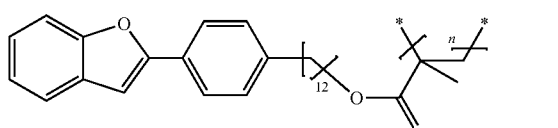
P-87
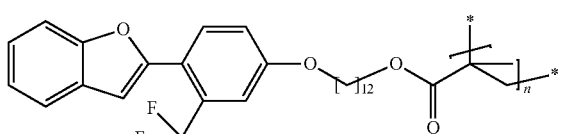
P-88
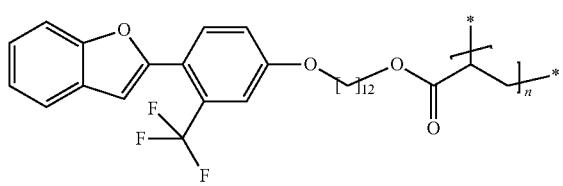
P-89
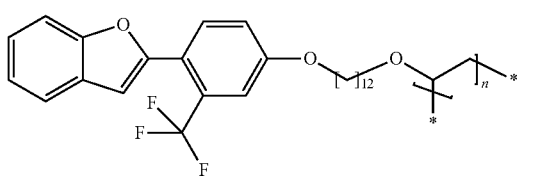
P-90
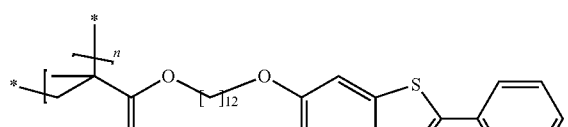
P-91
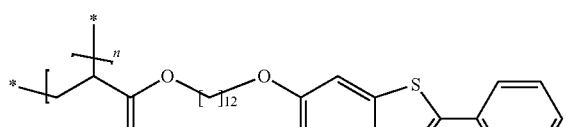
P-92
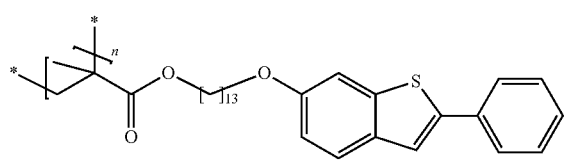
P-93
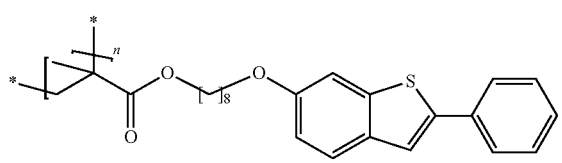

-continued
P-94
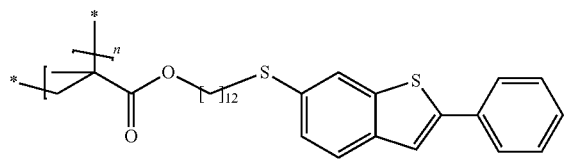
P-95
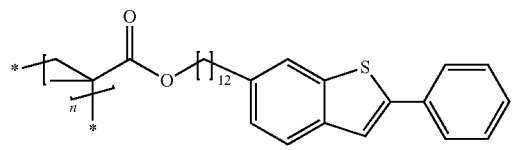
P-96
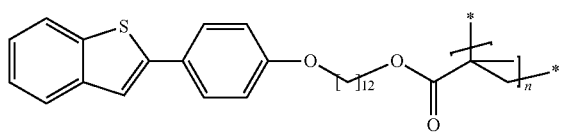
P-97
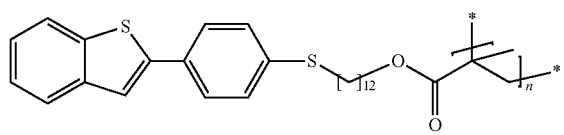
P-98
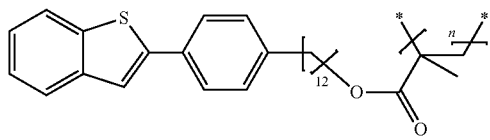
P-99
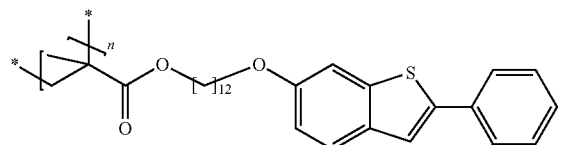
P-100
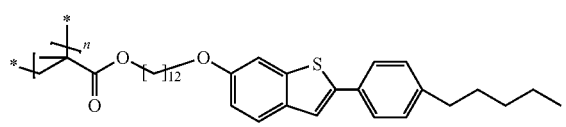
P-101
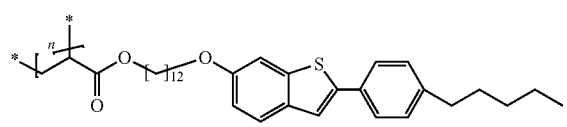
P-102
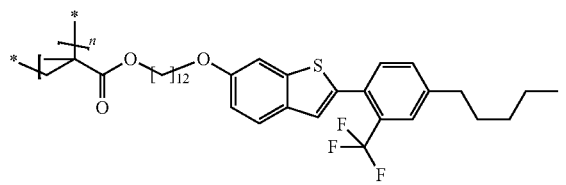
P-103
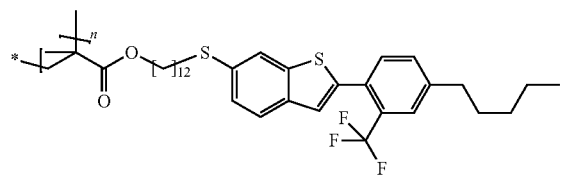
P-104
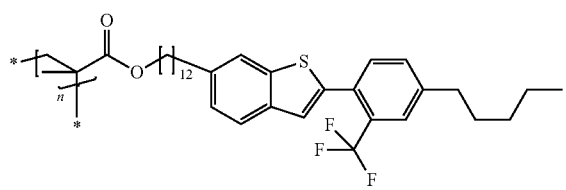
P-105
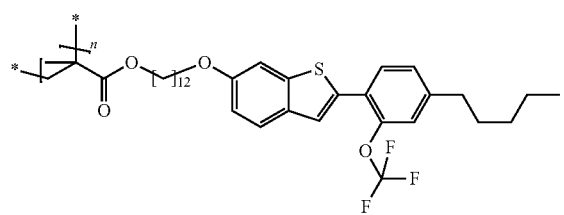
P-106
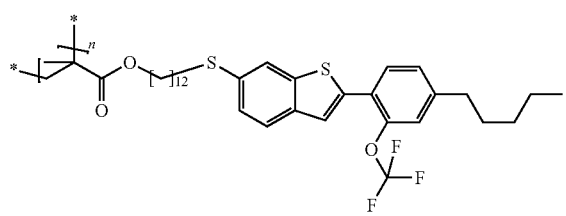
P-107
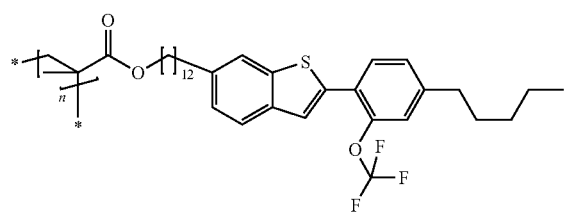
P-108
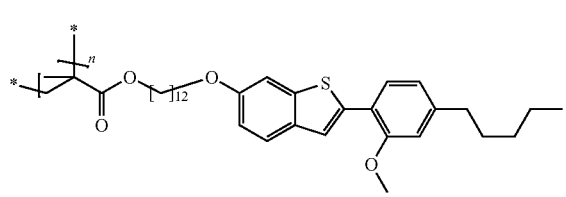
P-109
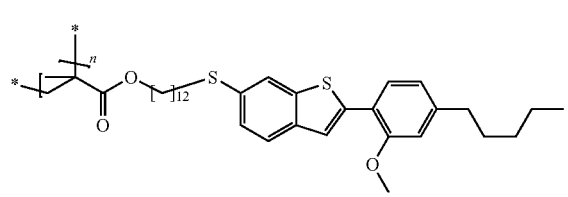

-continued
P-110
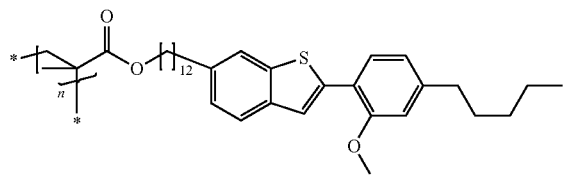
P-111
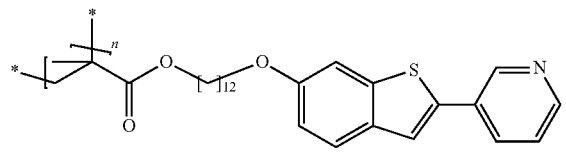
P-112
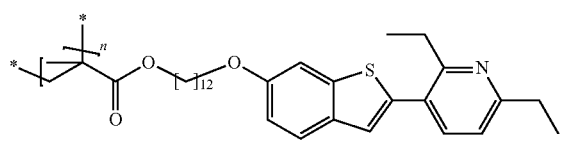
P-113
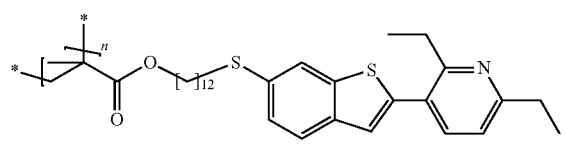
P-114
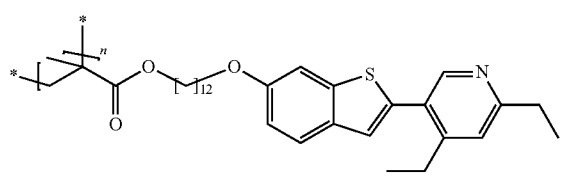
P-115
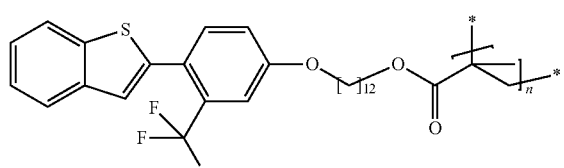
P-116
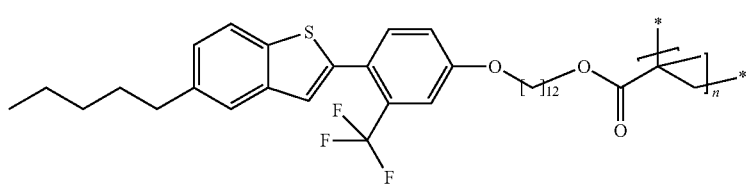
P-117
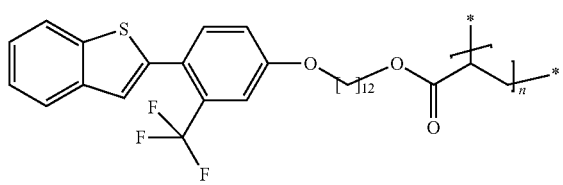
P-118
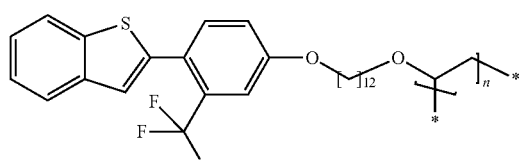
P-119
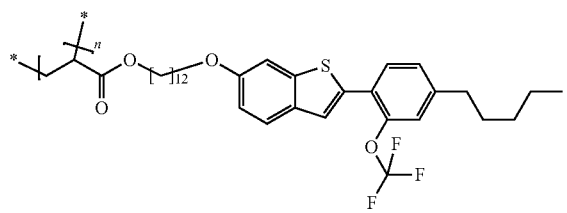
P-120
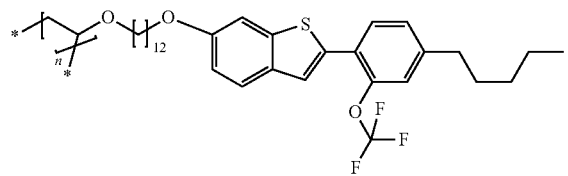
P-121
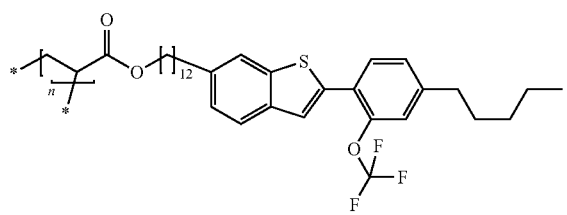
P-122
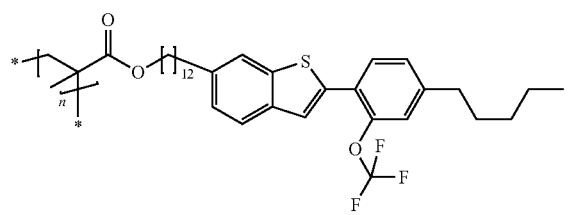

-continued
P-123
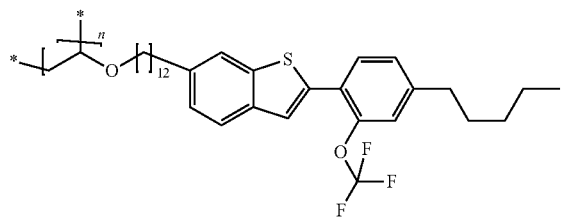
P-124
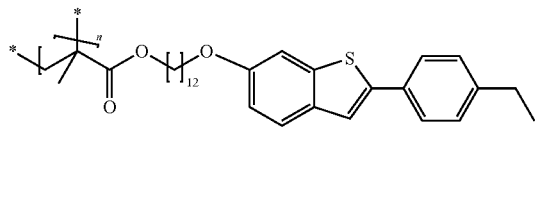
P-125
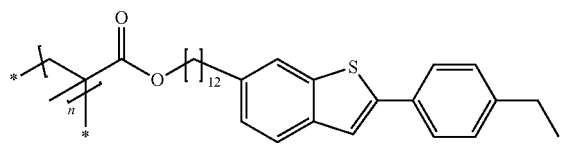
P-126
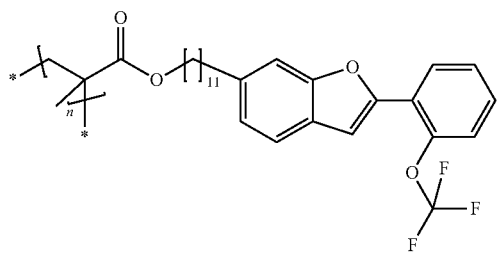
P-127
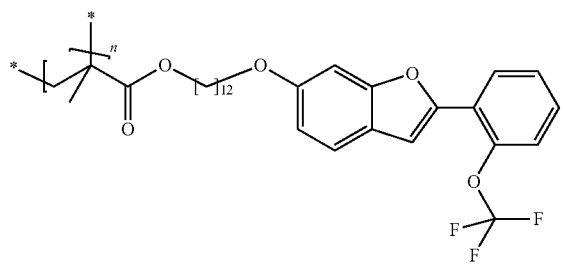
P-128
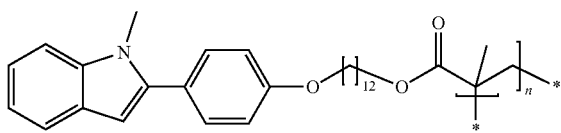
P-129
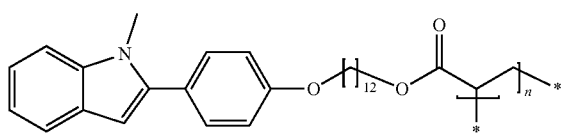
P-130
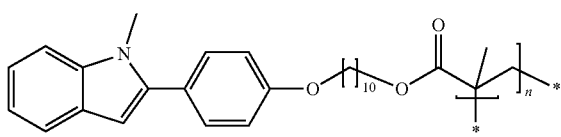
P-131
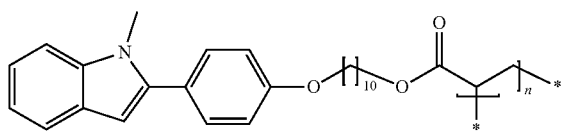
P-132
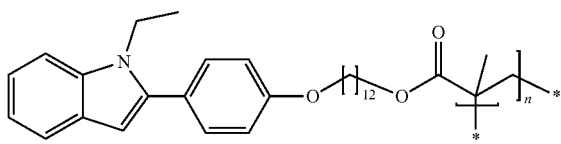
P-133
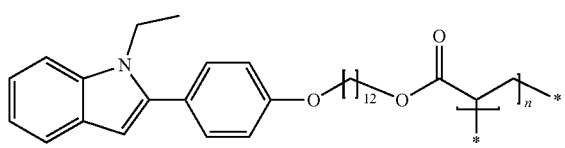
P-134
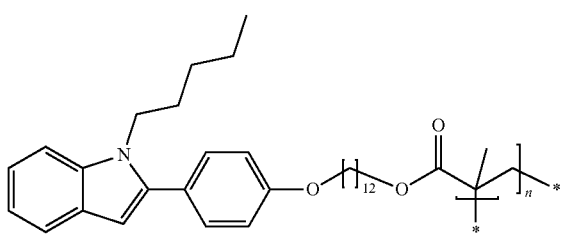

-continued
P-135
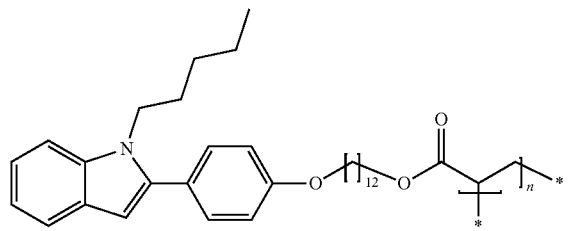
P-136
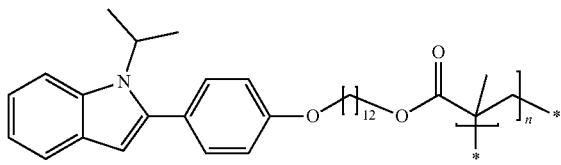
P-137
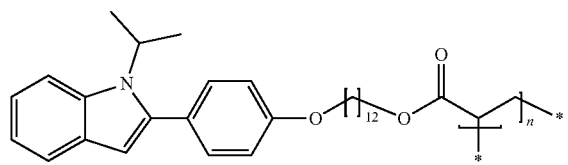
P-138
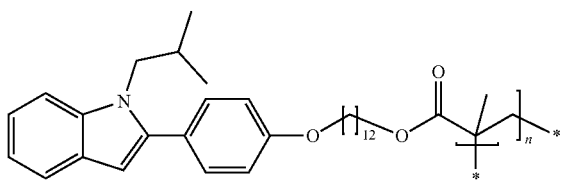
P-139
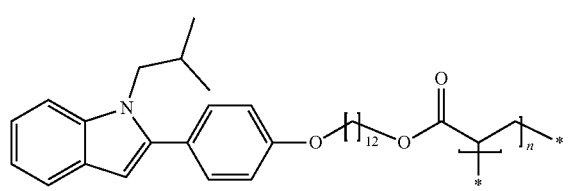
P-140
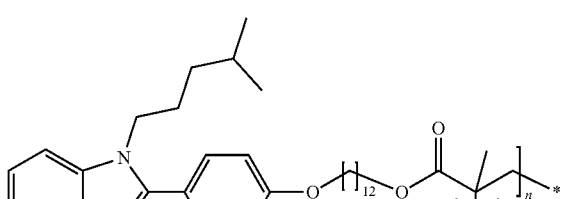
P-141
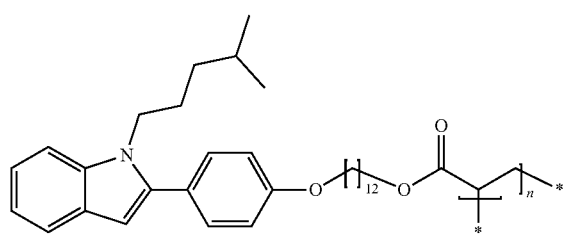
P-142
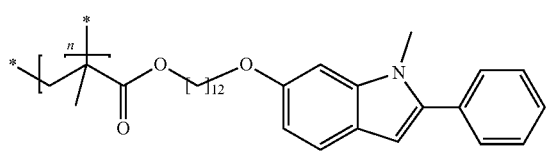
P-143
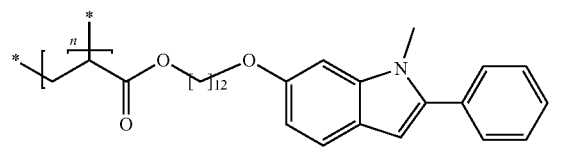
P-144
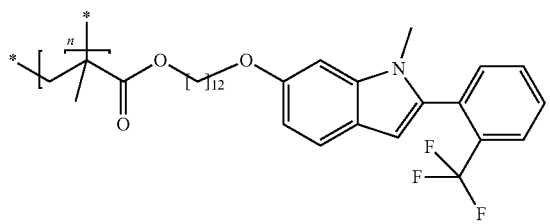
P-145
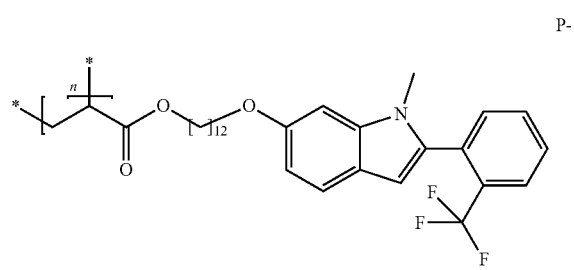
P-146
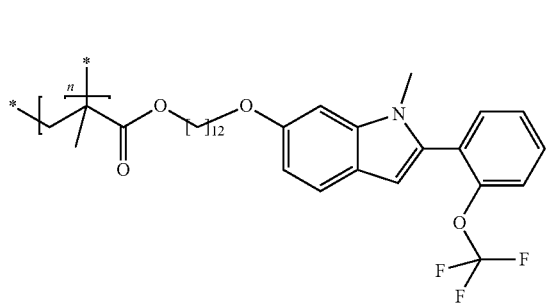

-continued
P-147
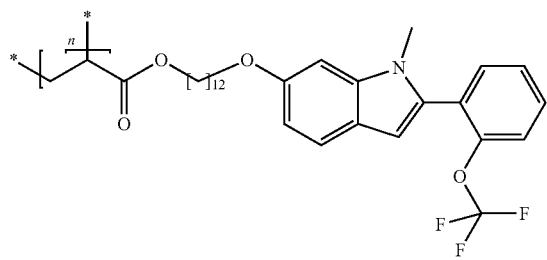
P-148
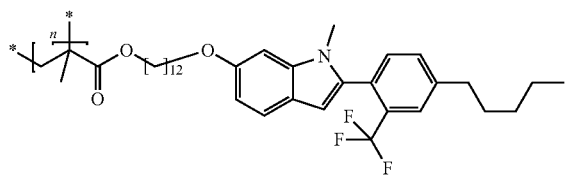
P-149
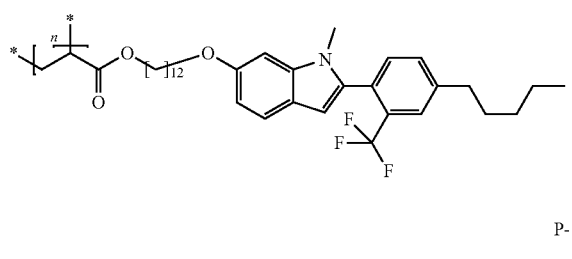
P-150
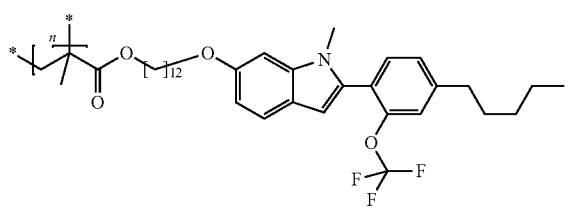
P-151
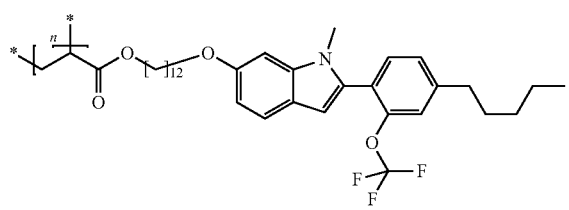
P-152
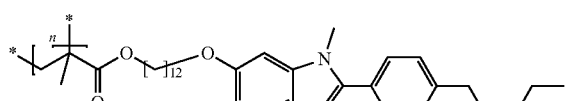
P-153
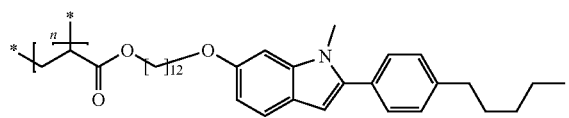
P-154
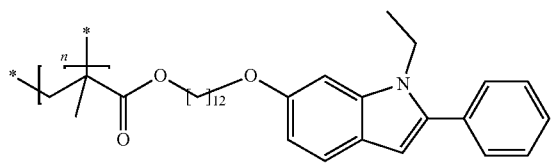
P-155
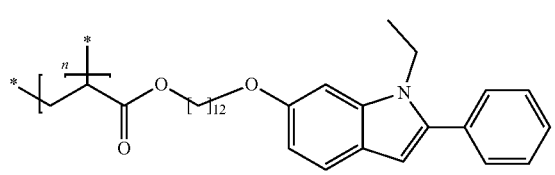
P-156
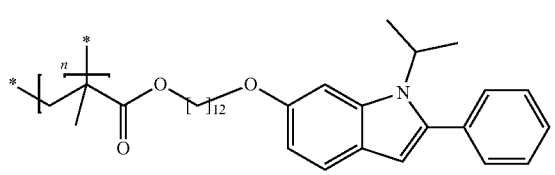
P-157
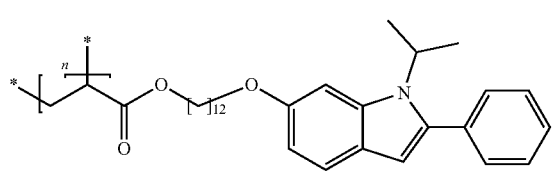
P-158
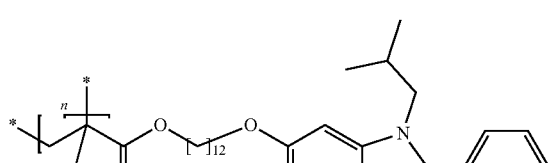
P-159
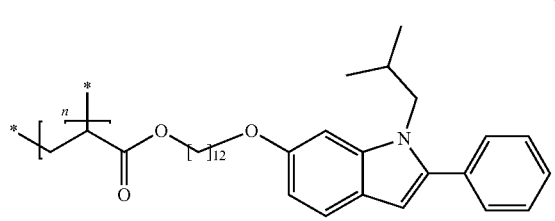
P-160
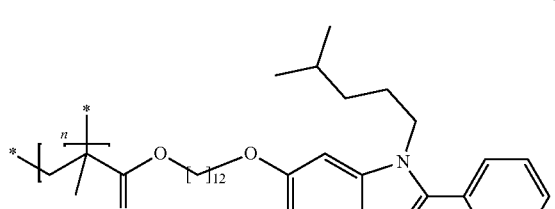

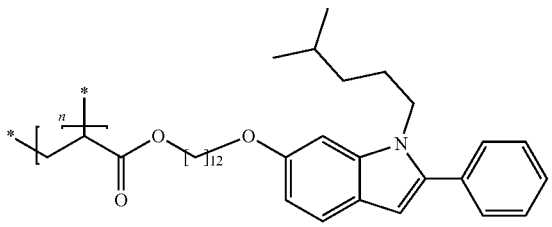

P-161

The letter n gives the degree of polymerization as explained before.

Preferably a co-polymer according to the invention as described before or preferably described before comprises the one or more constitutional units $M^0$ in a molar ratio m1 and the one or more constitutional units $M^2$ in a molar ratio m2, wherein the ratio m1:m2 is at least 0.01 and at most 100.

The oligomers or polymers according to the invention as described before or preferably described may be cross-linked.

The oligomers and polymers of the present invention may be made by any suitable method. It is, however, preferred that the present oligomers and polymers are made by radical polymerization, wherein the polymerization reaction is started by means of a suitable radical polymerization initiator. For the purposes of the present invention the type of radical polymerization initiator is not particularly limited and may be any suitable radical generating compound. Such compounds are well known to the skilled person. Suitable polymerization initiators may be selected from thermal initiators or photoinitiators, i.e. compounds that generate radicals by exposure to heat or irradiation with light of a suitable wavelength. Examples of suitable thermal polymerization initiators may be selected from the groups of compounds comprising one or more peroxide groups, i.e. compounds comprising a group —O—O—, and/or compounds comprising one or more azo groups, i.e. compounds comprising a group —N=N—.

Suitable polymerization initiators comprising one or more peroxide groups may, for example, be selected from the groups consisting of t-butyl(peroxy-2-ethyl-hexanoate), di-(tert-butylcyclohexyl)peroxydicarbonate and benzoyl peroxide.

Suitable polymerization initiators comprising one or more azo groups may, for example, be selected from the group consisting of 1,1'-azobis(cyclohexancarbonitrile) and 2,2'azobis(cyclohexanecarbonitrile) (AIBN).

A suitable example of a photoinitiator is dimethylaminobenzoate/camphorquinone.

If a photoinitiator is used as polymerization initiator, it is preferred that the wavelength required to decompose said photoinitiator is different from the wavelength needed to irradiate the compound of the present application so as to change its optical properties.

Preferably, the radical initiators are used in an amount of at least 0.0001 eq and of at most 0.1 eq of the main monomer. Such radical initiators could be thermal initiators, e.g. azobisisobutyronitrile (AIBN) or photochemical initiators like dimethylaminobenzoate/camphorquinone.

The present invention is also directed to a composition comprising at least one compound of formula (I), (I'), (I") or (I''') as described or preferably described before and/or an oligomer or polymer as described before or preferably described before.

A composition comprising at least one compound of formula (I), (I'), (I") or (I''') as described or preferably described before and an oligomer or polymer as described before is primarily used for the synthesis of block co-polymers with the condition that the oligomer or polymer has at least one reactive group left which may react with the monomers.

Depending upon the intended use such composition may comprise further different components. Such further components may, for example, be selected from the group consisting of UV absorbers, antioxidants and cross-linkers.

The compositions may include or comprise, essentially consist of or consist of the said requisite or optional constituents. All compounds or components which can be used in the compositions are either known and commercially available or can by synthesized by known processes.

The UV absorber that may be used in the present composition is not particularly limited and can easily be selected from those generally known to the skilled person. Generally suitable UV absorbers are characterized by being unsaturated compounds, preferably compounds comprising one or more selected from group consisting of olefinic groups, aryl groups and heteroaryl groups; these groups may be present in any combination.

Suitable UV-absorbers for use in the present composition may, for example, be selected from those comprising a group selected from benzotriazole, benzophenone and triazine. Suitable UV-absorbers are, for example, disclosed in U.S. Pat. Nos. 5,290,892; 5,331,073 and 5,693,095.

Suitable cross-linkers may be used to impart elastomeric properties to the present composition and the articles produced therewith. Typically any suitable di- or tri-functional monomer may be used as crosslinker. Such monomers are generally well known to the skilled person including at least one compound of formula (I''') as described before or preferably described before.

Preferred cross-linker may be selected from the following group of compounds

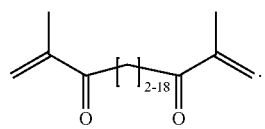

Ethylene glycol dimethacrylate (EGDMA) is particularly preferred.

Suitable antioxidants are phenyl acrylate derivatives bearing a hindered phenol moiety. A preferred antioxidant is

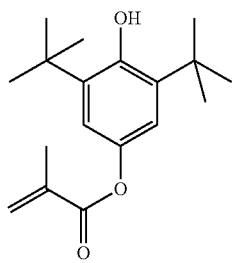

The compounds of formula (I) according to the invention and their oligomers or polymers as described before or preferably described before are particularly well suited for use in optically active devices.

Hence the present invention is also directed to articles e.g. blanks which may be transformed into optically active devices comprising at least one compound of formula (I) as described before or preferably described before or at least one oligomer or polymer as described before or preferably described before.

Preferred articles are blanks which may be transformed into optically active devices or the optically active devices as such. Preferred optically active devices are ophthalmic devices. Examples of such ophthalmic devices include lenses, keratoprostheses, and cornea inlays or rings. More preferably, said article is a blank which may be transformed into an eye-implant or the eye-implant as such. More preferably, said eye-implant is a lens. Most preferably, such article is a blank which may be transformed into an intraocular lens or the intraocular lens as such, which may, for example, be a posterior chamber intraocular lens or an anterior chamber intraocular lens.

A blank of this invention may be produced as a step in the manufacturing process used to create an intraocular lens. For example, without limitation, a manufacturing process may include the steps of polymer synthesis, polymer sheet casting, blank cutting, optic lathe cutting, optic milling, haptic milling or attachment, polishing, solvent extraction, sterilization and packaging.

The present articles according to the invention as described before or preferably described before may be formed by a process comprising the steps of
  providing a composition comprising at least one compound of formula (I) as described herein or preferably described herein and/or an oligomer or polymer as described herein or preferably described herein; and
  subsequently forming the article of said composition.

Intraocular lenses in accordance with the present invention are believed to show particularly advantageous properties in that they are flexible enough so as to be rolled or folded and consequently requiring a much smaller incision for them to be inserted into the eye. It is believed that this will allow for improved healing of the eye, particularly in respect to the time for the eye to heal.

The type of intraocular lens is not limited in any way. It may, for example, comprise one or more optic and one or more haptic components, wherein the one or more optic components serve as lens and the one or more haptic components are attached to the one or more optic components and hold the one or more optic components in place in the eye. The present intraocular lens may be of a one-piece design or of multi-piece design, depending on whether the one or more optic components and the one or more haptic components are formed from a single piece of material (one-piece design) or are made separately and then combined (multi-piece design). The present intraocular lens is also designed in such a way that it allows to be, for example, rolled up or folded small enough so that it fits through an incision in the eye, said incision being as small as possible, for example, at most 3 mm in length.

Additionally, intraocular lenses in accordance with the present invention allow for the non-invasive adjustment of the optical properties, particularly the refractive power, after implantation of the lens into the eye, thus reducing the need for post-surgery vision aids or reducing or totally avoiding follow-up surgery.

In order to change the optical properties and particularly the refractive power of the intraocular lens it is exposed to irradiation having a wavelength of at least 200 nm and of at most 1500 nm. Hence, the present invention is also directed to a process of changing the optical properties of an article as defined or preferably defined herein, said process comprising the steps of
  providing an article as defined herein; and
  subsequently exposing said article to irradiation having a wavelength of at least 200 nm and at most 1500 nm.

Preferably, said irradiation has a wavelength of at least 250 nm or 300 nm, more preferably of at least 350 nm, even more preferably of at least 400 nm, still even more preferably of at least 450 nm, and most preferably of at least 500 nm. Preferably, said irradiation has a wavelength of at most 1400 nm or 1300 nm or 1200 nm or 1100 nm or 1000 nm, more preferably of at most 950 nm or 900 nm, even more preferably of at most 850 nm, still even more preferably of at most 800 nm and most preferably of at most 750 nm.

EXAMPLES

The following examples are intended to show the advantages of the present compounds in a non-limiting way.

Unless indicated otherwise, all syntheses are carried out under an inert atmosphere using dried (i.e. water-free) solvents. Solvents and reagents are purchased from commercial suppliers.

DCM is used to denote dichloromethane. DMF is used to denote dimethylformamide. EE is used to denote ethyl acetate. THF is used to denote tetrahydrofuran.

Co-polymer-properties can be investigated on blanks, prepared by bulk polymerization of the monomers. Co-monomers, cross-linkers and initiators therefore can be purchased from commercial sources. All chemicals are of highest purity available and can be used as received.

Synthesis of Precursor Materials:

Example 1—Bromo-(5-bromo-thiophen-2-yl)-acetic acid methyl ester

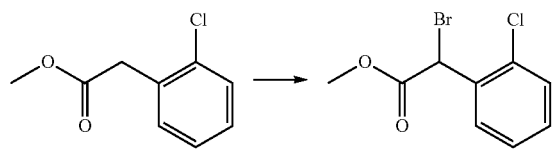

To a stirred solution of the Methyl 2-chlorophenylacetate (0.86 ml; 5.31 mmol) in dichloromethane (10.2 ml; 159 mmol) are added N-bromosuccinimide (1.04 g; 5.84 mmol) and azobisisobutyronitrile (43.6 mg; 0.27 mmol) at room temperature and the mixture is stirred at 100° C. for 16 h under argon atmosphere. The reaction mixture is cooled down to room temperature. The mixture is diluted with diethyl ether and filtered. The filtrate is evaporated to dryness. The oily residue containing solid succinimid is diluted with heptane and filtered again. The solvent is removed to afford Bromo-(2-chloro-phenyl)-acetic acid methyl ester (1.38 g; 4.56 mmol; 86% of theory).

1H NMR (500 MHz, Chloroform-d) δ 7.69 (dd, J=7.6, 1.8 Hz, 1H), 7.31 (dd, J=7.6, 1.7 Hz, 1H), 7.24 (td, J=7.6, 1.7 Hz, 1H), 7.21 (dd, J=7.5, 1.8 Hz, 1H), 5.84 (s, 1H), 3.74 (s, 3H).

Analogously, the following compounds are prepared in the same manner:

| No. | Reactant 1 | Product | Yield |
|---|---|---|---|
| 1a | 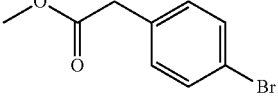<br>CAS: 41841-16-1 | 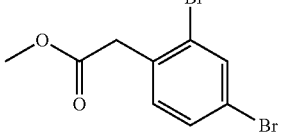 | 75% |
| 1b | 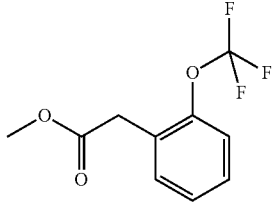 [SMILES: COC(=O)Cc1ccccc1OC(F)(F)F]<br>CAS: 666235-35-4 | 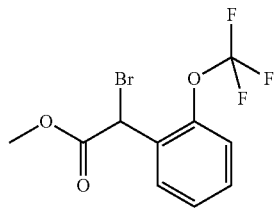 [SMILES: COC(=O)C(Br)c1ccccc1OC(F)(F)F] | 67% |
| 1c | 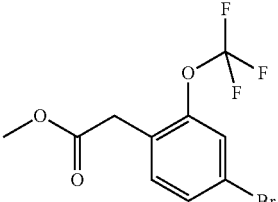<br>CAS: 1805558-53-5 | 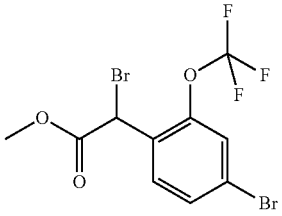 | 53% |
| 1d | 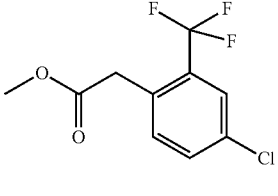 [SMILES: COC(=O)Cc1ccc(Cl)cc1C(F)(F)F]<br>CAS: 95299-14-2 | 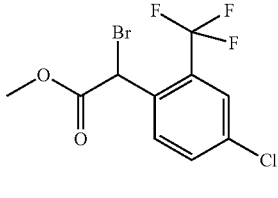 [SMILES: COC(=O)C(Br)c1ccc(Cl)cc1C(F)(F)F] | 52% |
| 1e | 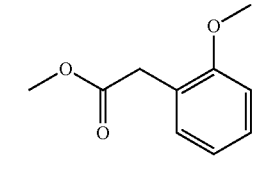<br>CAS: 27798-60-3 | 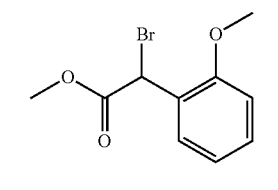 | 57% |
| 1f | 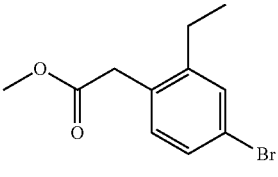<br>CAS: 1227090-87-0 | 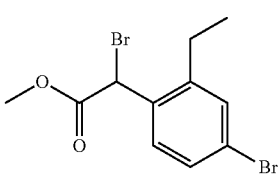 | 45% |

| No. | Reactant 1 | Product | Yield |
|---|---|---|---|
| 1g | CAS: 1784556-50-8 | | 82% |
| 1h | CAS: 67137-56-8 | | 74% |
| 1i | CAS: 474433-35-7 | | 50% |
| 1j | CAS: 1779532-25-0 | | 35% |
| 1k | CAS: 1261572-92-2 | | 54% |
| 1l | CAS: 1261583-67-8 | | 60% |
Example 2—2-(2-Chloro-phenyl)-6-methoxy-benzofuran
-continued
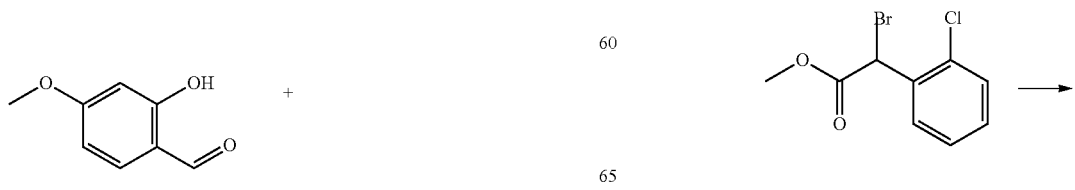

-continued

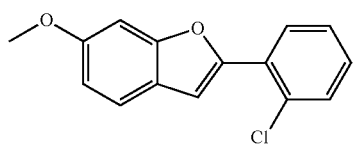

2-Hydroxy-4-methoxybenzaldehyde (800 mg; 5.26 mmol) and bromo-(2-chloro-phenyl)-acetic acid methyl ester (1.39 g; 5.26 mmol) are dissolved in dimethylformamide (26.6 ml; 342 mmol). To the solution is added potassium carbonate (3.63 g; 26.3 mmol). The mixture is stirred at 100° C. for 2 h. The mixture is cooled to 25° C. and portioned to ethyl acetate and HCl (1 N, aq.). The organic layer is separated, washed with brine and dried over MgSO₄. Evaporation of solvent gave brownish oily intermediate. The residue is dissolved in ethanol (21.4 ml; 368 mmol). To the solution is added potassium hydroxide (2.66 g; 47.3 mmol) and the mixture is heated to 100° C. for 2 h. The mixture is cooled to ambient temperature and acidified with HCl (conc.). A solid precipitates which is collected and recrystallized from ethanol to yield 2-(2-Chloro-phenyl)-6-methoxy-benzofuran (500 mg; 1.93 mmol; 37% of theory).

1H NMR (500 MHz, Chloroform-d) δ 8.04 (dd, J=7.9, 1.8 Hz, 1H), 7.54-7.46 (m, 3H), 7.39 (t, J=7.7 Hz, 1H), 7.27 (t, J=7.2 Hz, 1H), 7.10 (d, J=2.4 Hz, 1H), 6.92 (d, J=8.5 Hz, 1H), 3.91 (d, J=1.4 Hz, 3H).

Analogously, the following compounds are prepared in the same manner: R1 means reactant 1, R2 means reactant 2, [P] means product

| No. | | | Yield [%] |
|---|---|---|---|
| 2a | R1 | 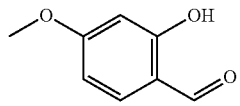 | |
| | R2 | 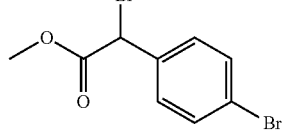 | |
| | [P] |  | 39 |
| 2b | R1 | 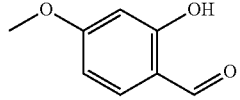 | |
| | R2 | 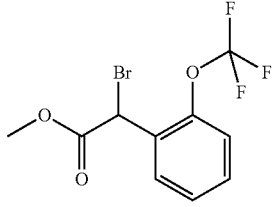 [SMILES: COC(=O)C(Br)c1ccccc1OC(F)(F)F] | |

-continued

| No. | | | Yield [%] |
|---|---|---|---|
| | [P] | 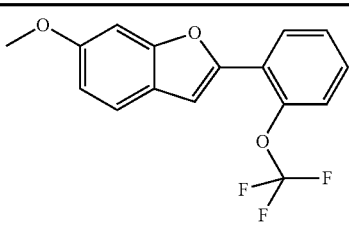 | 34 |
| 2c | R1 | 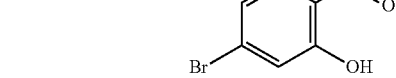 | |
| | R2 | 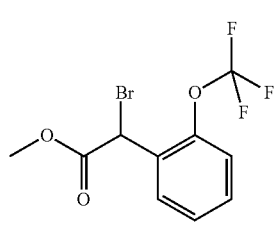 [SMILES: COC(=O)C(Br)c1ccccc1OC(F)(F)F] | |
| | [P] | 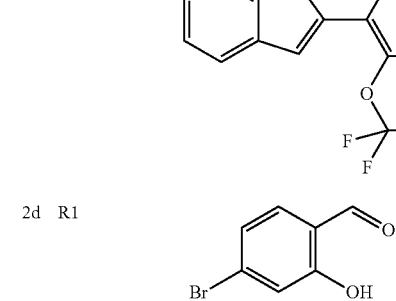 | 33 |
| 2d | R1 | 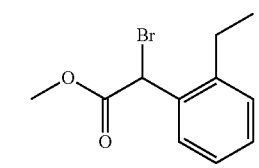 | |
| | R2 | 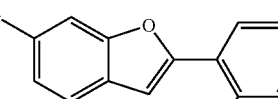 | |
| | [P] | 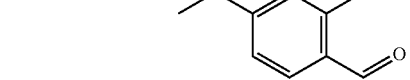 | 25 |
| 2e | R1 | 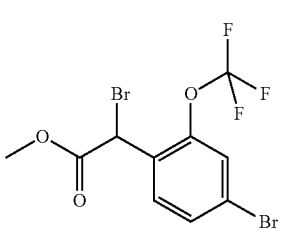 [SMILES: COC(=O)C(Br)c1ccc(Br)cc1OC(F)(F)F] | |
| | R2 | 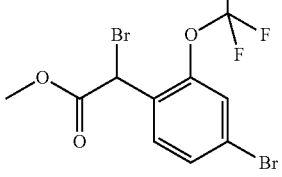 | |

-continued

| No. | | | Yield [%] |
|---|---|---|---|
| | [P] | 6-methoxybenzofuran-2-yl linked to 4-bromo-2-(trifluoromethoxy)phenyl | 42 |
| 2f | R1 | 2-hydroxy-4-methoxybenzaldehyde | |
| | R2 | methyl 2-bromo-2-(4-chloro-2-(trifluoromethyl)phenyl)acetate | |
| | [P] | 6-methoxybenzofuran-2-yl linked to 4-chloro-2-(trifluoromethyl)phenyl | 56 |
| 2g | R1 | 2-hydroxy-4-methoxybenzaldehyde | |
| | R2 | methyl 2-bromo-2-(2-methoxyphenyl)acetate | |
| | [P] | 6-methoxybenzofuran-2-yl linked to 2-methoxyphenyl | 23 |
| 2h | R1 | 2-hydroxy-4-methoxybenzaldehyde | |
| | R2 | methyl 2-bromo-2-(4-bromo-2-ethylphenyl)acetate | |

-continued

| No. | | | Yield [%] |
|---|---|---|---|
| | [P] | 6-methoxybenzofuran-2-yl linked to 4-bromo-2-ethylphenyl | 30 |
| 2i | R1 | 2-hydroxy-4-methoxybenzaldehyde | |
| | R2 | methyl 2-bromo-2-(5-bromofuran-2-yl)acetate | |
| | [P] | 6-methoxybenzofuran-2-yl linked to 5-bromofuran-2-yl | 28 |
| 2j | R1 | 2-hydroxy-4-methoxybenzaldehyde | |
| | R2 | methyl 2-bromo-2-(5-bromothiophen-2-yl)acetate | |
| | [P] | 6-methoxybenzofuran-2-yl linked to 5-bromothiophen-2-yl | 39 |
| 2k | R1 | 2-hydroxy-4-methoxybenzaldehyde | |
| | R2 | methyl 2-bromo-2-(1-methyl-1H-pyrrol-2-yl)acetate | |
| | [P] | 6-methoxybenzofuran-2-yl linked to 1-methyl-1H-pyrrol-2-yl | 40 |
| 2l | R1 | 2-hydroxy-4-methoxybenzaldehyde | |

-continued
| No. | | Yield [%] |
|---|---|---|
| | R2 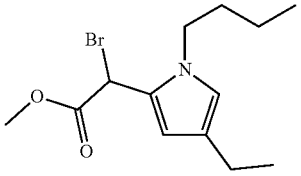 | |
| | [P] 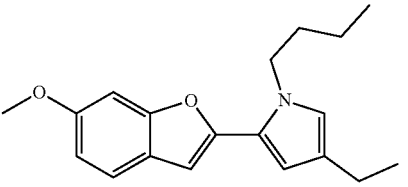 | 50 |
| 2m | R1 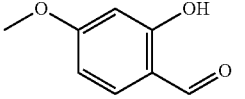 | |
| | R2 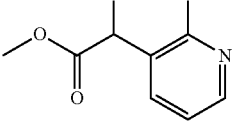 | |
| | [P] 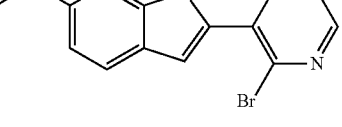 | 47 |
| 2n | R1 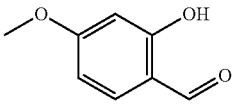 | |
| | R2 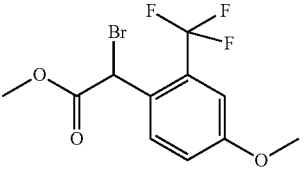 | |
| | [P] 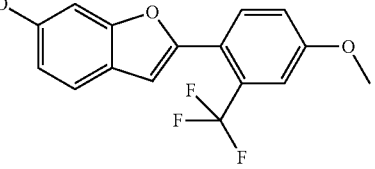 | 42 |
| 2o | R1 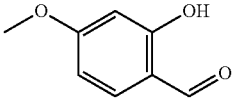 | |
-continued
| No. | | Yield [%] |
|---|---|---|
| | R2 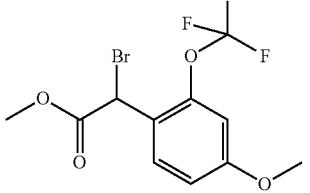 | |
| | [P]  | 38 |
| 2p | R1 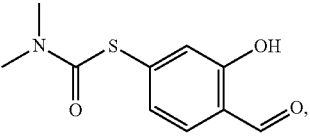<br>CAS: 1356543-46-8 | |
| | R2 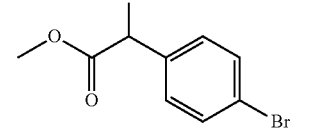 | |
| | [P] 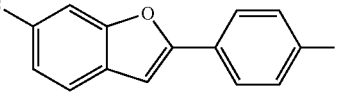 | 15 |
| 2q | R1 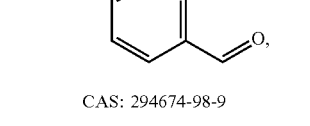<br>CAS: 294674-98-9 | |
| | R2 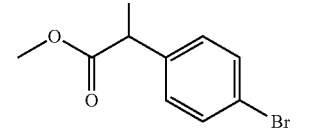 | |
| | [P] 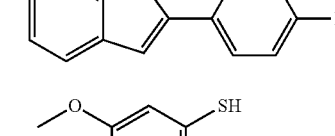 | 22 |
| 2r | R1 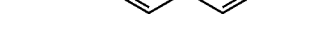<br>CAS: 294674-98-9 | | column chromatography (heptane/ethyl acetate, 5/1) to yield 6-Methoxy-2-(4-pentyl-phenyl)-benzofuran (512 mg; 1.7 mmol; 96% of theory).

1H NMR (500 MHz, Chloroform-d) δ 7.65 (d, J=8.2 Hz, 2H), 7.35 (d, J=8.5 Hz, 1H), 7.17 (d, J=8.1 Hz, 2H), 6.99 (d, J=2.1 Hz, 1H), 6.82 (s, 1H), 6.79 (dd, J=8.5, 2.3 Hz, 1H), 3.80 (s, 3H), 2.59-2.54 (m, 2H), 1.58 (p, J=7.5 Hz, 2H), 1.32-1.24 (m, 4H), 0.83 (t, J=6.9 Hz, 3H).

Analogously, the following compounds are prepared in the same manner: R1 means reactant 1, R2 means reactant 2, [P] means product

| No. | | Yield [%] |
|---|---|---|
| | R2 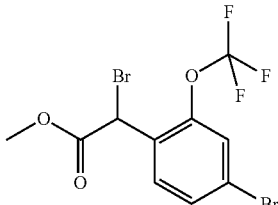 | |
| | [P] 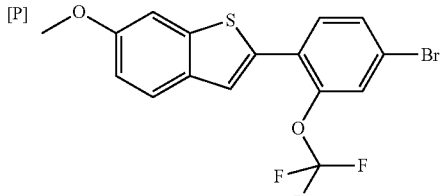 | 35 |

2-(4-Bromo-phenyl)-6-methoxy-benzo[b]thiophene

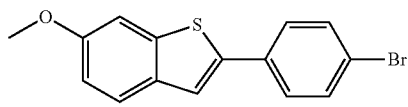 [SMILES: COc1ccc2cc(-c3ccc(Br)cc3)sc2c1]

¹H NMR (500 MHz, Chloroform-d) δ 7.67 (d, J=8.8 Hz, 1H), 7.55-7.52 (m, 4H), 7.46-7.43 (m, 1H), 7.32-7.30 (m, 1H), 7.01 (d, J=8.6 Hz, 1H), 3.91 (s, 3H).

Example 3—6-Methoxy-2-(4-pentyl-phenyl)-benzofuran

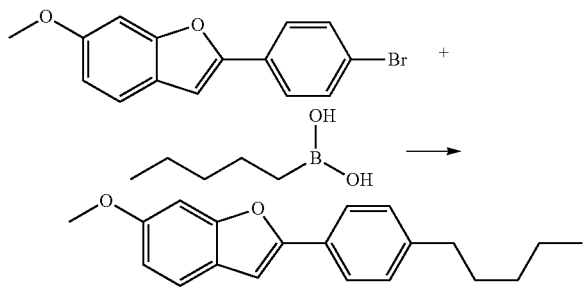

2-(4-Bromo-phenyl)-6-methoxy-benzofuran (550 mg; 1.81 mmol), pentylboronic acid (463 mg; 3.99 mmol) and tripotassium phosphate monohydrate (1.75 g; 7.62 mmol) are dissolved in toluene (19.2 ml; 181 mmol). Then 2-dicyclohexylphosphino-2',6'-dimethoxybiphenyl [SPhos] (149 mg; 359 µmol) and palladium(II) acetate (40.7 mg; 180 µmol) are added and the reaction mixture is heated to 120° C. for 1 d. The cooled reaction mixture is diluted with ethyl acetate and HCl solution (2 M). The solution is transferred to a separatory funnel. The organic phase is extracted with HCl solution (2 M) and water and brine. The organic phase is dried over MgSO₄, filtered and concentrated under reduced pressure. The residue is purified by silica gel

| No. | | | Yield [%] |
|---|---|---|---|
| 3a | R1 | 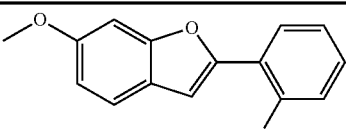 | |
| | R2 | 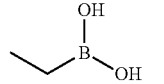 | |
| | [P] | 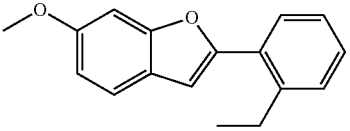 | 42 |
| 3b | R1 | 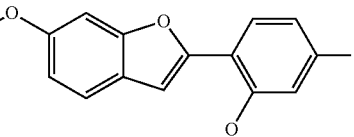 | |
| | R2 |  | |
| | [P] | 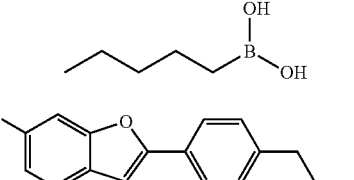 | 95 |
| 3c | R1 | 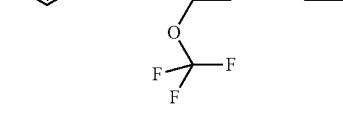 | |
| | R2 | 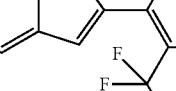 | |
| | [P] | 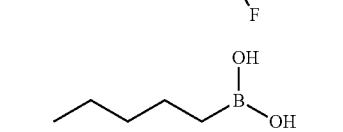 | 75 |

| | | |
|---|---|---|
| 3d | R1 | 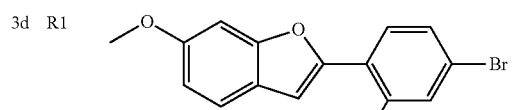 |
| | R2 | 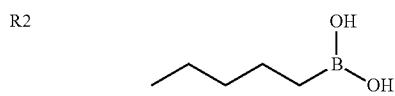 |
| | [P] | 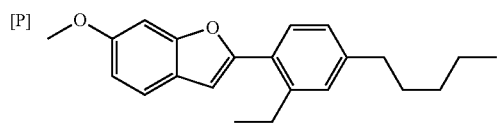 72 |
| 3e | R1 | 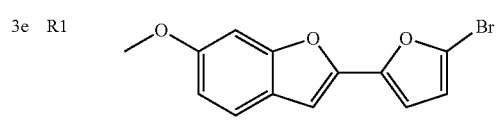 |
| | R2 | 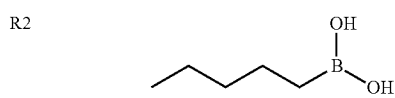 |
| | [P] | 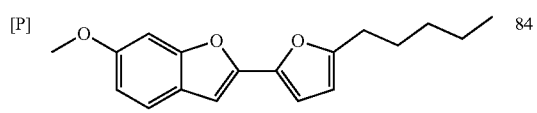 84 |
| 3f | R1 | 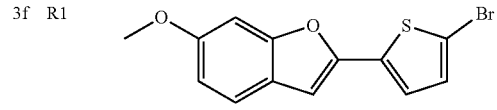 |
| | R2 | 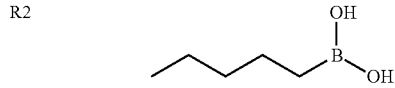 |
| | [P] | 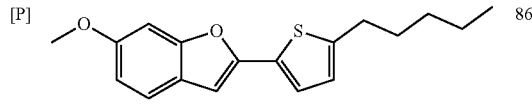 86 |
| 3g | R1 | 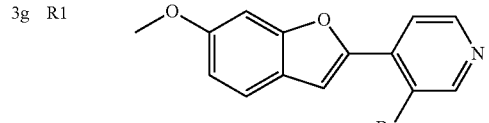 |
| | R2 |  |
| | [P] | 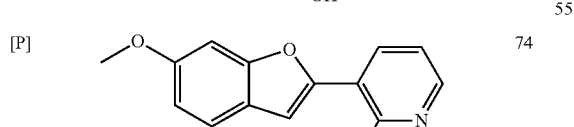 74 |
| 3h | R1 | 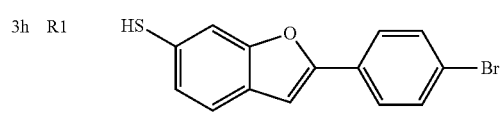 |
| | | |
|---|---|---|
| | R2 | 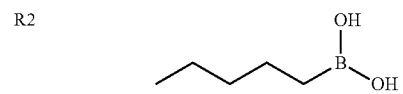 |
| | [P] | 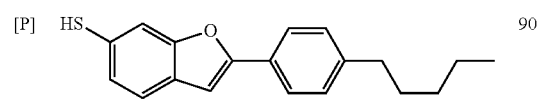 90 |
| 3i | R1 | 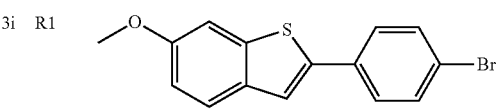 |
| | R2 |  |
| | [P] | 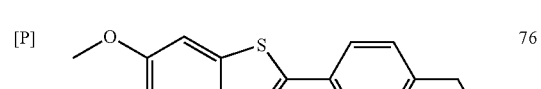 76 |
| 3j | R1 | 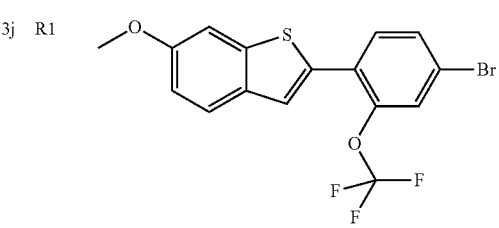 |
| | R2 | 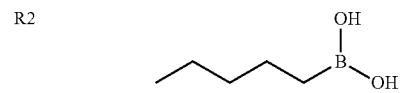 |
| | [P] | 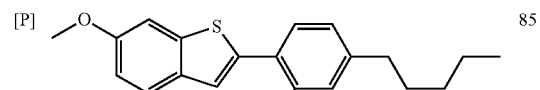 85 |
2-(2-Ethyl-phenyl)-6-methoxy-benzofuran
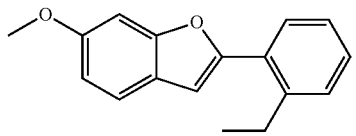 [SMILES: CCc1ccccc1-c1cc2ccc(OC)cc2o1]
¹H NMR (500 MHz, Chloroform-d) δ 7.75 (d, J=7.5 Hz, 1H), 7.50 (d, J=8.5 Hz, 1H), 7.36 (d, J=3.8 Hz, 2H), 7.32 (dq, J=8.7, 3.8 Hz, 1H), 7.10 (d, J=1.9 Hz, 1H), 6.92 (dd, J=8.5, 2.2 Hz, 1H), 6.82 (s, 1H), 3.91 (s, 3H), 2.95 (q, J=7.5 Hz, 2H), 1.32 (t, J=7.5 Hz, 3H).

2-(4-Ethyl-phenyl)-6-methoxy-benzo[b]thiophene

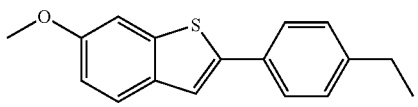 [SMILES: CCc1ccc(-c2cc3ccc(OC)cc3s2)cc1]

$^1$H NMR (500 MHz, Chloroform-d) δ 7.66 (d, J=8.7 Hz, 1H), 7.62 (d, J=8.1 Hz, 2H), 7.44 (s, 1H), 7.33 (d, J=2.2 Hz, 1H), 7.27 (d, J=8.0 Hz, 2H), 7.00 (dd, J=8.7, 2.3 Hz, 1H), 3.91 (s, 3H), 2.71 (q, J=7.6 Hz, 2H), 1.30 (t, J=7.6 Hz, 3H).

Example 4—3-[4-(6-Methoxy-benzofuran-2-yl)-phenyl]-propan-1-ol

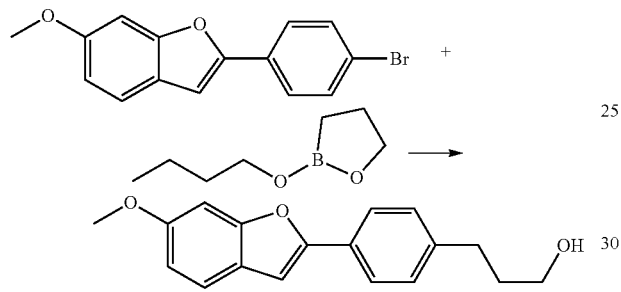

2-(4-Bromo-phenyl)-6-methoxy-benzofuran (2.00 g; 6.6 mmol) and Methanesulfonato(2-dicyclohexylphosphino-2',6'-di-i-propoxy-1,1'-biphenyl)(2-amino-1,1'-biphenyl-2-yl) palladium(II) [RuPhos-Pd-G3] (55.9 mg; 65.5 μmol) are dissolved in tetrahydrofuran (30 ml; 370 mmol). Then 2-Butoxy-1,2-oxaborolan (1.40 ml; 9.2 mmol) and potassium carbonate solution [3 M] (4 ml; 13 mmol) are added and the reaction mixture is refluxed for 16 h. After cooling, water is added and the mixture is extracted with ethyl acetate. The organic phase is dried with MgSO$_4$, filtered and concentrated under reduced pressure. The residue is purified by column chromatography on silica gel (heptane/ethyl acetate, 5/1) to yield 3-[4-(6-Methoxy-benzofuran-2-yl)-phenyl]-propan-1-ol (1.76 g; 6.2 mmol; 95% of theory).

Analogously, the following compounds are prepared in the same manner: R1 means reactant 1, R2 means reactant 2, [P] means product

| No. | | Yield [%] |
|---|---|---|
| 4a | R1 ![methoxybenzofuran-chlorophenyl] | |
| | R2 ![butoxy-oxaborolan] | |
| | [P] ![methoxybenzofuran-phenyl-propanol] | 74 |

Example 5—2-(2-Ethyl-phenyl)-benzofuran-6-ol

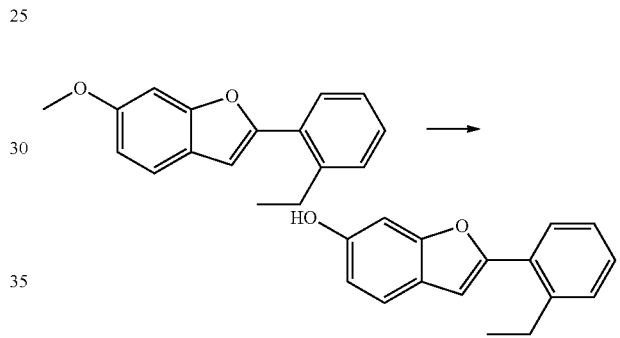

2-(2-Ethyl-phenyl)-6-methoxy-benzofuran (488 mg; 1.93 mmol) is dissolved in dichloromethane (12.3 ml; 193 mmol) and cooled to 5° C. Boron tribromide (220.09 μl; 2.32 mmol) is added dropwise to this solution over the course of 10 min, and stirring is continued for 2 h. The reaction mixture is subsequently slowly poured into ice-water, and the organic phase is diluted with ethyl acetate, washed three times with water, dried over MgSO$_4$, evaporated in a rotary evaporator. 2-(2-Ethyl-phenyl)-benzofuran-6-ol (458 mg; 1.92 mmol; 99% of theory).

Analogously, the following compounds are prepared in the same manner:

| No. | Reactant | Product | Yield |
|---|---|---|---|
| 5a | ![methoxy-benzofuran-OCF3] | ![hydroxy-benzofuran-OCF3] | 92% |

-continued

| No. | Reactant | Product | Yield |
|---|---|---|---|
| 5b | 6-methoxy-2-(1-methyl-1H-pyrrol-2-yl)benzofuran | 6-hydroxy-2-(1-methyl-1H-pyrrol-2-yl)benzofuran | 85% |
| 5c | 1-butyl-2-(6-methoxybenzofuran-2-yl)-4-ethyl-1H-pyrrole | 1-butyl-2-(6-hydroxybenzofuran-2-yl)-4-ethyl-1H-pyrrole | 90% |
| 5d | 6-methoxy-2-(4-pentylphenyl)benzo[b]thiophene | 6-hydroxy-2-(4-pentylphenyl)benzo[b]thiophene | 93% |
| 5e | 6-methoxy-2-(4-pentyl-2-(trifluoromethoxy)phenyl)benzo[b]thiophene | 6-hydroxy-2-(4-pentyl-2-(trifluoromethoxy)phenyl)benzo[b]thiophene | 80% |
| 5f | 2-(2-ethylphenyl)-6-methoxybenzofuran | 2-(2-ethylphenyl)-6-hydroxybenzofuran | 75% |
| 5g | 6-methoxy-2-(4-pentyl-2-(trifluoromethoxy)phenyl)benzofuran | 6-hydroxy-2-(4-pentyl-2-(trifluoromethoxy)phenyl)benzofuran | 77% |
| 5h | 6-methoxy-2-(4-pentyl-2-(trifluoromethyl)phenyl)benzofuran | 6-hydroxy-2-(4-pentyl-2-(trifluoromethyl)phenyl)benzofuran | 67% |
| 5i | 2-(2-ethyl-4-pentylphenyl)-6-methoxybenzofuran | 2-(2-ethyl-4-pentylphenyl)-6-hydroxybenzofuran | 80% |
| 5j | 6-methoxy-2-(5-pentylfuran-2-yl)benzofuran | 6-hydroxy-2-(5-pentylfuran-2-yl)benzofuran | 77% |
| 5k | 6-methoxy-2-(5-pentylthiophen-2-yl)benzofuran | 6-hydroxy-2-(5-pentylthiophen-2-yl)benzofuran | 73% |

| No. | Reactant | Product | Yield |
|---|---|---|---|
| 5l | (6-methoxybenzofuran-2-yl)-(2-ethylpyridin-3-yl) | (6-hydroxybenzofuran-2-yl)-(2-ethylpyridin-3-yl) | 90% |
| 5m | 6-methoxy-2-(4-ethylphenyl)benzothiophene | 6-hydroxy-2-(4-ethylphenyl)benzothiophene | 88% |
| 5n | 6-methoxy-2-[4-pentyl-2-(trifluoromethoxy)phenyl]benzothiophene | 6-hydroxy-2-[4-pentyl-2-(trifluoromethoxy)phenyl]benzothiophene | 76% |

2-Phenyl-benzofuran-6-ol

¹H NMR (500 MHz, DMSO-d6) δ 9.59 (s, 1H), 7.84 (d, J=8.4 Hz, 2H), 7.47 (t, J=7.8 Hz, 2H), 7.43 (d, J=8.4 Hz, 1H), 7.35 (t, J=7.4 Hz, 1H), 7.28 (s, 1H), 6.76 (dd, J=8.4, 2.1 Hz, 1H).

Example 6—12-[2-(2-Ethyl-phenyl)-benzofuran-6-yloxy]-dodecan-1-ol

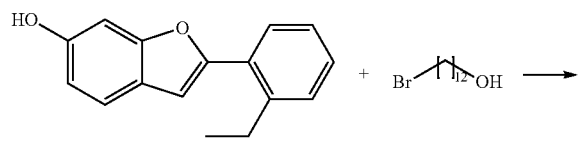

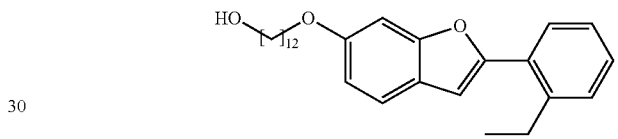

2-(2-Ethyl-phenyl)-benzofuran-6-ol (450 mg; 1.89 mmol) and 12-bromo-dodecan-1-ol (526 mg; 1.98 mmol) are dissolved in acetone (7.76 ml; 106 mmol). Then potassium carbonate (1.31 g; 9.44 mmol) is added and the reaction mixture is refluxed for 2 d. The hot reaction mixture is filtered, washed with hot acetone and ethyl acetate. The filtrate is evaporated under reduced pressure and the remaining colorless liquid is extracted with HCl (2M) and brine, dried, evaporated and purified by column chromatography on silica gel (heptane/EE, gradient [max. 33% EE]), yielding 12-[2-(2-Ethyl-phenyl)-benzofuran-6-yloxy]-dodecan-1-ol (790 mg; 1.87 mmol; 99.0% of theory).

Analogously, the following compounds are prepared in the same manner: R1 means reactant 1, R2 means reactant 2, [P] means product

| No. | | | Yield [%] |
|---|---|---|---|
| 6a | R1 | 2-phenyl-benzofuran-6-ol | |
| | R2 | Br-(CH₂)₁₂-OH | |
| | [P] | 12-(2-phenyl-benzofuran-6-yloxy)-dodecan-1-ol | 88 |

| No. | | | Yield [%] |
|---|---|---|---|
| 6b | R1 | 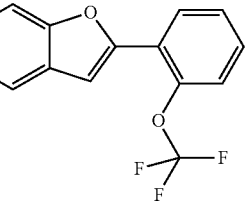 | |
| | R2 | 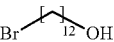 | |
| | [P] | 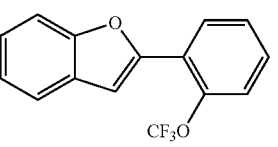 | 86 |
| 6c | R1 | 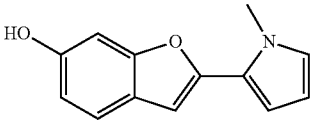 [SMILES: Cn1cccc1-c1cc2ccc(O)cc2o1] | |
| | R2 | 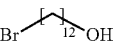 | |
| | [P] | 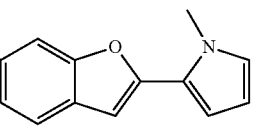 | 82 |
| 6d | R1 | 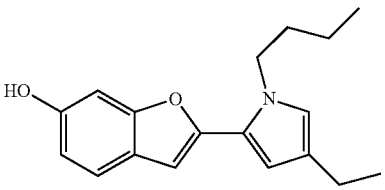 [SMILES: CCCCn1cc(CC)cc1-c1cc2ccc(O)cc2o1] | |
| | R2 | 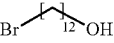 | |
| | [P] | 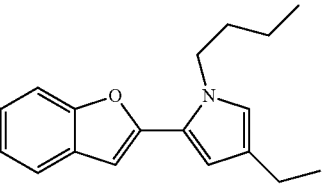 | 79 |
| 6e | R1 | 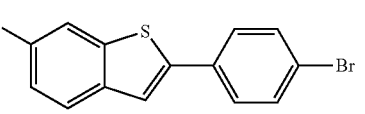 | |
| | R2 | 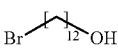 | |
| | [P] | 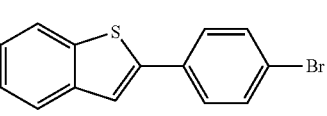 | 84 |

-continued

| No. | | | Yield [%] |
|---|---|---|---|
| 6f | R1 | 6-hydroxybenzothiophene-2-yl linked to 4-bromo-2-(trifluoromethoxy)phenyl | |
| | R2 | Br-(CH₂)₁₂-OH | |
| | [P] | HO-(CH₂)₁₂-O- linked benzothiophene-2-yl-(4-bromo-2-CF₃O-phenyl) | 92 |
| 6g | R1 | 6-hydroxybenzofuran-2-yl linked to 2-ethylphenyl | |
| | R2 | Br-(CH₂)₁₂-OH | |
| | [P] | HO-(CH₂)₁₂-O- linked benzofuran-2-yl-(2-ethylphenyl) | 90 |
| 6h | R1 | 6-hydroxybenzofuran-2-yl linked to 4-pentyl-2-(trifluoromethoxy)phenyl | |
| | R2 | Br-(CH₂)₁₂-OH | |
| | [P] | HO-(CH₂)₁₂-O- linked benzofuran-2-yl-(4-pentyl-2-CF₃O-phenyl) | 71 |
| 6i | R1 | 6-hydroxybenzofuran-2-yl linked to 4-pentyl-2-(trifluoromethyl)phenyl | |
| | R2 | Br-(CH₂)₁₂-OH | |

-continued
| No. | | | Yield [%] |
|---|---|---|---|
| | [P] | 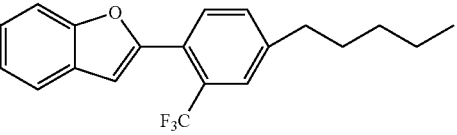 | 86 |
| 6j | R1 | 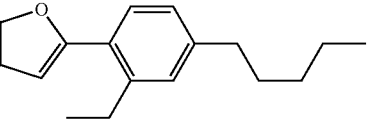 | |
| | R2 | Br—(CH₂)₁₂—OH | |
| | [P] | 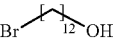 | 92 |
| 6k | R1 | 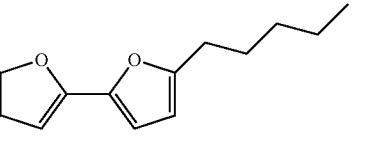 | |
| | R2 | Br—(CH₂)₁₂—OH | |
| | [P] | 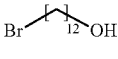 | 82 |
| 6l | R1 | 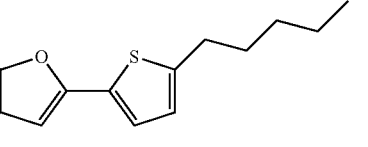 | |
| | R2 | Br—(CH₂)₁₂—OH | |
| | [P] | 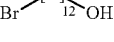 | 75 |
| 6m | R1 | 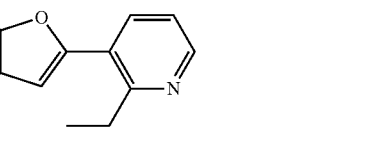 | |
| | R2 | Br—(CH₂)₁₂—OH | |

| No. | | | Yield [%] |
|---|---|---|---|
| | [P] | HO-(CH₂)₁₂-O-[6-benzofuran]-2-(3-(2-ethyl)pyridyl) | 76 |
| 6n | R1 | HO-[6-benzothiophene]-2-(4-ethylphenyl) | |
| | R2 | Br-(CH₂)₁₂-OH | |
| | [P] | HO-(CH₂)₁₂-O-[6-benzothiophene]-2-(4-ethylphenyl) | 84 |
| 6o | R1 | HO-[6-benzothiophene]-2-(4-pentyl-2-(OCF₃)phenyl) | |
| | R2 | Br-(CH₂)₁₂-OH | |
| | [P] | HO-(CH₂)₁₂-O-[6-benzothiophene]-2-(4-pentyl-2-(OCF₃)phenyl) | 77 |

Example 7—2-[11-(4,4,5,5-Tetramethyl-[1,3,2]di-oxaborolan-2-yl)-undecyloxy]-tetrahydro-pyran

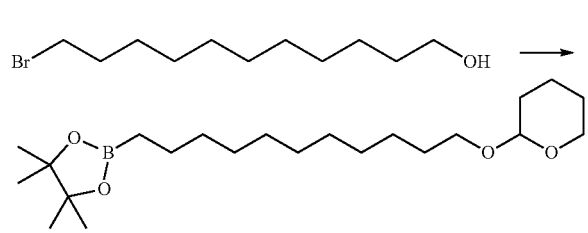

11-Bromo-undecan-1-ol (12 g; 46 mmol) and 3,4-Dihy-dropyran (4.6 ml; 51 mmol) in tetrahydrofuran (45 ml) are treated with p-toluenesulfonic acid (400 mg; 2.32 mmol) and stirred over night. The reaction mixture is filtered and washed with THF. The solvent is evaporated. The residual oil (9.6 g; 28.7 mmol), copper iodide (547 mg; 2.87 mmol), triphenylphosphine (1.1 mg; 4.3 mmol) and bis-(pinaco-lato)-diboron (10.94 g; 43.08 mmol) are added to a Schlenk tube equipped with a stir bar. The vessel was evacuated and filled with argon (three cycles). Dimethylformamide (56 ml) is added under argon atmosphere. The resulting reaction mixture is stirred vigorously at 25° C. for 18 h. The reaction mixture is then diluted with ethyl acetate, filtered through silica gel, concentrated, and purified by column chromatography. 2-[11-(4,4,5,5-Tetramethyl-[1,3,2]dioxaborolan-2-yl)-undecyloxy]-tetrahydro-pyran (7.66 g; 16.00 mmol; 56% of theory) is received.

¹H NMR (500 MHz, DMSO-d6) δ 4.53 (dd, J=4.4, 2.8 Hz, 2H), 3.73 (ddd, J=11.2, 8.1, 3.1 Hz, 2H), 3.60 (dt, J=9.7, 6.7 Hz, 2H), 3.46-3.37 (m, 2H), 3.35-3.30 (m, 2H), 1.77-1.67 (m, 2H), 1.64-1.57 (m, 2H), 1.54-1.41 (m, 9H), 1.36-1.22 (m, 8H), 1.18 (s, 12H).

Analogously, the following compounds are prepared in the same manner:

| No. | Reactant | Product | Yield |
|---|---|---|---|
| 7a | Br-(CH₂)₁₂-OH | pinacol boronate-(CH₂)₁₂-O-THP | 47% |

-continued

| No. | Reactant | Product | Yield |
|---|---|---|---|
| 7b | Br–[]₁₀–OH | (pinacol boronate)–[]₁₀–O–THP | 52% |

Example 8—3-(2-trifluoromethyl-phenyl)-7-(11-hydroxy-undecyl)-coumarin

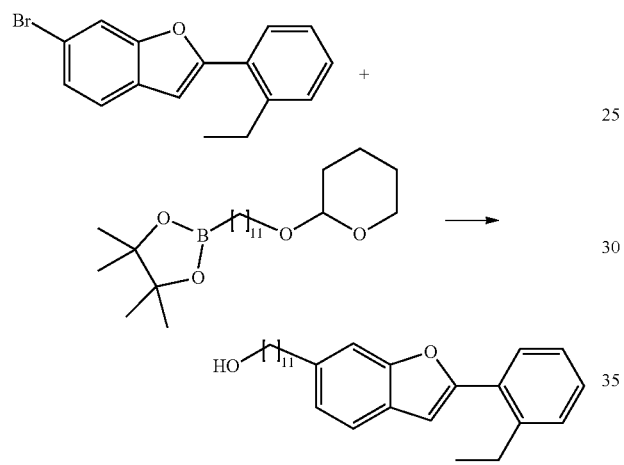

6-Bromo-2-(2-ethyl-phenyl)-benzofuran (1.00 g; 3.3 mmol), 2-[11-(4,4,5,5-Tetramethyl-[1,3,2]dioxaborolan-2-yl)-undecyloxy]-tetrahydro-pyran (1.33 g; 3.5 mmol), potassium phosphate (1.65 g; 6.6 mmol) and tetrakis(triphenylphosphine)-palladium(0) (384 mg; 332 μmol) are added to a flask equipped with a stir bar. Degassed toluene (14.1 ml; 133 mmol) is then added. The reaction vessel is heated to 100° C. for 24 h. The cooled reaction mixture is filtered and washed thoroughly with diluted HCl. The organic phase is concentrated under reduced pressure. The residue is purified by column chromatography. 11-[2-(2-Ethyl-phenyl)-benzofuran-6-yl]-undecan-1-ol (547.5 mg; 1.4 mmol; 42% of theory) is isolated.

Analogously, the following compounds are prepared in the same manner: R1 means reactant 1, R2 means reactant 2, [P] means product

| No. | | Yield [%] |
|---|---|---|
| 8a | R1 Br–benzofuran–(2-ethylphenyl) | |
| | R2 (pinacol boronate)–[]₁₁–O–THP | |
| | [P] HO–[]₁₁–benzofuran–(2-ethylphenyl) | 45 |
| 8b | R1 Br–benzofuran–phenyl–OCF₃ | |
| | R2 (pinacol boronate)–[]₁₁–O–THP | |
| | [P] HO–[]₁₁–benzofuran–phenyl–OCF₃ | 41 |

Preparation of Compounds According to the Invention:

Example 9—Acrylic acid 12-[2-(2-ethyl-phenyl)-benzofuran-6-yloxy]-dodecyl ester

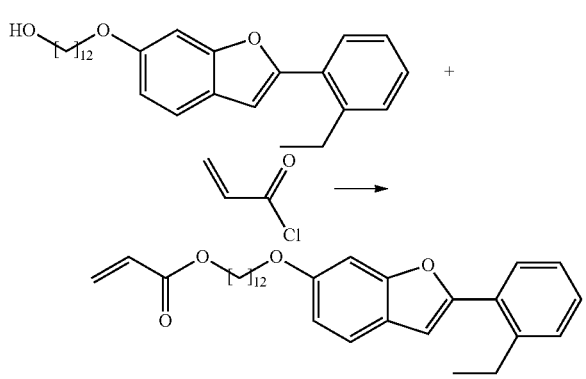

Acryloyl chloride (280 μl; 3.36 mmol) is slowly added to an ice-cooled solution of 12-[2-(2-ethyl-phenyl)-benzofuran-6-yloxy]-dodecan-1-ol (790 mg; 1.87 mmol) in tetrahydrofuran (27.3 ml; 337 mmol) and triethylamine (1.04 ml;

7.48 mmol). The reaction is stirred for 2 h at room temperature. The precipitated solid is filtered off with suction over Celite and silica gel and the filtrate is concentrated under reduced pressure. The residue is purified by column chromatography on silica gel (heptane/ethyl acetate, 5/1) to yield acrylic acid 12-[2-(2-ethyl-phenyl)-benzofuran-6-yloxy]-dodecyl ester (504 mg; 1.06 mmol; 57% of theory).

1H NMR (500 MHz, Chloroform-d) δ 7.74 (d, J=7.5 Hz, 1H), 7.48 (d, J=8.5 Hz, 1H), 7.35 (d, J=3.8 Hz, 2H), 7.31 (dt, J=7.9, 4.3 Hz, 1H), 7.08 (d, J=1.6 Hz, 1H), 6.91 (dd, J=8.5, 2.2 Hz, 1H), 6.81 (s, 1H), 6.42 (dd, J=17.3, 1.4 Hz, 1H), 6.15 (dd, J=17.3, 10.4 Hz, 1H), 5.83 (dd, J=10.4, 1.4 Hz, 1H), 4.18 (t, J=6.7 Hz, 2H), 4.05 (t, J=6.6 Hz, 2H), 2.94 (q, J=7.5 Hz, 2H), 1.85 (dt, J=14.4, 6.7 Hz, 2H), 1.69 (p, J=6.8 Hz, 2H), 1.51 (p, J=7.1 Hz, 2H), 1.44-1.30 (m, 17H).

Analogously, the following compounds are prepared in the same manner by reaction with acryloyl chloride or methacryloyl chloride:

| No. | Reactant | Product | Yield |
|---|---|---|---|
| 9a | | | 67% |
| 9b | | | 75% |
| 9c | | | 74% |
| 9d | | | 75% |
| 9e | | | 84% |
| 9f | | | 85% |
| 9g | | | 81% |
| 9h | | | 87% |

| No. | Reactant | Product | Yield |
|---|---|---|---|
| 9i | | | 79% |
| 9j | | | 72% |
| 9k | | | 87% |
| 9l | | | 91% |
| 9m | | | 87% |
| 9n | | | 90% |
| 9o | | | 70% |
| 9p | | | 69% |
| 9q | | | 88% |

| No. | Reactant | Product | Yield |
|---|---|---|---|
| 9r | 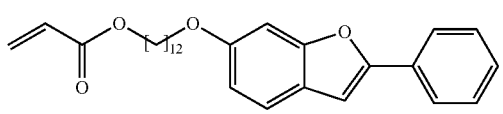 | 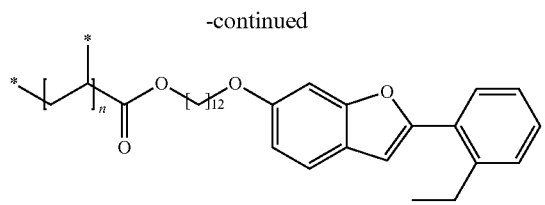 | 91% |

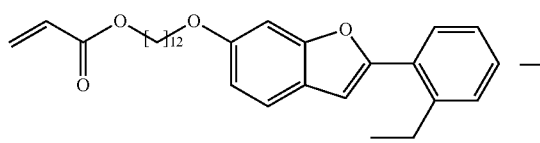

¹H NMR (500 MHz, DMSO-d6) δ 7.86 (d, J=7.4 Hz, 2H), 7.53-7.47 (m, 2H), 7.40-7.36 (m, 2H), 7.34 (s, 1H), 7.24 (s, 1H), 6.89 (d, J=8.4 Hz, 1H), 6.32 (d, J=17.4 Hz, 1H), 6.17 (dd, J=17.4, 10.3 Hz, 1H), 5.93 (d, J=10.2 Hz, 1H), 4.10 (t, J=6.5 Hz, 2H), 4.04 (t, J=6.3 Hz, 2H), 1.78-1.70 (m, 2H), 1.64-1.56 (m, 2H), 1.49-1.40 (m, 2H), 1.31 (d, J=35.8 Hz, 14H).

Example 10—General Polymerization Procedure

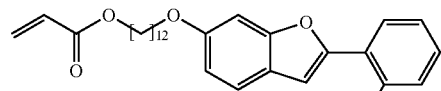

Acrylic acid 12-[2-(2-ethyl-phenyl)-benzofuran-6-yloxy]-dodecyl ester (1.00 g; 2.1 mmol) is dissolved in dimethylformamide (13.1 ml; 168 mmol). The solution is degassed by three freeze-evacuate-thaw cycles. Azobisisobutyronitrile (13.8 mg; 83.9 µmol) is added to the solution and the reaction vessel is then placed in a 65° C. preheated oil bath for 3 d. The mixture is then poured into cold methanol (850 ml; 21 mol). The precipitated Polymer (760.00 mg; 1.6 mmol; 76% of theory) is collected by filtration.

| No. | Reactant | Product | Yield |
|---|---|---|---|
| 10a | 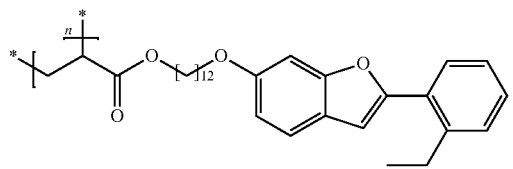 | 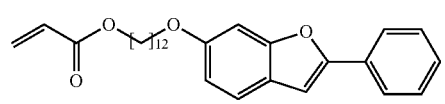 | 75% |
| 10b | 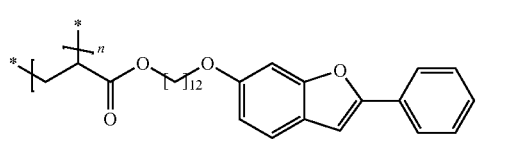 | 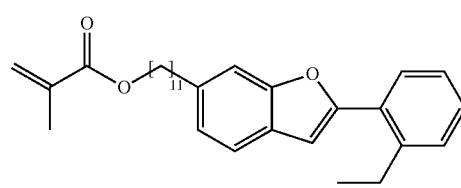 | 64% |
| 10c | 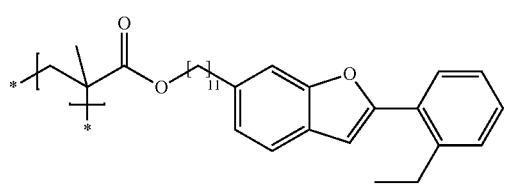 | 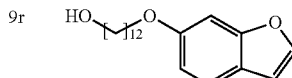 | 61% |

-continued

| No. | Reactant | Product | Yield |
|---|---|---|---|
| 10d | | | 79% |
| 10e | | | 68% |
| 10f | | | 45% |
| 10g | | | 71% |
| 10h | | | 66% |
| 10i | | | 59% |
| 10j | | | 51% |
| 10k | | | 63% |
| 10l | | | 65% |

-continued

| No. | Reactant | Product | Yield |
|---|---|---|---|
| 10m | | | 49% |
| 10n | | | 60% |
| 10o | | | 71% |
| 10p | | | 61% |
| 10q | | | 77% |
| 10r | | | 51% |
| 10s | | | 71% |
| 10t | | | 74% |
| 10u | | | 77% |

Synthesis of Precursor Materials:

Example 11: 5-Methoxy-2-(phenylethynyl)aniline

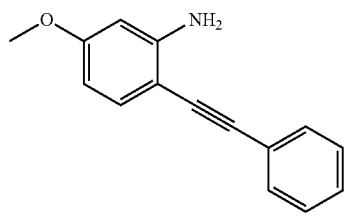 [SMILES: COc1ccc(C#Cc2ccccc2)c(N)c1]

Bis(triphenylphosphine)palladium(II) dichloride (32.1 mg; 45.8 µmol), Copper(I) iodide (17.8 mg; 91.5 µmol), 2-Iodo-5-methoxyaniline (1.2 g; 4.6 mmol), Phenylacetylene (572.5 ml; 5.5 mmol), and Diethylamine (10 ml) was refluxed for 2 h. The residue was chromatographed on silica gel (heptane/EE, 10/1) to afford 5-Methoxy-2-(phenylethynyl)aniline (818 mg; 3.7 mmol; 80% of theory).

1H NMR (500 MHz, Chloroform-d) δ 7.54 (d, J=6.7 Hz, 2H), 7.36 (q, J=8.9, 7.7 Hz, 2H), 7.32 (q, J=8.9, 8.5 Hz, 2H), 6.34 (dd, J=8.5, 2.4 Hz, 1H), 6.30 (d, J=2.3 Hz, 1H), 3.82 (s, 3H).

Example 12: 6-Methoxy-2-phenylindole

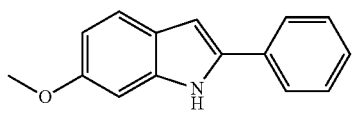

To a refluxing solution of 5-methoxy-2-(phenylethynyl)aniline (826 mg; 3.7 mmol) in toluene (40 ml) was added zinc bromide (420.8 mg; 1.8 mmol) in one portion. After refluxing for 3 d, the reaction mixture was washed with water and extracted with dichloromethane. The combined extracts were dried over MgSO$_4$, filtered, and the solvent was removed under reduced pressure. The solid was passed through a pad of silica gel (heptane/DCM; 5/1) to afford 6-Methoxy-2-phenylindole (585 mg; 2.6 mmol; 71% of theory) and was used in the next step without further analyses.

Example 13: 6-Methoxy-1-methyl-2-phenylindole

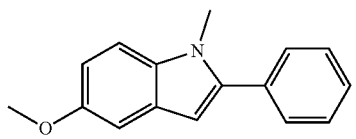 [SMILES: COc1ccc2c(c1)cc(-c1ccccc1)n2C]

To a solution of 6-Methoxy-2-phenylindole (488 mg; 2.2 mmol) in DMF (25 ml) was added methyl iodide (304 µl; 4.8 mmol) followed by sodium hydride (182 mg; 4.6 mmol). The mixture was stirred at room temperature for 16 h. Then the mixture was poured onto an ice/NaOH (2M) mixture and the resulting emulsion was extracted with DCM. After drying over MgS04, the solution was evaporated to dryness. The residue was purified by column chromatography over silica gel eluting with DCM to yield 198 mg (826 µmol; 38% of theory) of the title compound.

1H NMR (500 MHz, Chloroform-d) δ 7.54 (d, J=8.2 Hz, 1H), 7.52 (d, J=7.0 Hz, 2H), 7.48 (t, J=7.6 Hz, 2H), 7.41 (d, J=7.3 Hz, 1H), 6.86 (s, 1H), 6.85 (dd, J=8.4, 1.4 Hz, 1H), 6.52 (s, 1H), 3.94 (s, 3H), 3.73 (s, 3H).

Analogously, the following compounds are prepared in the same manner:

| No. | Reactant 1 | Reactant 2 | Product | Yield |
|---|---|---|---|---|
| 13a | 6-methoxy-2-phenylindole | ethyl iodide | 1-ethyl-6-methoxy-2-phenylindole | 67% |
| 13b | 6-methoxy-2-phenylindole | isopropyl iodide | 6-methoxy-1-isopropyl-2-phenylindole | 75% |
| 13c | 6-methoxy-2-phenylindole | isobutyl iodide | 1-isobutyl-6-methoxy-2-phenylindole | 74% |

| No. | Reactant 1 | Reactant 2 | Product | Yield |
|---|---|---|---|---|
| 13d | 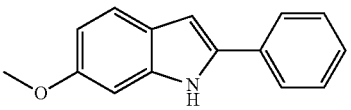 [SMILES: COc1ccc2cc(-c3ccccc3)[nH]c2c1] | 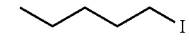 | 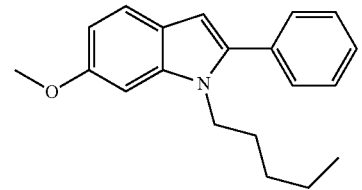 [SMILES: CCCCCn1c(-c2ccccc2)cc2ccc(OC)cc21] | 85% |
| 13e | 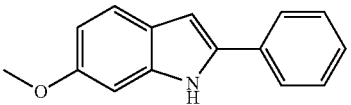 | 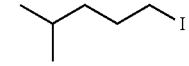 | 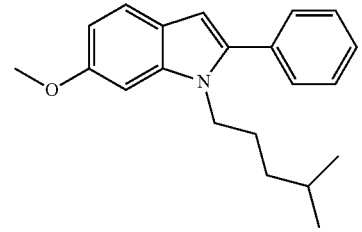 [SMILES: COc1ccc2cc(-c3ccccc3)n(CCCC(C)C)c2c1] | 83% |

Example 14: 6-Hydroxy-1-Methyl-2-phenylindole

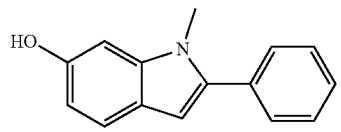 [SMILES: Cn1c(-c2ccccc2)cc2ccc(O)cc21]

6-Methoxy-1-methyl-2-phenylindole (184 mg; 775 µmol) is dissolved in DCM (10 ml) and cooled to 5° C. Boron tribromide (96.6 µl; 1.0 mmol) are added dropwise to this solution, and stirring is continued overnight. Water is subsequently slowly added to the mixture, and the organic phase is diluted with ethyl acetate, washed three times with water, dried over MgSO4, evaporated under reduced pressure and filtered through a pad of silica gel with DCM to yield 6-Hydroxy-1-Methyl-2-phenylindole (117 mg; 524 µmol; 68% of theory).

1H NMR (500 MHz, Chloroform-d) δ 7.54-7.46 (m, 5H), 7.41 (t, J=6.4 Hz, 1H), 6.84 (d, J=2.2 Hz, 1H), 6.72 (dd, J=8.4, 2.3 Hz, 1H), 6.51 (s, 1H), 4.62 (s, 1H), 3.70 (s, 3H).

Analogously, the following compounds are prepared in the same manner:

| No. | Reactant 1 | Product | Yield |
|---|---|---|---|
| 14a | 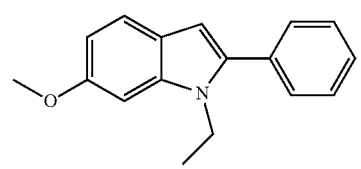 | 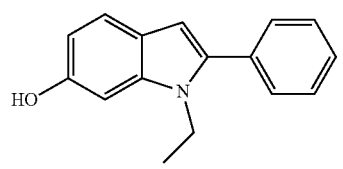 [SMILES: CCn1c(-c2ccccc2)cc2ccc(O)cc21] | 92% |
| 14b | 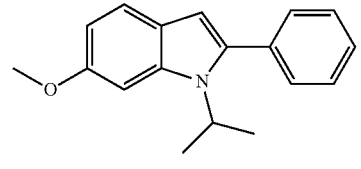 [SMILES: COc1ccc2cc(-c3ccccc3)n(C(C)C)c2c1] | 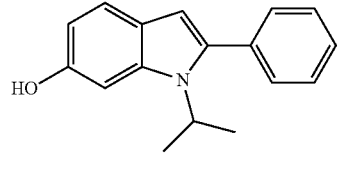 [SMILES: CC(C)n1c(-c2ccccc2)cc2ccc(O)cc21] | 56% |
| 14c | 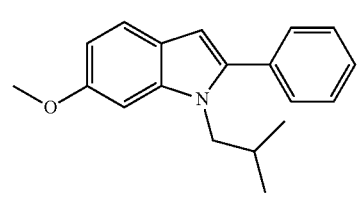 [SMILES: COc1ccc2cc(-c3ccccc3)n(CC(C)C)c2c1] | 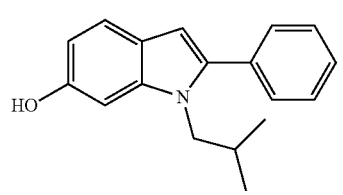 [SMILES: CC(C)Cn1c(-c2ccccc2)cc2ccc(O)cc21] | 60% |

-continued

| No. | Reactant 1 | Product | Yield |
|---|---|---|---|
| 14d | 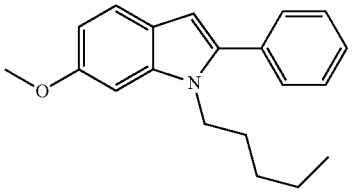 [SMILES: CCCCCn1c(-c2ccccc2)cc2ccc(OC)cc21] | 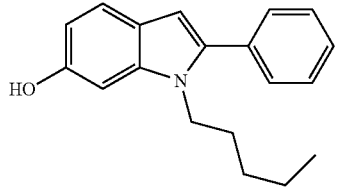 [SMILES: CCCCCn1c(-c2ccccc2)cc2ccc(O)cc21] | 95% |
| 14e | 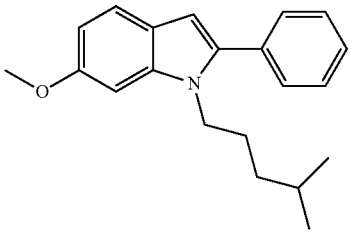 [SMILES: COc1ccc2cc(-c3ccccc3)n(CCCC(C)C)c2c1] | 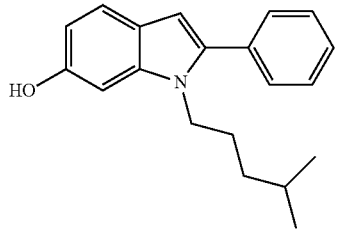 [SMILES: CC(C)CCCn1c(-c2ccccc2)cc2ccc(O)cc21] | 89% |

Example 15: 12-(1-Methyl-2-phenylindol-6-yloxy)-dodecan-1-ol

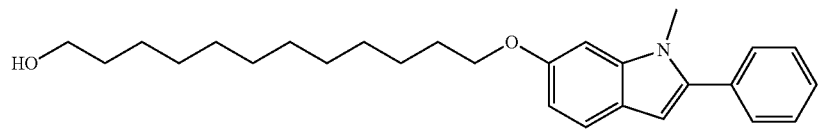 [SMILES: Cn1c(-c2ccccc2)cc2ccc(OCCCCCCCCCCCCO)cc21]

6-Hydroxy-1-Methyl-2-phenylindole (117 mg; 524 μg) and 12-bromo-dodecan-1-ol (146 mg; 550 μg) are dissolved in acetone (20 ml) and potassium carbonate (290 mg; 2.1 mmol) are added. The suspension is refluxed for 3 d. The hot reaction mixture is filtered, washed with hot acetone (2×). The filtrate is evaporated under reduced pressure. The remaining solid is purified by column chromatography over silica gel (chloroform/methanol, 9/1). 12-(1-Methyl-2-phenylindol-6-yloxy)-dodecan-1-ol is isolated in 88% of theory (187 mg; 459 μmol) yield.

1H NMR (500 MHz, Chloroform-d) δ 7.53-7.50 (m, 3H), 7.48 (t, J=7.6 Hz, 2H), 7.40 (t, J=7.2 Hz, 1H), 7.28 (s, 1H), 6.86 (d, J=1.7 Hz, 1H), 6.84 (dd, J=8.5, 2.1 Hz, 1H), 4.08 (t, J=6.6 Hz, 2H), 3.72 (s, 3H), 3.67 (t, J=6.6 Hz, 2H), 1.86 (dt, J=14.5, 6.7 Hz, 2H), 1.60 (p, J=6.7 Hz, 2H), 1.53 (p, J=7.1 Hz, 2H), 1.46-1.30 (m, 15H).

Analogously, the following compounds are prepared in the same manner: R1 means reactant 1, R2 means reactant 2, [P] means product

| No. | | Yield [%] |
|---|---|---|
| 15a | R1 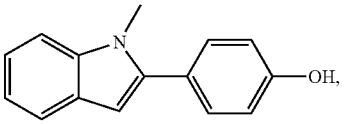<br>CAS: 1013932-64-3<br>R2 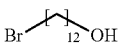 | |
| | [P] 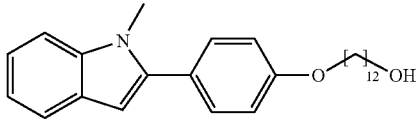 | 88 |
| 15b | R1 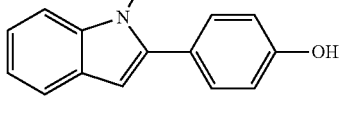<br>R2 Br~~~~~~~~~~OH (10) | |
| | [P] 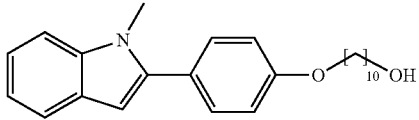 | 79 |
| 15c | R1 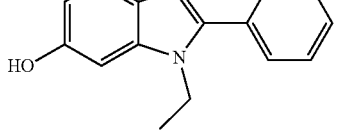 | |

Preparation of Compounds According to the Invention:

Example 16: Acrylic acid 12-(1-methyl-2-phenylindol-6-yloxy)-dodecyl ester

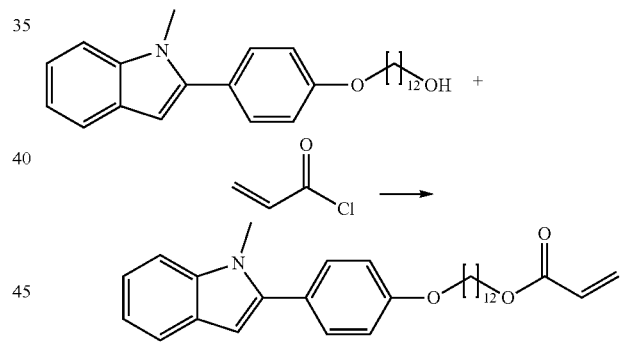

Acryloyl chloride (76.8 µl; 913 µmol) is slowly added to an ice-cooled solution of 12-(1-Methyl-2-phenylindol-6-yloxy)-dodecan-1-ol (186 mg; 456 µmol) in THF (20 ml) and triethylamine (256 µl; 1.8 mmol). Then the reaction is stirred for 2 h at room temperature. The solid which has precipitated out is filtered off with suction and the filtrate is concentrated under reduced pressure. The residue is purified by column chromatography on silica gel (DCM) to yield acrylic acid 12-(1-methyl-2-phenylindol-6-yloxy)-dodecyl ester (173 µg; 375 µmol; 82% of theory).

1H NMR (500 MHz, Chloroform-d) δ 7.54-7.50 (m, 3H), 7.48 (t, J=7.6 Hz, 2H), 7.40 (t, J=7.2 Hz, 1H), 7.28 (s, 1H), 6.89-6.80 (m, 2H), 6.51 (s, 1H), 6.42 (dd, J=17.3, 1.5 Hz, 1H), 6.15 (dd, J=17.3, 10.4 Hz, 1H), 5.83 (dd, J=10.4, 1.6 Hz, 1H), 4.18 (t, J=6.7 Hz, 2H), 4.08 (t, J=6.6 Hz, 2H), 3.72 (s, 3H), 1.86 (dt, J=14.5, 6.7 Hz, 2H), 1.69 (p, J=6.8 Hz, 2H), 1.53 (dt, J=15.2, 7.1 Hz, 2H), 1.43-1.28 (m, 13H).

Analogously, the following compounds are prepared in the same manner: R1 means reactant 1, R2 means reactant 2, [P] means product

| No. | | | Yield [%] |
|---|---|---|---|
| 16a | R1 | 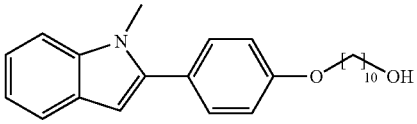 | |
| | R2 | 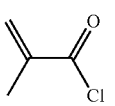 | |
| | [P] | 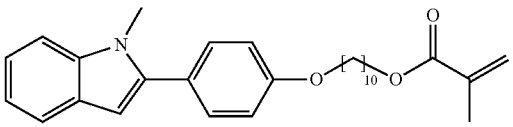 | 85 |
| 16b | R1 | 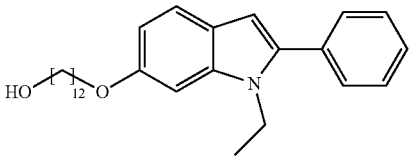 | |
| | R2 | 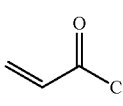 | |
| | [P] | 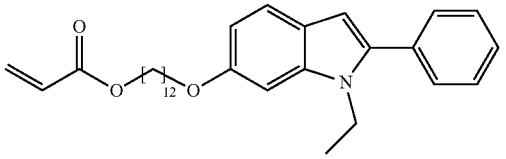 | 79 |
| 16c | R1 | 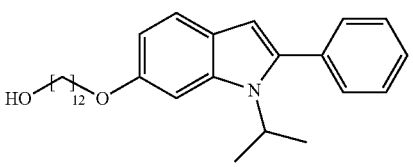 | |
| | R2 | 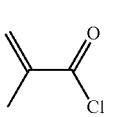 | |
| | [P] | 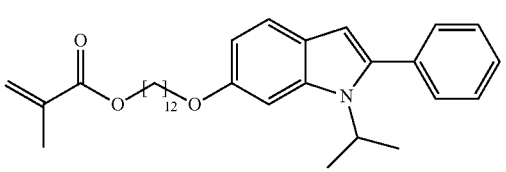 | 87 |
| 16d | R1 | 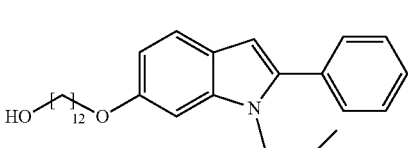 | |
| | R2 | 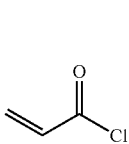 | |

-continued

| No. | | | Yield [%] |
|---|---|---|---|
| | [P] | acrylate ester with -(CH2)12-O- linker to 6-position of 1-isobutyl-2-phenylindole | 67 |
| 16e | R1 | HO-(CH2)12-O- linked to 6-position of 1-pentyl-2-phenylindole | |
| | R2 | methacryloyl chloride | |
| | [P] | methacrylate ester with -(CH2)12-O- linker to 6-position of 1-pentyl-2-phenylindole | 84 |
| 16f | R1 | HO-(CH2)12-O- linked to 6-position of 1-(4-methylpentyl)-2-phenylindole | |
| | R2 | acryloyl chloride | |
| | [P] | acrylate ester with -(CH2)12-O- linker to 6-position of 1-(4-methylpentyl)-2-phenylindole | 76 |

Acrylic acid 12-[4-(1-methylindole-2-yl)-phenoxy]-dodecyl ester

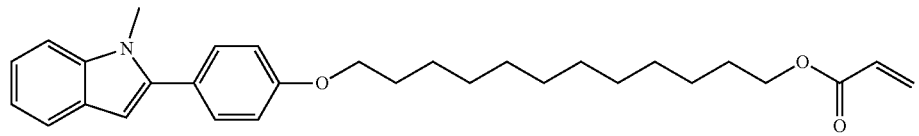 [SMILES: C=CC(=O)OCCCCCCCCCCCCOc1ccc(-c2cc3ccccc3n2C)cc1]

1H NMR (500 MHz, Chloroform-d) δ 7.64 (d, J=7.8 Hz, 1H), 7.44 (d, J=8.7 Hz, 2H), 7.37 (d, J=8.1 Hz, 1H), 7.25 (t, J=7.6 Hz, 1H), 7.16 (t, J=7.4 Hz, 1H), 7.02 (d, J=8.7 Hz, 2H), 6.52 (s, 1H), 6.42 (dd, J=17.3, 1.4 Hz, 1H), 6.15 (dd, J=17.3, 10.4 Hz, 1H), 5.84 (dd, J=10.4, 1.4 Hz, 1H), 4.18 (t, J=6.8 Hz, 2H), 4.05 (t, J=6.5 Hz, 2H), 3.75 (s, 3H), 1.85 (p, J=6.7 Hz, 2H), 1.70 (p, J=6.8 Hz, 2H), 1.55-1.48 (m, 2H), 1.44-1.30 (m, 14H).

Example 17: General Polymerization Procedure

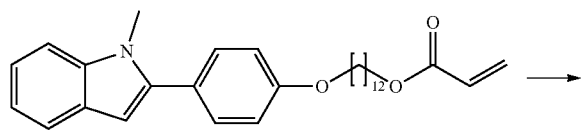 →

-continued

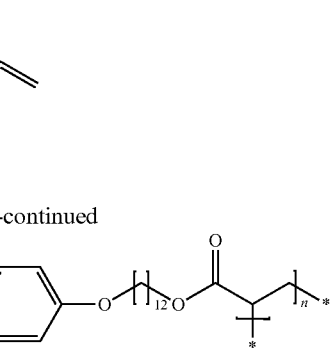

12-(4-(1-methyl-1H-indol-2-yl)phenoxy)dodecyl acrylate (0.914 g; 1.98 mmol) is dissolved in dimethylformamide (10 ml; 129 mmol). The solution is degassed by three freeze-evacuate-thaw cycles. Azobisisobutyronitrile (16.6 mg; 0.1 mmol) is added to the solution and the reaction vessel is then placed in a 65° C. preheated oil bath for 3 d. The mixture is then poured into cold methanol (850 ml; 21 mol). The precipitated Polymer (973.5 mg; 1.6 mmol; 61% of theory) is collected by filtration.

Analogously, the following polymers are prepared in the same manner:

| No. | Reactant | Product | Yield |
|---|---|---|---|
| 17a | | | 65% |
| 17b | | | 62% |
| 17c | | | 70% |
| 17d | | | 74% |
| 17e | | | 71% |

| No. | Reactant | Product | Yield |
|---|---|---|---|
| 17f | 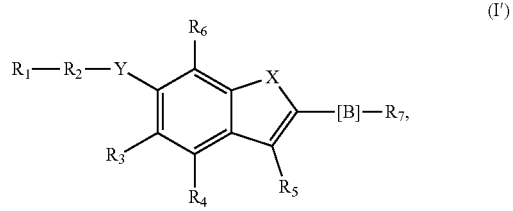 | | 56% |

Examples of Application

Example 18: General Bulk Polymerization Procedure to Produce Blank

A composition of 12-[2-(phenyl)benzofuran-6-yl]oxydodecyl acrylate as described in example 9a and methyl methacrylate, initiator azobisisobutyronitrile (0.04 eq) and crosslinker ethylene glycol dimethacrylate (0.1-0.4 eq) in different ratios is degassed by three freeze-pump-thaw cycles.

Two glass plates are coated with a polyethylene sheet and a 0.5 mm thick cell is created between the polyethylene sheets using a silicone rubber gasket. The coated faces of the glass sheets are clipped together using spring clips with a syringe needle being placed between the gasket and the polyethylene sheets. The cavity is then filled with the above formulation through the needle using a gastight syringe. Once the cavity is filled the syringe needle is removed, a final clip is used to seal the mould and the assembly is placed in an oven at 60° C. for 24 hours before the oven is ramped to a temperature of 90° C. for a period of 3 hours. The moulds are allowed to cool to room temperature before the film is removed from the mould.

Examples Directed to the Properties of the Compounds

Example 19—Photoinduced Refractive Index Change and Glass Transition Temperature The phase transition temperatures are determined with a TA Instruments Q2000 differential scanning calorimeter during heating in the second heating run with 20 K/min from −100° C. to 200° C. in a hermetic aluminium pans.

Irradiations of the blanks are performed with a Coherent Avia 355-7000 UV-Laser.

Common photoactive polymers that undergo refractive index change upon irradiation with UV-light exhibit glass transition temperatures as low as 34° C.

Polymer films for refractive index measurements are prepared by spin coating or drop casting from 1-8 wt % solutions of the polymers in chloroform onto silicon wafers or quartz plates. For production of bulk polymer blanks, the monomers are melted under vacuum. Appropriate amounts of a radical initiator and cross-linker are mixed in and quickly filled into a heated polymerization chamber. Cross-linked polymer plates are obtained.

Refractive index change is induced by irradiation at 340-365 nm. The refractive indices (n) of the polymer films and blanks are measured on Schmidt+Haensch AR12 before and after irradiation. The following table shows the refractive indices before and after irradiation as well as the change in refractive index (max. Δn).

| Polymer No | $T_g$ [° C.] | n | Δn |
|---|---|---|---|
| P-03 | 27.2 | 1.610 | 0.044 |
| P-06 | −10.4 | 1.582 | 0.029 |
| P-124 | 11.5 | 1.625 | 0.037 |

The invention claimed is:

1. A compound of formula (I'):

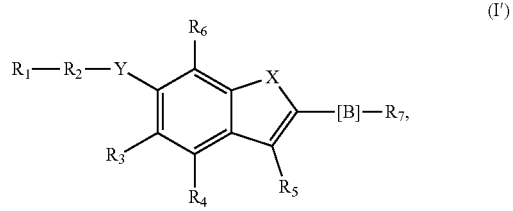

(I')

wherein
X is O, S or $NR_0$,
Y is independently of each other O, S or a bond,
—[B]— is selected from formula (1) to formula (4),

(1)

(2)

(3)

(4)

$X_1$, $X_2$, $X_3$, $X_4$ are each independently of each other CR' or N,
$X_5$ is each independently O, S, C=O or $NR_0$,
$X_6$, $X_7$ are each independently CR' or N,
R is at each occurrence independently H, a linear or branched alkyl group having 1 to 10 C atoms, or a cycloalkyl group having 3 to 6 C atoms, R' is at each occurrence independently H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, or a linear or branched, non-halogenated, partially or completely halogenated thioalkyl group having 1 to 20 C atoms, $R_0$ is at each occurrence independently a linear or branched alkyl group having 1 to 10 C atoms or a cycloalkyl group having 3 to 6 C atoms, $R_1$ is a polymerizable group selected from:
an alkenyl group of formula (5),

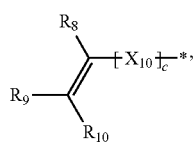
(5)

wherein
$X_{10}$ is O, S, C(=O), or C(=O)O,
$R_8$, $R_9$, $R_{10}$ are at each occurrence independently of each other selected from H, F, a linear or branched, non-fluorinated, partially or completely fluorinated alkyl having 1 to 20 C atoms or aryl with 6 to 14 C atoms, and
c is 0 or 1;
trialkoxysilyl groups or dialkoxyalkylsilyl groups where the alkyl and/or alkoxy groups are each independently linear or branched having 1 to 6 C atoms; and
silyl groups of formula (6), (7) or (8),

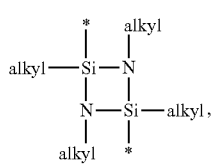
(6)

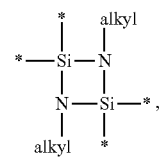
(7)

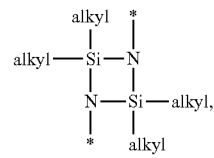
(8)

where alkyl means at each occurrence independently of each other a linear or branched alkyl group having 1 to 6 C atoms and the asterisk "*" denotes at each occurrence independently of each other a linkage to the linker $[-R_2-Y]_n$ and/or $[Y-R_2]_m$, $R_2$— is —$(C(R)_2)_o$— or —$(C(R)_2)_p$—$X_8$—$(C(R)_2)_q$—$(X_9)_s$—$(C(R)_2)_r$—;

o is 1 to 20,
$X_8$, $X_9$ are at each occurrence independently O, S or $NR_0$,
s is 0 or 1,
p, q are at each occurrence independently 1 to 10,
r is at each occurrence independently 0 to 10, wherein the overall number of atoms for —$(C(R)_2)_p$—$X_8$—$(C(R)_2)_q$—$(X_9)_s$—$(C(R)_2)_r$— is up to 20 atoms,
$R_3$, $R_4$, $R_5$, $R_6$ are at each occurrence independently R',
$R_7$ is R'.

2. The compound according to claim 1, wherein -[B]- is of formula (1) or formula (2).

3. The compound according to claim 1, wherein $X_1$, $X_3$, and $X_4$ in formulae (1) or (2) are CR' and R' has at each occurrence independently a meaning as indicated in claim 1.

4. The compound according to claim 1, wherein $X_2$ is CR' and R' has a meaning as indicated in claim 1.

5. The compound according to claim 1, wherein at least one R' within $X_1$, $X_2$, $X_3$, $X_4$, $X_6$ or $X_7$ in formulae (1) to (4) is not H.

6. The compound according to claim 1, wherein —$R_2$— is at each occurrence independently —$(C(R)_2)_o$—, and R and o have the meanings indicated in claim 1.

7. The compound according to claim 1, wherein $R_1$ is at each occurrence independently an acryl or methacryl radical.

8. The compound according to claim 1, wherein the compound is selected from the group consisting of:

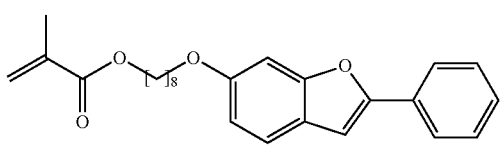
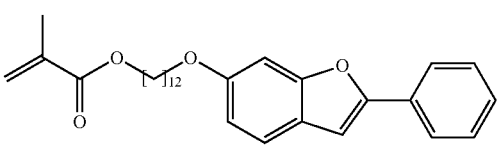
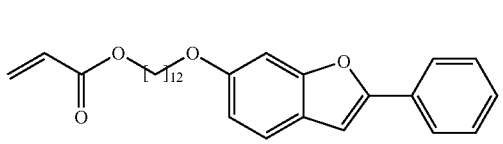
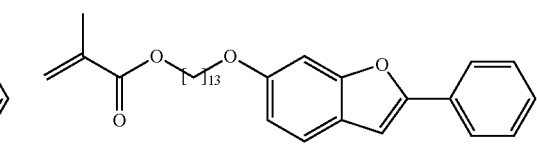

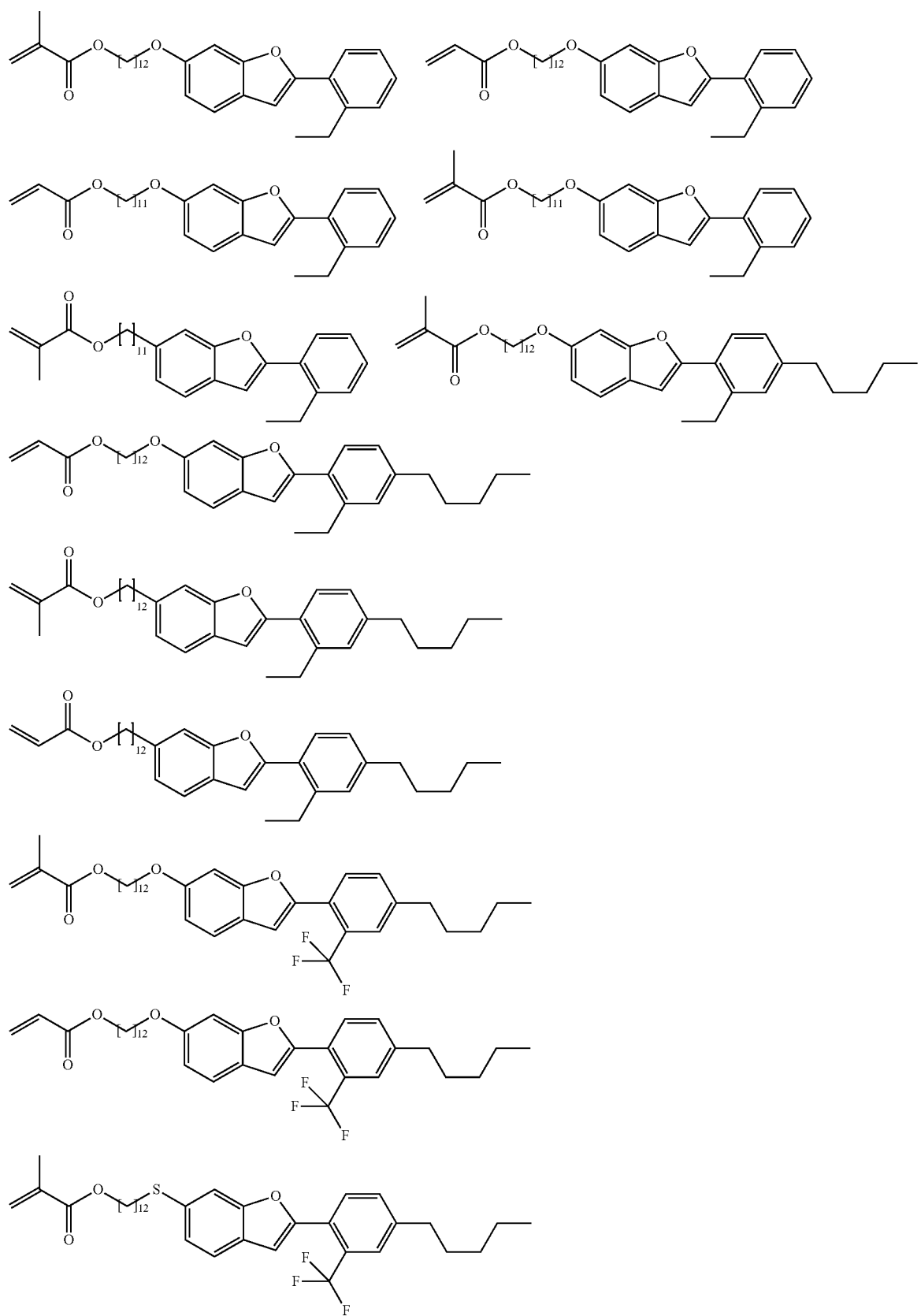

-continued
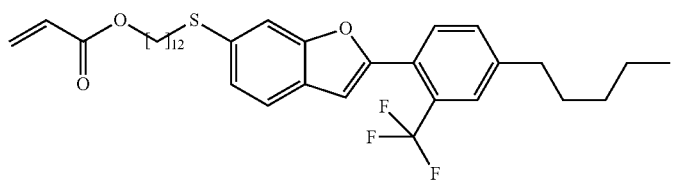
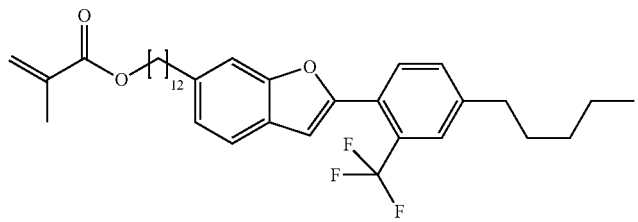
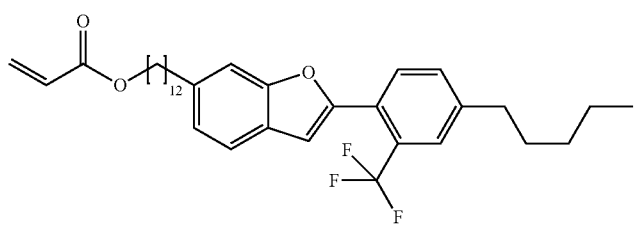
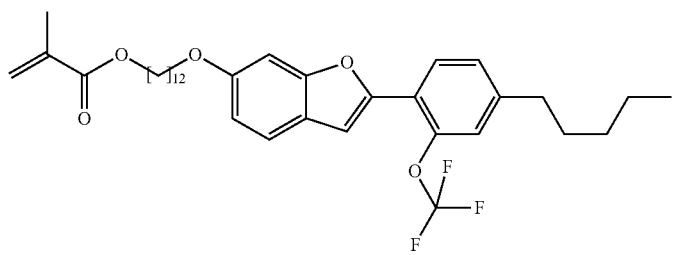
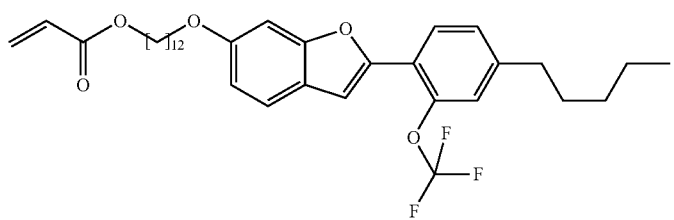
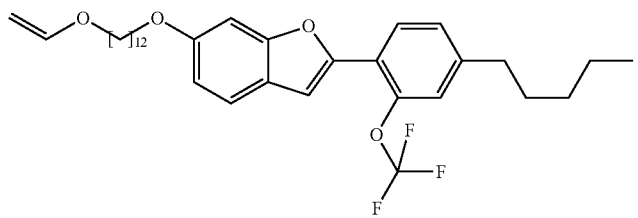
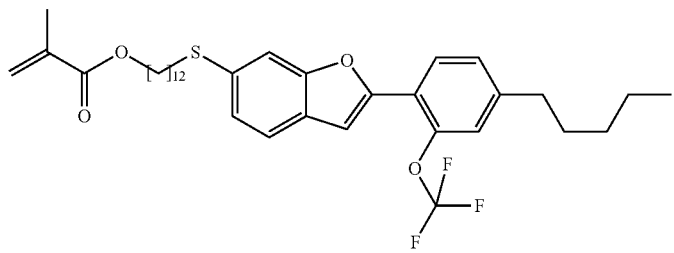

-continued
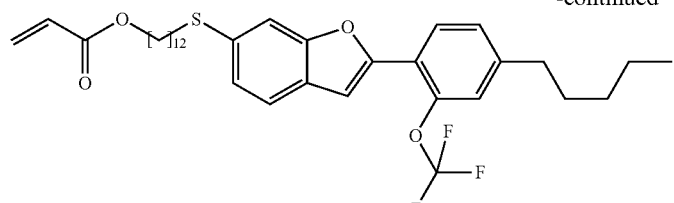
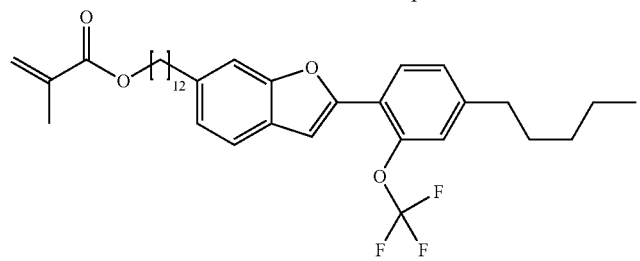
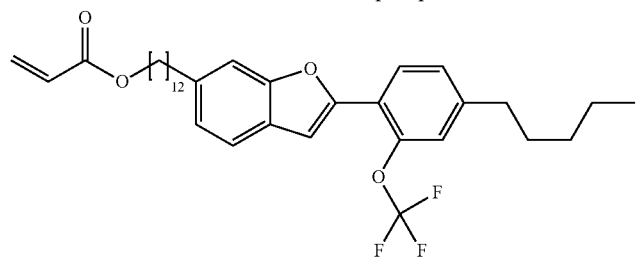
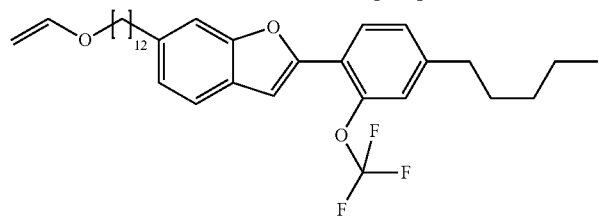
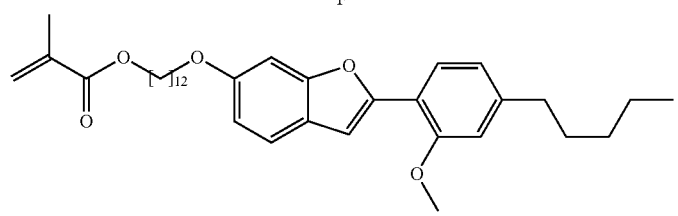
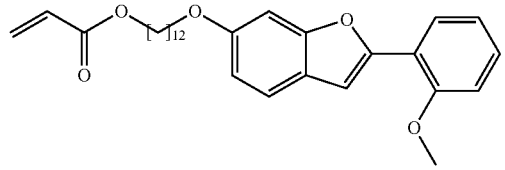
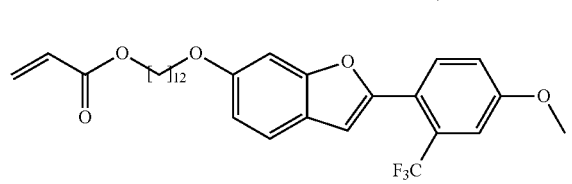
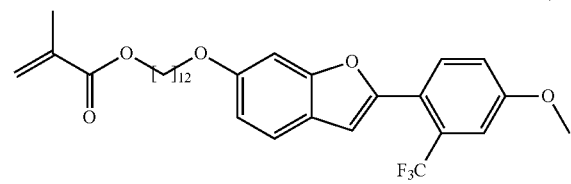
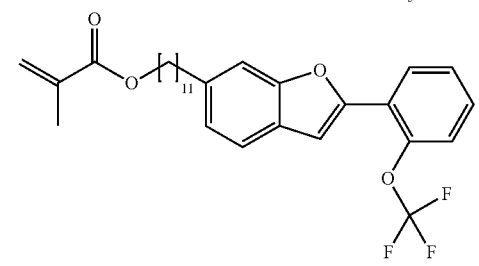
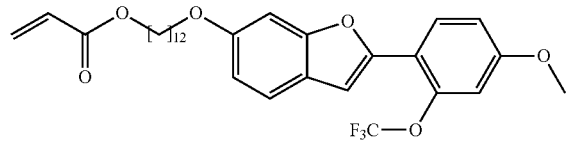

-continued
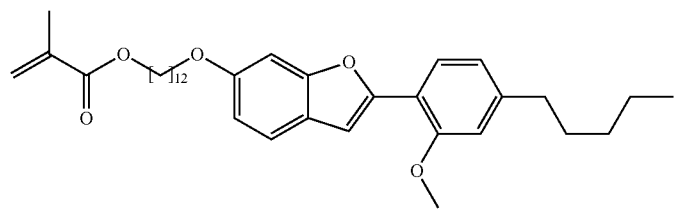
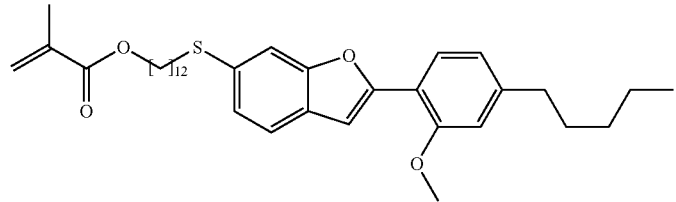
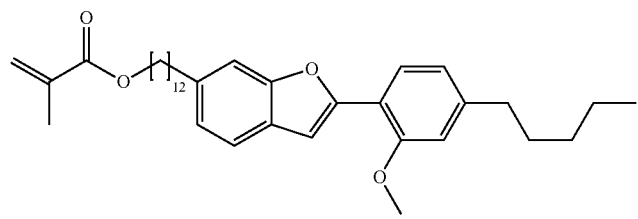
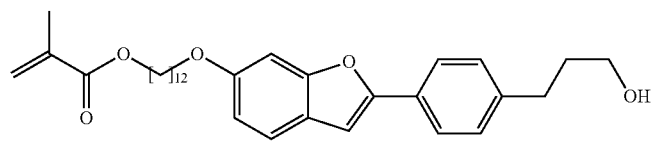
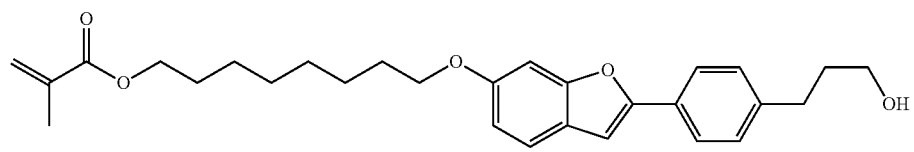
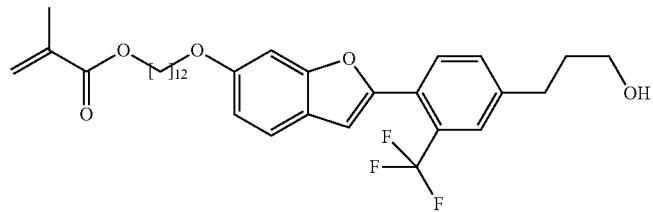
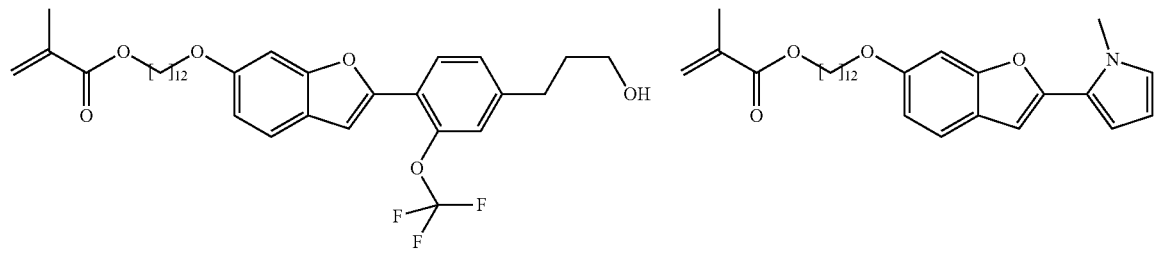
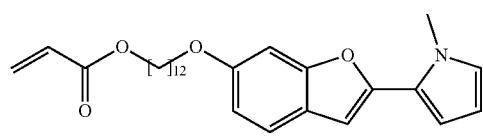
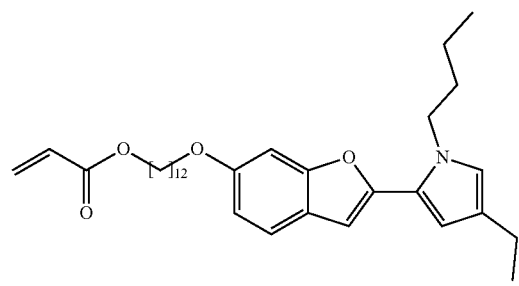

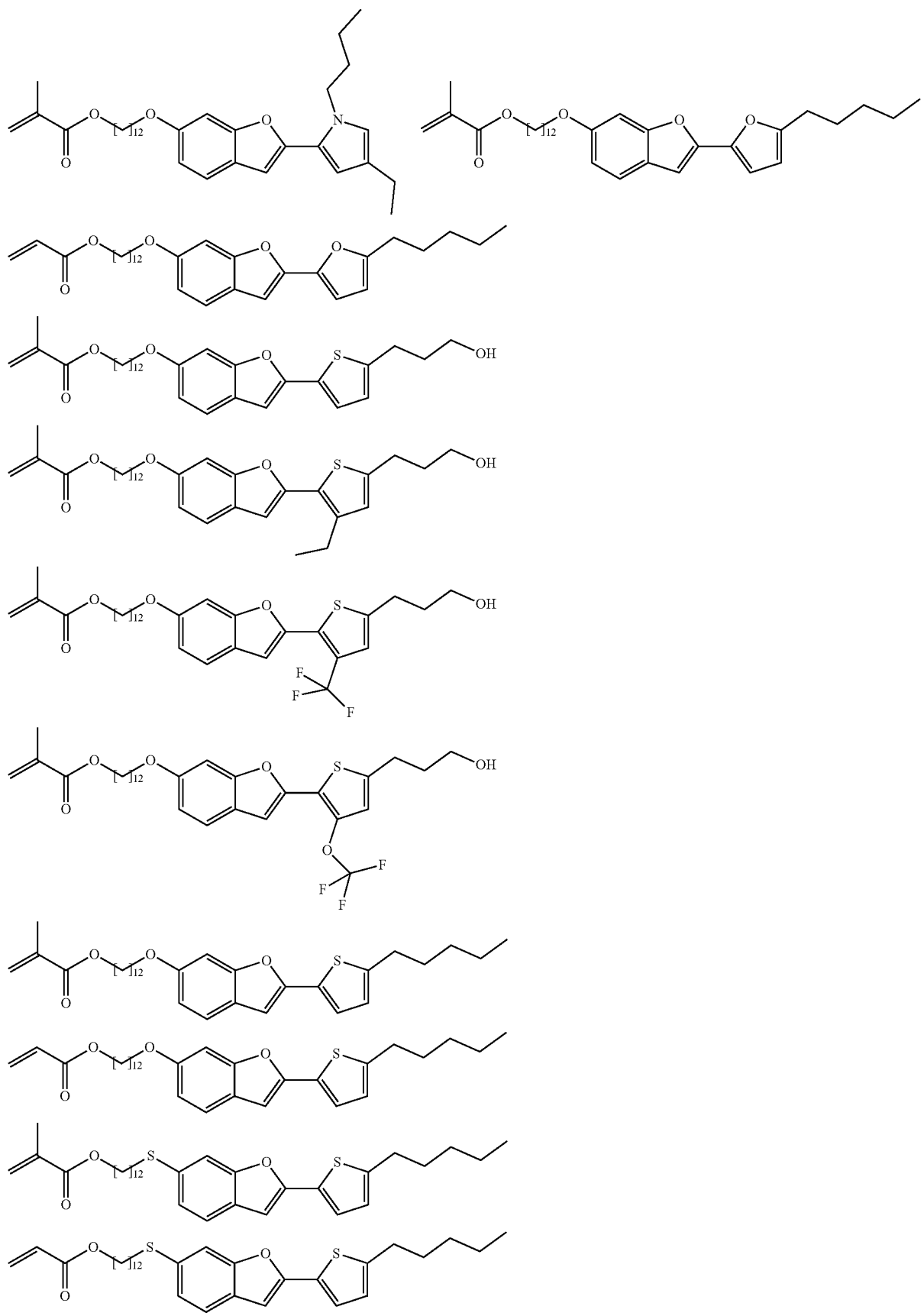

-continued
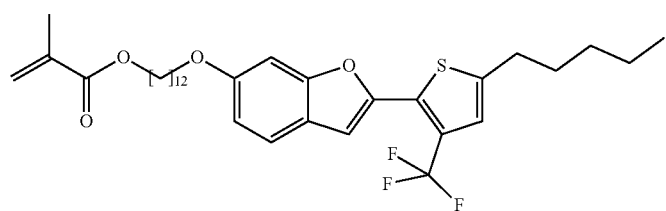
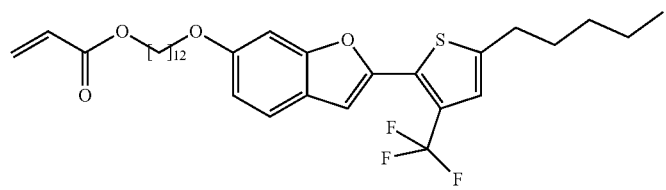
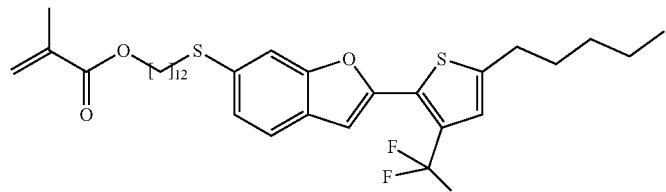
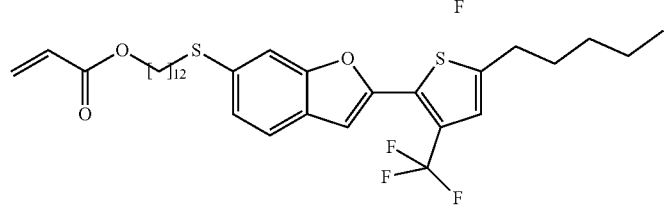
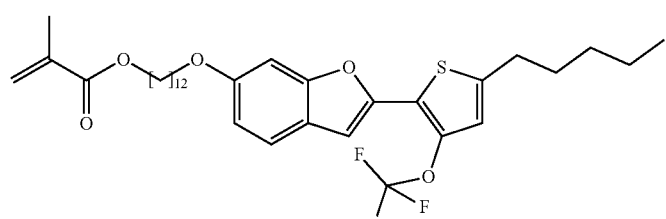
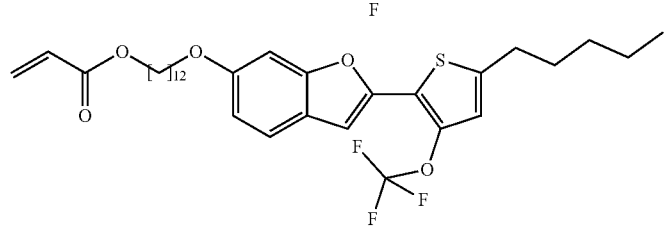
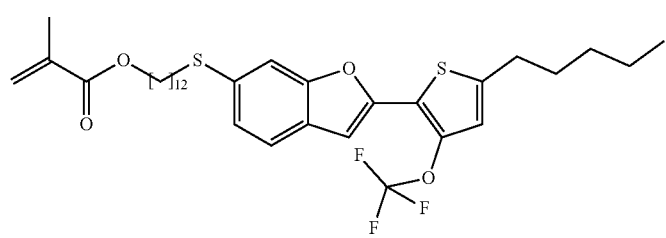
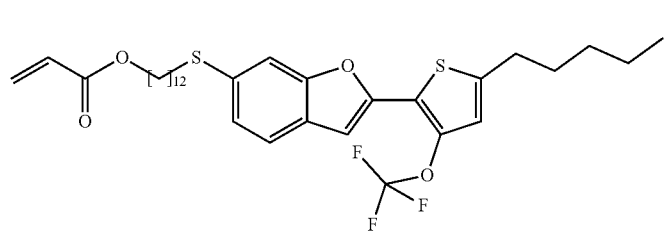
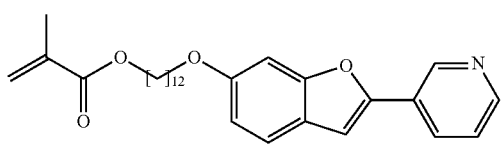

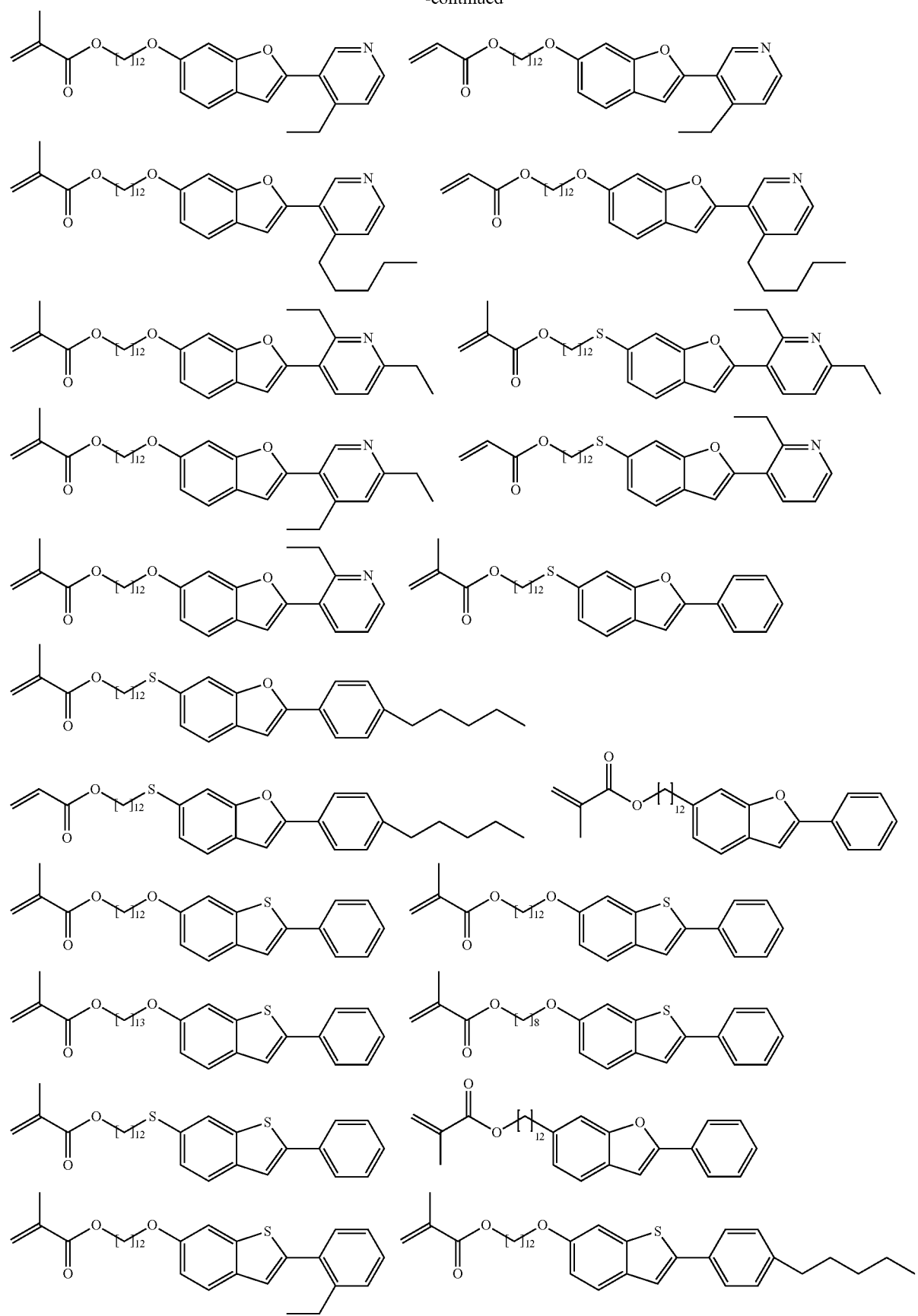

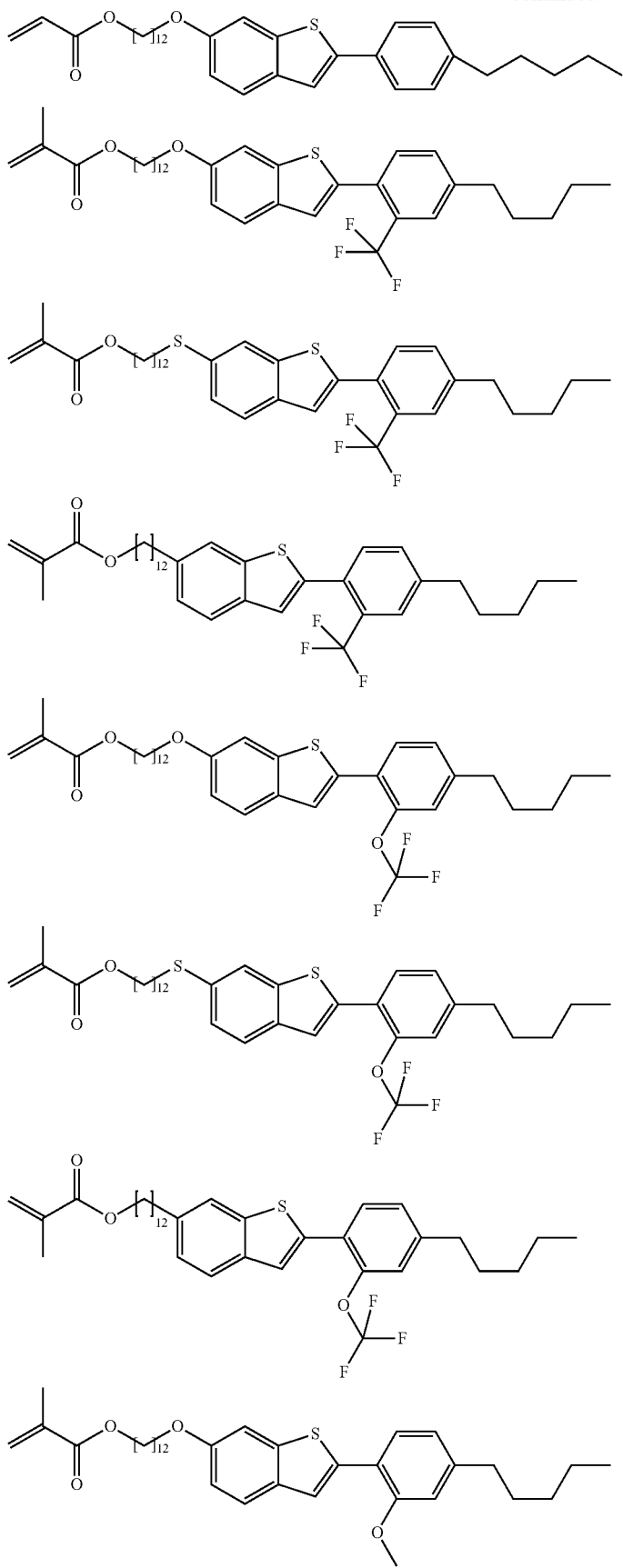

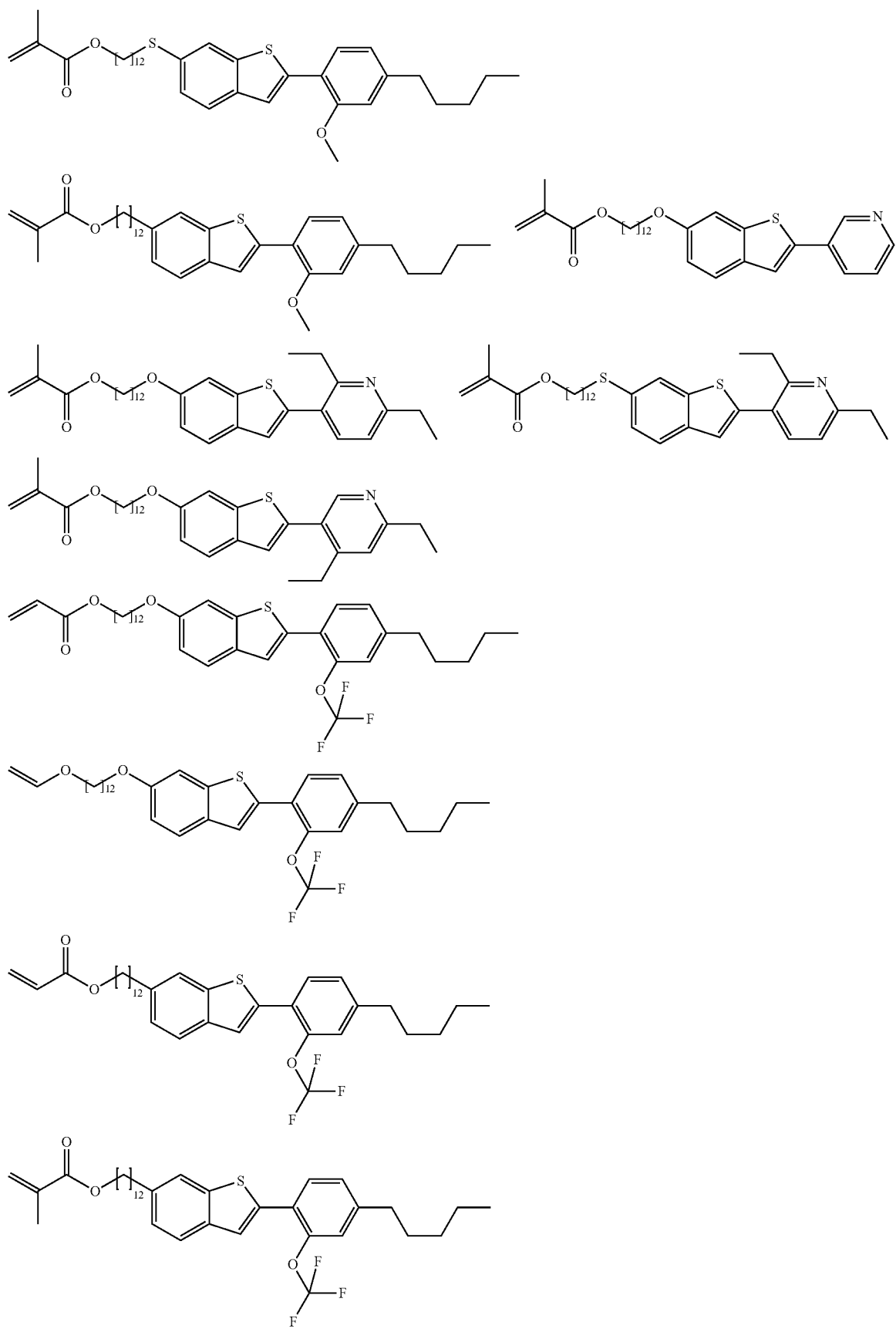

-continued

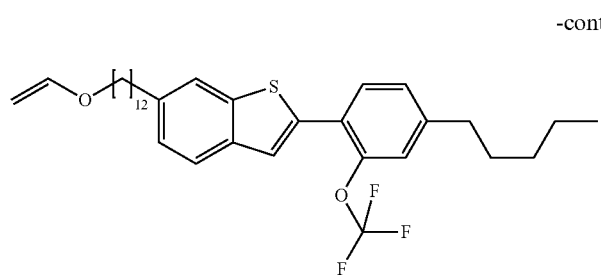
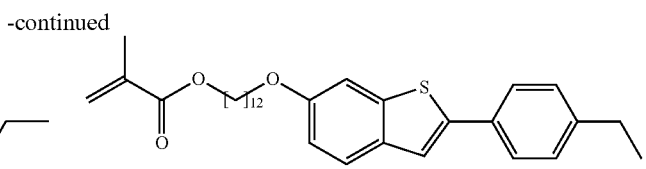
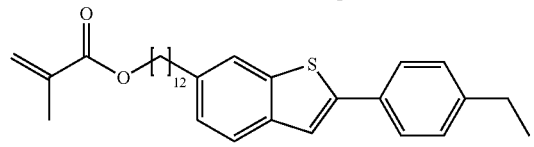
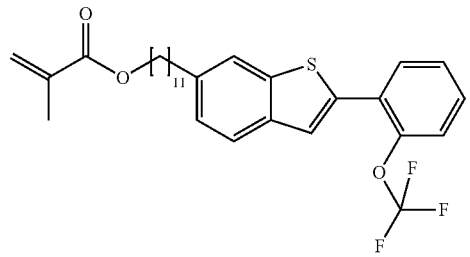
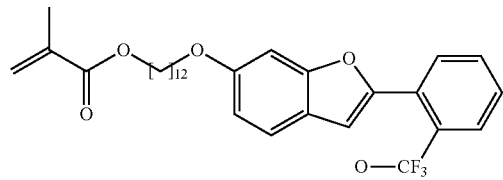
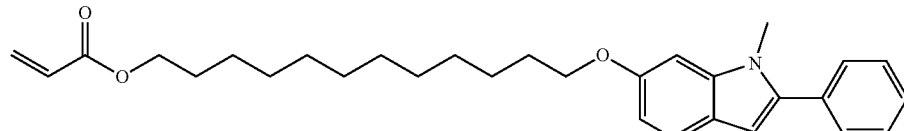
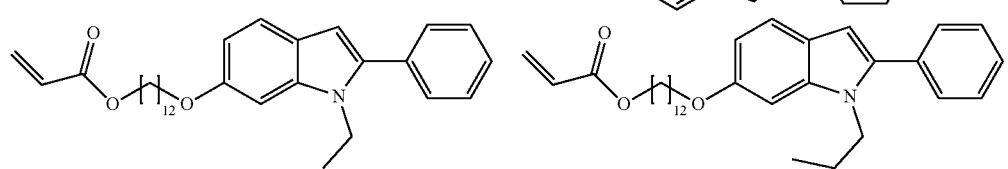
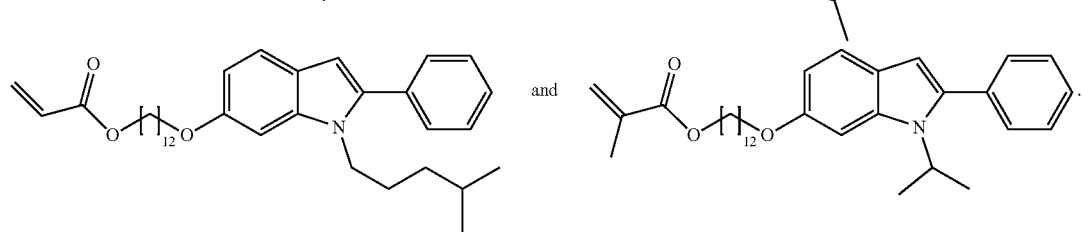

and

9. An oligomer or polymer comprising a polymerized compound of formula (I') according to claim 1.

10. A composition comprising at least one compound of formula (I') according to claim 1.

11. A composition comprising at least one oligomer or polymer according to claim 9.

12. An article comprising at least one oligomer or polymer of claim 9.

13. An article according to claim 12, wherein said article is an intraocular lens.

14. The article according to claim 12, wherein said article is an ophthalmic device.

15. The article according to claim 14, wherein said ophthalmic device is a lens, a keratoprosthesis, a cornea inlay, or a cornea ring.

16. The article according to claim 12, wherein said article is an eye implant.

17. A process of changing the optical properties of an article according to claim 12, said process comprising:
providing an article according to claim 12, and
subsequently exposing said article to irradiation having a wavelength of at least 200 nm and at most 1500 nm.

18. An article according to claim 13, wherein the ophthalmic device comprises one or more optic components and one or more haptic components, wherein the one or more optic components serve as a lens and the one or more haptic components are attached to the one or more optic components and hold the one or more optic components in place in the eye.

19. An article according to claim 13, wherein the article has a one-piece design.

20. An article according to claim 13, wherein the article has a multi-piece design.

21. A process of forming an article, said process comprising:

introducing a compound according to claim 1 into a mold and polymerizing said compound to form a blank, transforming the blank into the article, wherein said article is an ophthalmic device.

22. A process of forming an article, said process comprising:

polymerizing a compound according to claim 1 to form an oligomer or polymer composition, introducing the oligomer or polymer composition into a mold to form a blank, and shaping the blank by cutting, optic lathe cutting, optic milling, and/or haptic milling to form the article, wherein said article is an ophthalmic device.

23. A copolymer comprising a polymerized compound of formula (I') according to claim 1 wherein the polymerizable group $R_1$ forms part of a co-polymer backbone.

24. The copolymer according to claim 19, wherein said copolymer comprises one or more constitutional units $M^0$ of formula (5-p-1:

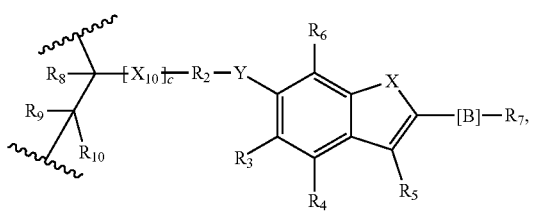

(5-p-1)

wherein —$R_2$—, Y, $R_3$, $R_4$, $R_5$, $R_6$, X, -[B]-, $R_7$, $X_{10}$, $R_8$, $R_9$, $R_{10}$ and c have meanings as defined in claim 1.

25. The copolymer according to claim 20, wherein said copolymer further comprises one or more constitutional units $M^2$ which are chemically different from the units $M^0$.

26. The copolymer according to claim 21, wherein said one or more constitutional units $M^2$ which are derived by polymerization of one or more monomers selected from styrene, ethoxyethyl methacrylate, methyl methacrylate, n-alkyl methacrylates wherein the n-alkyl groups contain 2-20 C-atoms, n-alkyl methacrylates wherein then-alkyl groups contain 2-20 C-atoms, ethoxyethoxy ethylacrylate, 2-hydroxyethyl methacrylate, tetrahydrofuryl methacrylate, glycidylmethacrylate, 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate, bisphenol A diacrylate-1 EO/Phenol, 2-[3'-2'H-benzotriazol-2'-yl)-4'hydroxyphenyl] ethyl methacrylate, trialkoxyalkenylsilane, dialkoxyalkylalkenylsilane, and silanes of formula (9) and (10),

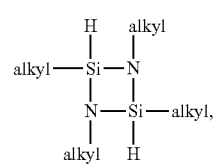

(9)

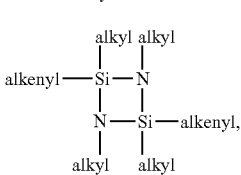

(10)

where the alkyl and/or alkoxy groups are at each occurrence independently of each other linear or branched having 1 to 6 C atoms and the alkenyl group is at each occurrence independently linear having 2 to 4 C atoms.

27. An article comprising at least one copolymer according to claim 24.

28. An article comprising at least one copolymer according to claim 25.

29. An article comprising at least one copolymer according to claim 26.

30. The article according to claim 27, wherein said copolymer is cross-linked.

31. The article according to claim 28, wherein said copolymer is cross-linked.

32. The article according to claim 29, wherein said copolymer is cross-linked.

33. The copolymer according to claim 25, wherein said copolymer comprises the one or more constitutional units $M^0$ in a molar ratio m1 and the one or more constitutional units $M^2$ in a molar ratio m2, wherein the ratio m1:m2 is at least 0.01 and at most 100.

34. An article comprising at least one copolymer according to claim 33.

* * * * *